United States Patent
Franano

(10) Patent No.: US 12,017,057 B2
(45) Date of Patent: Jun. 25, 2024

(54) BLOOD PUMP SYSTEM FOR CAUSING PERSISTENT INCREASE IN THE OVERALL DIAMETER OF A TARGET VESSEL

(71) Applicant: Artio Medical, Inc., Prairie Village, KS (US)

(72) Inventor: F. Nicholas Franano, Olathe, KS (US)

(73) Assignee: ARTIO MEDICAL, INC., Fairway, KS (US)

(*) Notice: Subject to any disclaimer, the term of this patent is extended or adjusted under 35 U.S.C. 154(b) by 0 days.

(21) Appl. No.: 17/816,966

(22) Filed: Aug. 2, 2022

(65) Prior Publication Data

US 2023/0028966 A1     Jan. 26, 2023

Related U.S. Application Data

(60) Continuation of application No. 16/588,721, filed on Sep. 30, 2019, now Pat. No. 11,400,275, which is a
(Continued)

(51) Int. Cl.
*A61M 60/523* (2021.01)
*A61B 5/02* (2006.01)
(Continued)

(52) U.S. Cl.
CPC ....... *A61M 60/523* (2021.01); *A61B 5/02035* (2013.01); *A61M 1/14* (2013.01); *A61M 1/3653* (2013.01); *A61M 1/3655* (2013.01); *A61M 1/3659* (2014.02); *A61M 60/104* (2021.01); *A61M 60/232* (2021.01); *A61M 60/422* (2021.01); *A61M 60/50* (2021.01); *A61M 60/515* (2021.01); *A61M 60/531* (2021.01); *A61M 60/538* (2021.01); *A61M 60/806* (2021.01); *A61M 60/825* (2021.01); *G01N 11/06* (2013.01); *A61M 60/122* (2021.01); *A61M 60/148* (2021.01); *A61M 60/205* (2021.01); *A61M 60/818* (2021.01); *A61M 60/857* (2021.01); *A61M 2205/3334* (2013.01);
(Continued)

(58) Field of Classification Search
None
See application file for complete search history.

(56) References Cited

U.S. PATENT DOCUMENTS

| 4,823,543 A * | 4/1989 | Igel ........................ D01H 13/14 |
| | | 57/83 |
| 2010/0222632 A1 * | 9/2010 | Poirier ................ A61M 60/531 |
| | | 600/16 |

* cited by examiner

*Primary Examiner* — Kennedy Schaetzle
(74) *Attorney, Agent, or Firm* — Polsinelli PC

(57) ABSTRACT

A blood pump system for persistently increasing the overall diameter and lumen diameter of peripheral veins and arteries by persistently increasing the speed of blood and the wall shear stress in a peripheral vein or artery for a period of time sufficient to result in a persistent increase in the overall diameter and lumen diameter of the vessel is provided. The blood pump system includes a blood pump, blood conduit (s), a control system with optional sensors, and a power source. The pump system is configured to connect to the vascular system in a patient and pump blood at a desired rate and pulsatility. The pumping of blood is monitored and adjusted, as necessary, to maintain the desired elevated blood speed, wall shear stress, and desired pulsatility in the target vessel to optimize the rate and extent of persistent increase in the overall diameter and lumen diameter of the target vessel.

17 Claims, 47 Drawing Sheets

Related U.S. Application Data division of application No. 14/239,248, filed as application No. PCT/US2012/050983 on Aug. 15, 2012, now Pat. No. 10,426,878.

(60) Provisional application No. 61/564,671, filed on Nov. 29, 2011, provisional application No. 61/524,761, filed on Aug. 17, 2011.

(51) Int. Cl.
*A61M 1/14* (2006.01)
*A61M 1/36* (2006.01)
*A61M 60/104* (2021.01)
*A61M 60/232* (2021.01)
*A61M 60/422* (2021.01)
*A61M 60/50* (2021.01)
*A61M 60/515* (2021.01)
*A61M 60/531* (2021.01)
*A61M 60/538* (2021.01)
*A61M 60/806* (2021.01)
*A61M 60/825* (2021.01)
*G01N 11/06* (2006.01)
*A61M 60/122* (2021.01)
*A61M 60/148* (2021.01)
*A61M 60/205* (2021.01)
*A61M 60/818* (2021.01)
*A61M 60/857* (2021.01)

(52) U.S. Cl.
CPC ............... *A61M 2205/3344* (2013.01); *A61M 2205/502* (2013.01); *A61M 2205/82* (2013.01)

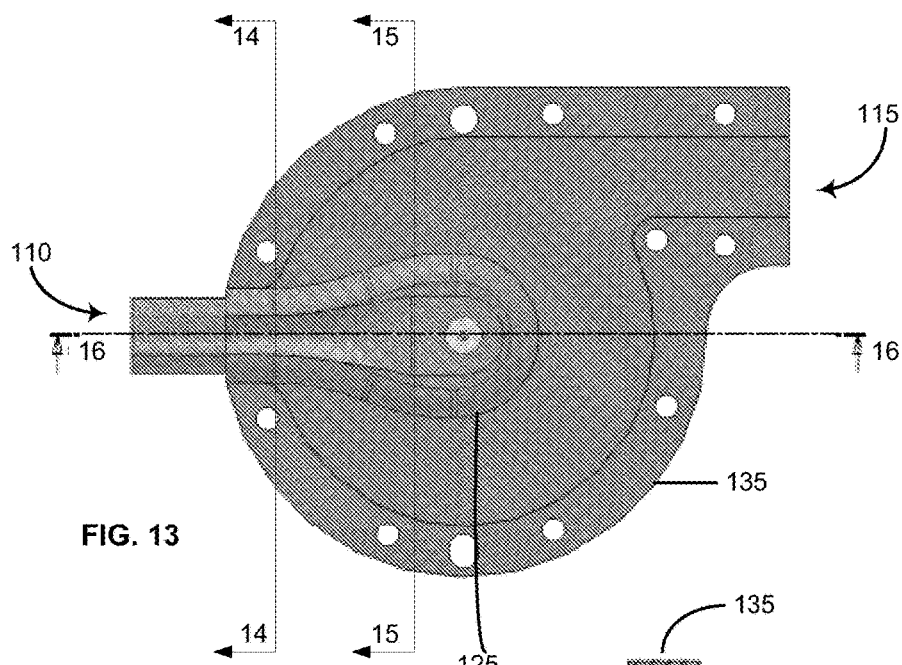
FIG. 13
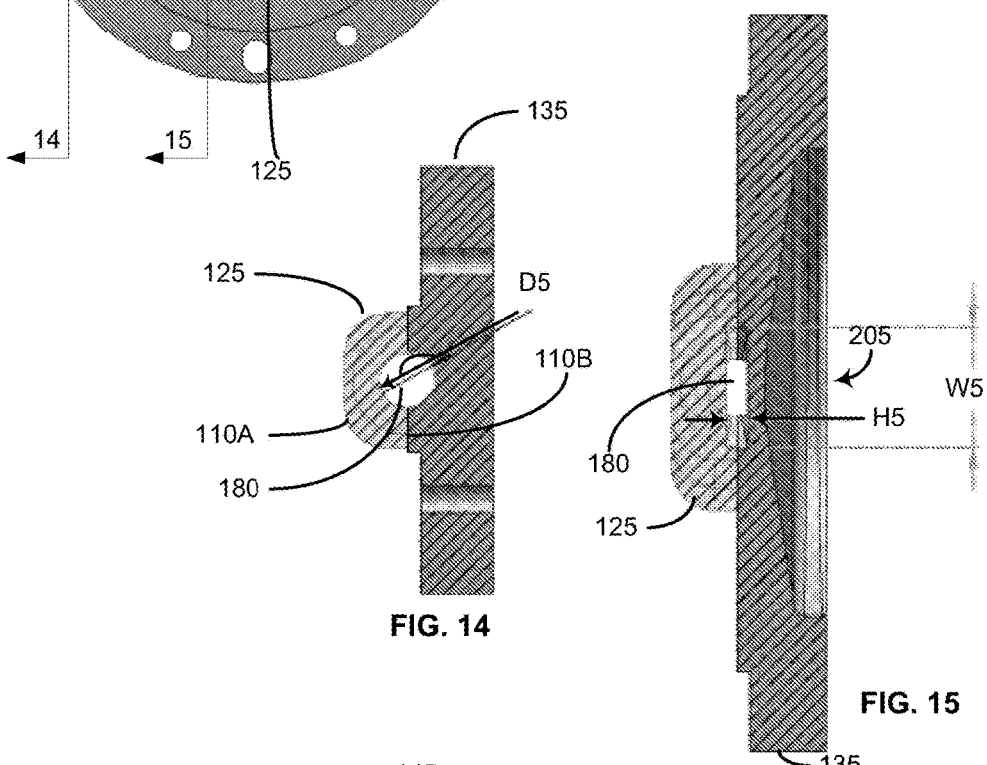
FIG. 14
FIG. 15
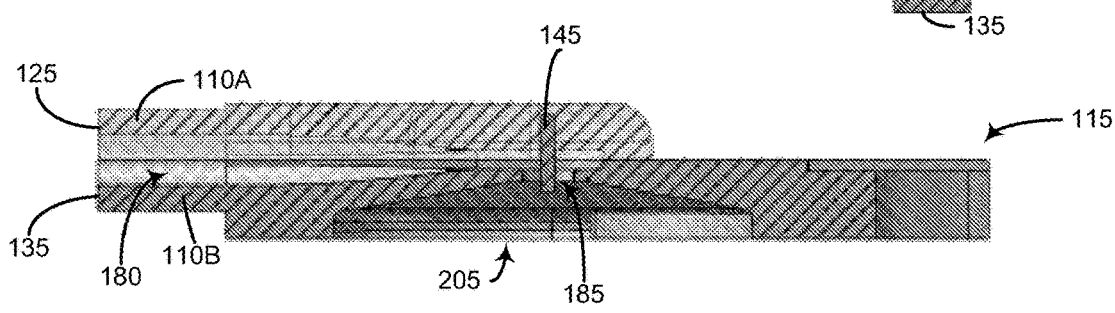
FIG. 16

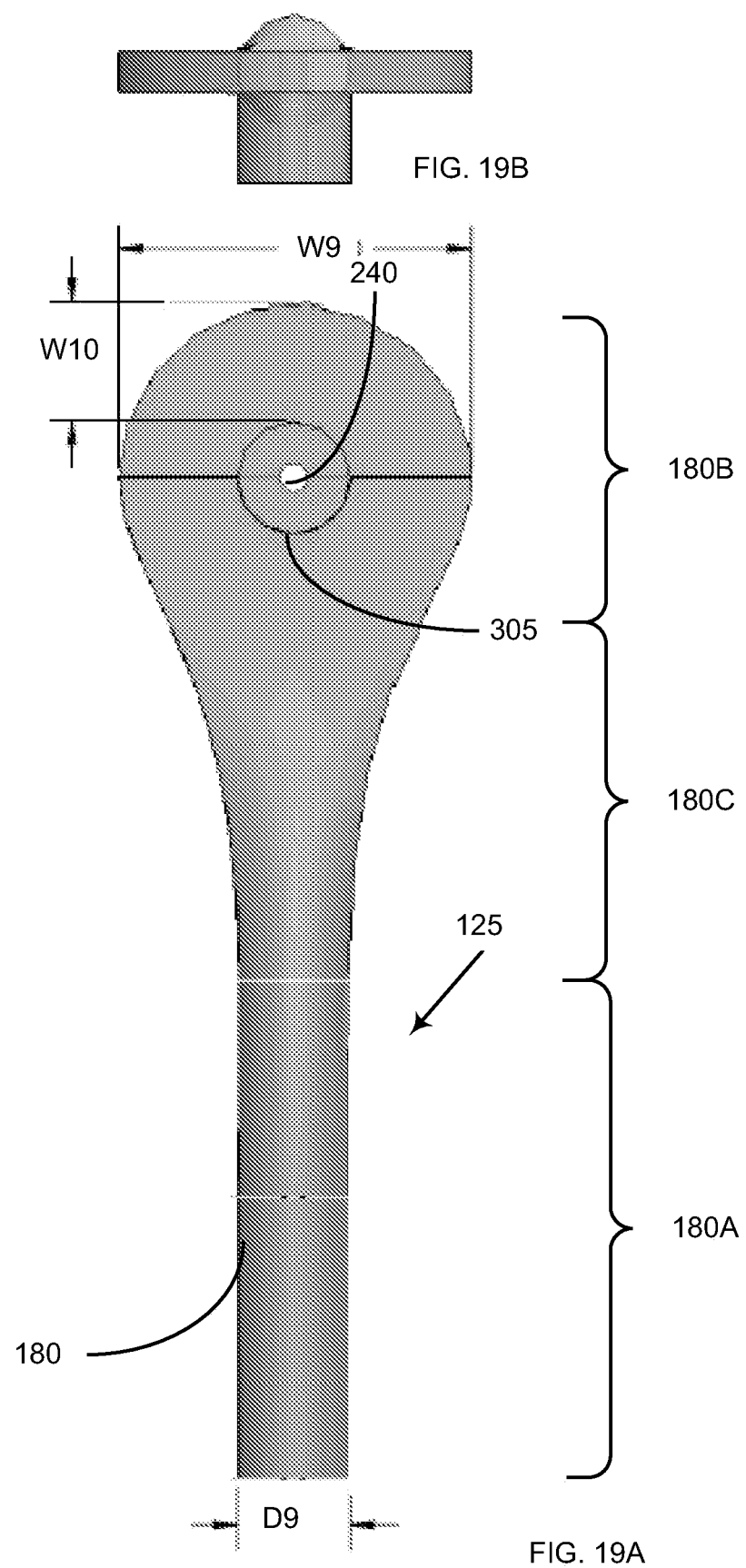

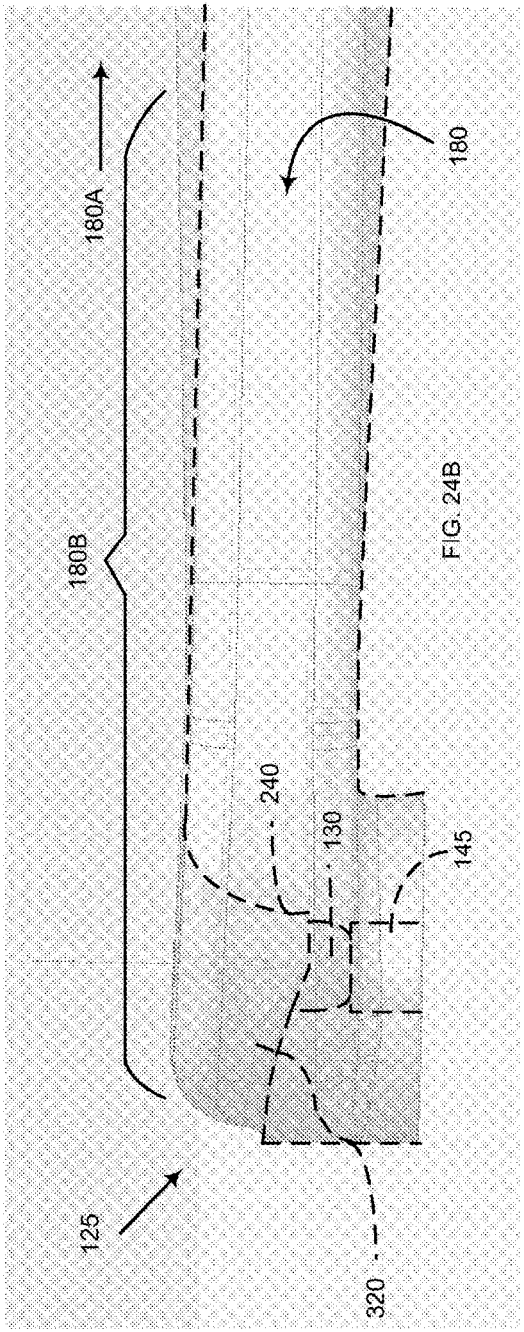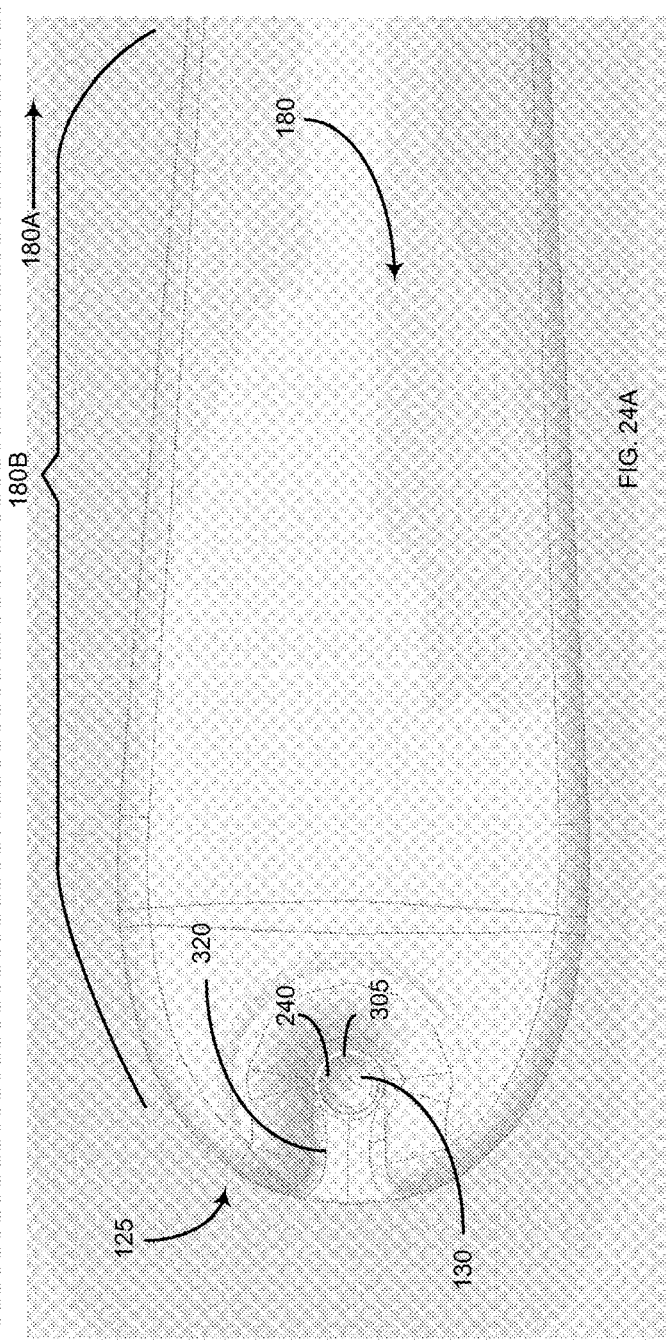

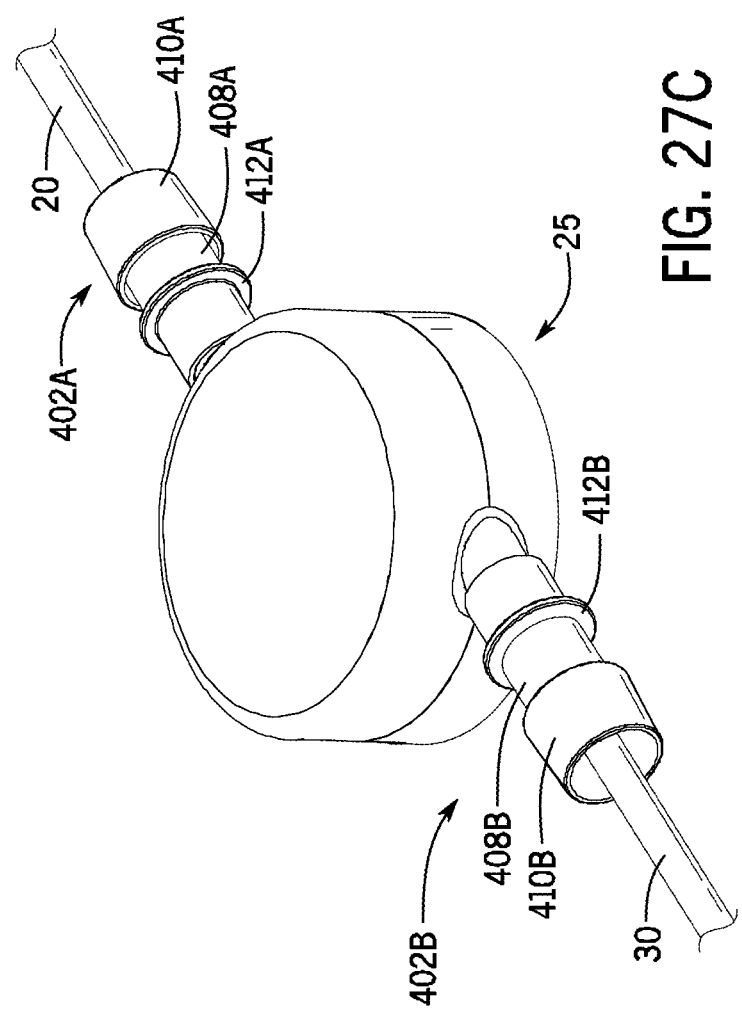

BLOOD PUMP SYSTEM FOR CAUSING PERSISTENT INCREASE IN THE OVERALL DIAMETER OF A TARGET VESSEL

CROSS REFERENCE TO RELATED APPLICATIONS

This application is a continuation of application of U.S. patent application Ser. No. 16/588,721, entitled "Blood pump system for causing persistent increase in the overall diameter of a target vessel," filed on Sep. 30, 2019, now U.S. Pat. No. 11,400,275, which is continuation of U.S. patent application Ser. No. 14/239,248, entitled "Blood Pump Systems and Methods," filed on May 29, 2014, now U.S. Pat. No. 10,426,878, which is a National Stage Entry of International Application No. PCT/US2012/050983, entitled "Blood Pump Systems and Methods," filed Aug. 15, 2012, which claims priority to provisional U.S. Patent Application No. 61/564,671 entitled "Blood Pump Systems and Methods," filed on Nov. 29, 2011, and claims priority to provisional U.S. Patent Application No. 61/524,761, entitled "System and Method to Increase the Overall Diameter of Veins," filed on Aug. 17, 2011, each of which are incorporated by reference in their entireties.

FIELD OF THE INVENTION

The present invention relates to a blood pump system that includes a pump, conduits, a control unit, and a source of power, whereby the system may be used to persistently increase local blood flow in arteries and veins of patients. Specifically, this invention may be useful for persistently increasing the overall diameter and lumen diameter of veins and arteries in patients needing a vascular access site for hemodialysis, a bypass graft, or other type of surgery or procedure where a larger vein or artery diameter is desired. This invention may also be useful for providing increased local blood flow to organs and tissues in need thereof, such as the lower extremities of patients with peripheral arterial disease (PAD).

BACKGROUND INFORMATION

There are over half a million chronic kidney disease (CKD) patients in the United States, with over 100,000 new CKD patients each year. There is a four percent annual increase in projected prevalence population due to such driving factors as, for example, high blood pressure, diabetes, and an aging population.

Hemodialysis is the treatment of choice for 92% of CKD patients, because without hemodialysis or some other form of treatment those CKD patients would die. A typical CKD patient undergoing hemodialysis treatment must have his or her vascular system connected to a hemodialysis machine two to three times per week. For hemodialysis, there are three common vascular access site options. The preferred access site option is an arteriovenous fistula (AVF), which is a direct, surgically created connection between an artery and a vein, preferably in the wrist, or alternatively, in the forearm, upper arm, leg, or groin. Another access site option is an arteriovenous graft (AVG), which is a surgically created connection between an artery and vein using an interposed synthetic conduit. The final major access site option is a catheter inserted into a large vein in the neck, chest, leg, or other anatomic location.

Patients with an AVF have less morbidity, less mortality, and a lower cost of care compared with patients with an AVG or a catheter; therefore, an AVF in the wrist is the preferred form of vascular access for hemodialysis. Patients with an AVG or catheter have substantially higher rates of infection and death than patients having an AVF, with catheter patients having the worst outcomes. In addition, patients having an AVG or catheter have a higher average cost of care, with catheter patients having the highest costs. If a patient is eligible for an AVF, the wrist or forearm is generally preferred over an AVF in the upper arm due to higher rates of hand ischemia and the generally shorter and deeper vein segments of the upper arm.

Unfortunately, about 85 percent of patients are ineligible for an AVF in the wrist, mostly due to vein and artery diameters that are too small. Furthermore, about 60 percent of all AVFs created are not useable without additional surgical and interventional procedures due to an occurrence commonly referred to as "maturation failure," which is correlated with small vein and artery diameter. The availability of veins and arteries with larger diameters is correlated with higher AVF eligibility and lower rates of maturation failure.

Currently, there are few options for permanently and persistently increasing the diameter of a vein or artery. All current methods use mechanical methods of dilation, such as balloon angioplasty, that can lead to vein or artery injury. Since a patient needs to have peripheral veins and arteries of a certain size for a physician to create an AVF, it is desirable to have a method and system for persistently and permanently increasing the size or diameter of peripheral veins or arteries.

Currently, small "heart pumps" exist. However, such pumps are costly and not designed and dimensioned for use in an extremity. As such, there is a need in the art for systems, components, and methods of increasing the diameter of peripheral veins and arteries at a reasonable cost. Additionally, there is a need for a pump device that can increase the diameter of peripheral veins and arteries.

SUMMARY OF THE INVENTION

The present application relates to a blood pump system for use in increasing the diameter of veins and arteries, preferably peripheral veins and arteries. The system will function to move blood in such a way as to cause an increase in vein or artery diameters. This can be accomplished by discharging ("pushing") blood into a vein or artery or by removing ("pulling") blood from a vein or artery. By either method, the system increases the flow of blood in a vessel, which ultimately leads to a persistent increase in vessel diameter. As such, the system and, more particularly, the pump use mechanical means to activate biological response pathways resulting in the enlargement or "remodeling" of veins or arteries. The system has a blood pump, conduits to carry blood to and from the blood pump, a control system to monitor the blood pump and modify the operation of the blood pump, and a power source. As such, the system comprises a group of members that can be, for example, inserted into an artery at one end and a vein at the other, whereby, when activated, blood is pumped at a rate such that wall shear stress (WSS) on the endothelium of the vein, artery, or both is elevated for a period of time sufficient to causes a persistent enlargement in the vein or artery. Any of a variety of pumps may be used so long as the pump can be controlled to produce the desired blood vessel diameter increase.

Various types of blood pumps may be employed, including positive displacement and rotary pumps, with rotary type pumps being preferred. In one embodiment, a rotary blood pump system includes a pump having a housing defining an inlet to receive blood and an outlet to discharge blood. The pump housing is designed and dimensioned to house a rotating impeller suspended on bearings. The pump housing can have a first bearing at the inlet portion of the housing and a second bearing at the outlet portion of the housing. Blood enters and exits the rotating impeller, whereby the impeller increases the exit speed of the blood. This increased speed is recovered or translated as increased pressure as the blood decelerates within the pump diffuser, which terminates in the pump outlet.

In other embodiments, various types of rotary blood pumps may be used. For example, an axial flow pump, a mixed flow pump, or preferably, a centrifugal blood pump may be used. In addition, a variety of pump impeller bearings may be used, including, but not limited to magnetic bearings, hydrodynamic bearings, and, preferably pivot (contact) types. Similarly, various types of pump diffusers may be used, including but not limited to a collector diffuser, or preferably a volute diffuser.

In one embodiment, a centrifugal blood pump with pivot bearings includes a pump housing defining a pump inlet having an inflow diffuser to receive blood and direct blood onto an impeller, the pump housing having a top bezel and top pivot bearing extending from a top of the housing into the inlet, and a bottom bezel and bottom pivot bearing extending from a bottom of the housing into the interior space of the housing. The pump also includes the impeller suspended within the housing, the impeller further having a bearing lumen to receive an impeller pivot. The impeller pivot has a first end to engage the inlet portion (top) pivot bearing and a second end to engage the outlet portion (bottom) pivot bearing. In one embodiment, the ends of the impeller pivot are convex and at least one end of each pivot bearing is concave. In another embodiment, the ends of the impeller pivot are concave and the pivot bearings are convex. The impeller can include a variety of fin or blade constructions designed to contact and accelerate blood into the volute. For example, the impeller defines a plurality of blades on the top surface of the impeller and extending radially from a center of the impeller to an outer edge of the impeller. The blades accelerate blood from the impeller's central inlet to its peripheral outlet. In another option, the impeller does not include blades or fins, but does include means to move or propel blood. The impeller optionally includes at least one washout lumen, cut-away, or bore extending parallel to a central axis of the impeller from a bottom surface through the impeller to a top surface. The lumen is designed to prevent stagnation of blood under the impeller and around the bottom pivot bearing.

The blood pump includes a motor, preferably electric, designed to actuate the impeller. In one embodiment, the blood pump includes a drive motor having at least one magnet mechanically attached to the impeller and at least one armature mechanically attached to the housing. The armature induces an electromotive force on the at least one magnet attached to the impeller. The pump motor can be an axial-gap brushless direct current (DC) torque motor with sensorless back electromotive force (back emf) commutation. The motor employs a sintered alloy of neodymium iron boron (NdFeB) for the magnets in the rotor and a 3-phase planar "racetrack" coil configuration in the stator. The motor has a pancake aspect ratio, with a very small axial length in comparison to its diameter.

The blood pump system has one or more conduits including a first (inflow) conduit having two ends, a first end that is fluidly connected to a location in the vascular system and receives blood from that location, and a second end that is fluidly connected to the pump. The inflow conduit delivers blood to the pump. The blood pump system has a second (outflow) conduit having two ends, a first end that is fluidly connected to the pump and receives blood from the pump, and a second end that is fluidly connected to a location in the vascular system. The outflow delivers blood to a location in the vascular system.

In various embodiments, the conduits of the blood pump system have an individual length of between 2 cm and 110 cm and a combined length between 4 cm and 220 cm, and may be trimmed to a desired length by a surgeon or other physician, including during implantation of the pump system. The conduits each have an inner diameter between 2 mm and 10 mm, and preferably between 4 mm and 6 mm. The conduits may be formed at least in part from polyurethane (such as Pellethane® or Carbothane®), polyvinyl chloride, polyethylene, silicone elastomer, polytetrafluoroethylene (PTFE), expanded polytetrafluoroethylene (ePTFE), polyethylene terephthalate (PET, e.g. Dacron), and combinations thereof. The conduits may further include an elastic reservoir.

All or portions of the conduits may be reinforced with a braided or spiral coiled shape memory material, such as nitinol, or other self-expanding or radially expansive material. The conduits may have chamfered ends that fluidly connect to the vascular system. The ends can be chamfered at an angle between 10 degrees and 80 degrees. One or more of the conduits may have a number of holes or fenestrations in the walls of the distal ends, when configured for placement within the lumen of a blood vessel or other intravascular location. The conduits may be secured to the pump using radially-compressive connectors.

In one embodiment, a blood pump system includes a blood pump and a control system to monitor the blood pump system and modify the operation of the blood pump to maintain an increased mean wall shear stress within an artery or vein fluidly connected to the blood pump. The control system is further configured to maintain mean wall shear stress within a vein in the range of 0.76 to 23 Pa, or preferably in the range of 2.5 to 10 Pa. In another embodiment, the control system monitors and maintains an increased mean blood speed within an artery or vein fluidly connected to the blood pump. In this embodiment, the control system is configured to maintain mean blood speed within an artery or vein in the range of 10 cm/s and 120 cm/s, or preferably in the range of 25 cm/s and 100 cm/s. In either embodiment, the blood pump system is configured to maintain increased mean wall shear stress or increased mean blood speed for at least 1 day, 7 days, 14 days, 28 days, 42 days, 56 days, 84 days, or 112 days.

The blood pump system has a control system to achieve and maintain the desired flow rate, which can optionally include a control device for receiving information and controlling the operation of the pump of the blood pumping system. At a minimum, the control system can be manually actuated to adjust speed of the motor. Alternately, an automatic (i.e. "smart") control system can be used. Optionally, the control system includes sensors that can be located in the pump, the conduits, or in the vascular system of the patient. The control device can measure the rotational speed of the motor based on the zero-crossings of the back-emf waveform. These zero crossings indicate magnetic pole reversals of the rotor. The speed of the motor is controlled by pulse width modulation (PWM) of the input voltage, and torque is controlled by PWM of the input current. The control device also monitors other state variables of the pump motor, such as current and voltage, from which both the flow rate through the blood pumping system and the wall shear stress in the peripheral blood vessel can be estimated and controlled. The control device preferably includes a memory, a processor for controlling the pump motor speed, analyzing the information coming from the motor drive electronics and optional sensors, and executing instructions encoded on a computer-readable medium. The blood pump system includes a cable for electrically connecting the control device to the pump and optional sensors. The blood pump system also includes a power source that, in various embodiments, may be integrated into the control device. In various embodiments, the power source for the blood pump system may be mobile (e.g. a rechargeable battery or fuel cell) or stationary (e.g. a power base unit connected to AC mains).

The control system may acquire information from various sources. The motor drive electronics within the control device can measure at least one of the motor speed, input power, or current required to operate the pump. In other embodiments, the control system includes sensors in the blood pump or conduits that measure at least one of a blood velocity, a blood flow rate, a resistance to blood flow in a peripheral blood vessel, a blood pressure, a pulsatility index, and combinations thereof. In other embodiments, the control system includes sensors in the vascular system of the patient that measure at least one of a blood velocity, a blood flow rate, a blood pressure, a pulsatility index, a vessel diameter, and combinations thereof.

In various embodiments, the control system may estimate and maintain a desired and elevated level of wall shear stress in a target vessel or a donating artery or vein, using the information from the control device and/or sensors, such as a motor speed, motor input power, pump flow rate, pump pressure head, pressure near the junction of the outflow conduit, and the target vessel, pressure drop across a blood vessel, and combinations thereof. For the purpose of this application, "target vessel", "target blood vessel", "target vein", or "target artery" refers to a specific segment of an artery or a vein that is intended to achieve a persistently increased overall diameter and lumen diameter when a pump-conduit assembly is implanted, configured, and operated in such a manner as to result in the persistent increase in the overall diameter and lumen diameter.

Various control system methods may be used to automatically control the operation of the blood pump system. In one embodiment, a method of determining and controlling a wall shear stress in a blood vessel includes the steps of measuring a blood viscosity, measuring a blood flow rate in a blood pump system or the blood vessel, and measuring a radius of the blood vessel. The steps also include determining the wall shear stress in the blood vessel from the measured blood viscosity, the measured flow rate, and the radius of the blood vessel, comparing the determined wall shear stress to a predetermined reference value, and adjusting a blood pump speed when the determined wall shear stress does not approximate the predetermined reference value. The steps are repeated until the determined wall shear stress approximates the predetermined reference value.

In another embodiment, a method of computing and controlling a wall shear stress in a blood vessel includes the steps of estimating a blood viscosity, measuring a blood flow rate in a blood pump system or the blood vessel, and measuring a radius of the blood vessel. The steps also include determining the wall shear stress from the estimated blood viscosity, the measured blood flow rate, and the radius of the blood vessel, comparing the determined wall shear stress with a predetermined reference value, and adjusting a blood pump speed when the determined wall shear stress does not approximate the predetermined reference value. The steps are repeated until the determined wall shear stress approximates the predetermined reference value.

In one embodiment, a method of estimating and controlling a wall shear stress in a blood vessel includes the steps of estimating a blood viscosity, measuring at least one motor state variable of a blood pump system selected from a voltage, a current, or a pump speed, and estimating a blood flow rate in the blood pump system. The steps also include measuring a pressure in the blood vessel, determining a vascular resistance of the blood vessel from the estimated blood flow rate and the measured pressure in the blood vessel, estimating a radius of the blood vessel. The steps further include determining the wall shear stress from the estimated blood viscosity, the estimated blood flow rate, and the radius of the blood vessel, comparing the determined wall shear stress with a predetermined reference value, and adjusting the pump speed when the determined wall shear stress does not approximate the predetermined reference value. The steps are repeated until the determined wall shear stress approximates the predetermined reference value.

In another embodiment, a method of estimating and controlling a wall shear stress in a blood vessel using a blood pump system includes the steps of estimating a blood viscosity, measuring at least one motor state variable of the blood pump system selected from a voltage, a current, or a pump speed, and estimating a blood flow rate and a pressure head in the blood pump system. The steps also include calculating a vascular resistance of the blood vessel from the estimated blood flow rate and the estimated pressure head, estimating a radius of the blood vessel, and determining the wall shear stress from the estimated blood viscosity, the estimated blood flow rate, and the radius of the blood vessel. The steps further include comparing the determined wall shear stress with a predetermined reference value and adjusting the pump speed when the determined wall shear stress does not approximate the predetermined reference value. The steps are repeated the determined wall shear stress approximates the predetermined reference value.

In one embodiment, a method of estimating and controlling a wall shear stress in a blood vessel using a blood pump system includes the steps of estimating at least one member selected from a group consisting of a blood viscosity, a blood flow rate, a pressure head in the blood pump system, and a radius of the blood vessel, measuring at least one motor state variable of the blood pump system selected from a group consisting of a voltage, a current, and a pump speed, and determining the wall shear stress in the blood vessel. The steps also include comparing the determined wall shear stress with a predetermined reference value and adjusting the pump speed when the determined wall shear stress does not approximate the predetermined reference value. The steps are repeated until the determined wall shear stress approximates the predetermined reference value.

In yet another embodiment, a sensorless method to avoid a collapse of a blood vessel fluidly connected to a blood pump system upon detecting an imminence of the collapse at an inlet of the blood pump system includes the steps of measuring a blood pump motor current and continually determining a spectral analysis representation of the blood pump motor current in a form of a Fourier series. The steps also include providing a detection indication when an amplitude of the second harmonic term of the Fourier series exceeds a reference value and decrementing a pump speed when the amplitude of the second harmonic term of the Fourier series exceeds the reference value. The steps are repeated until the amplitude of the second harmonic term falls below the reference value.

In various other embodiments, the systems and methods disclosed herein may be encoded on computer-readable media that may be executed by a any reference values or predetermined standards used by the systems and methods may be stored in a database or other suitable storage medium.

BRIEF DESCRIPTION OF FIGURES

FIG. 13 is a plan view of the inlet cap and impeller casing.

FIGS. 14-16 are, respectively, cross sectional elevations taken along section lines 14-14, 15-15, and 16-16 in FIG. 13.

FIGS. 19A and 19B are the same respective views as FIGS. 18A and 18B, except of another embodiment.

FIGS. 24A and 24B are, respectively, plan and side elevation views of another embodiment of the inlet cap and inlet channel similar to that described in FIG. 21, except further including an arcuate wedged portion.

FIGS. 27A-27D are perspective views of the connection between the pump and conduits according to one embodiment.

DETAILED DESCRIPTION OF THE INVENTION

Figure 1:
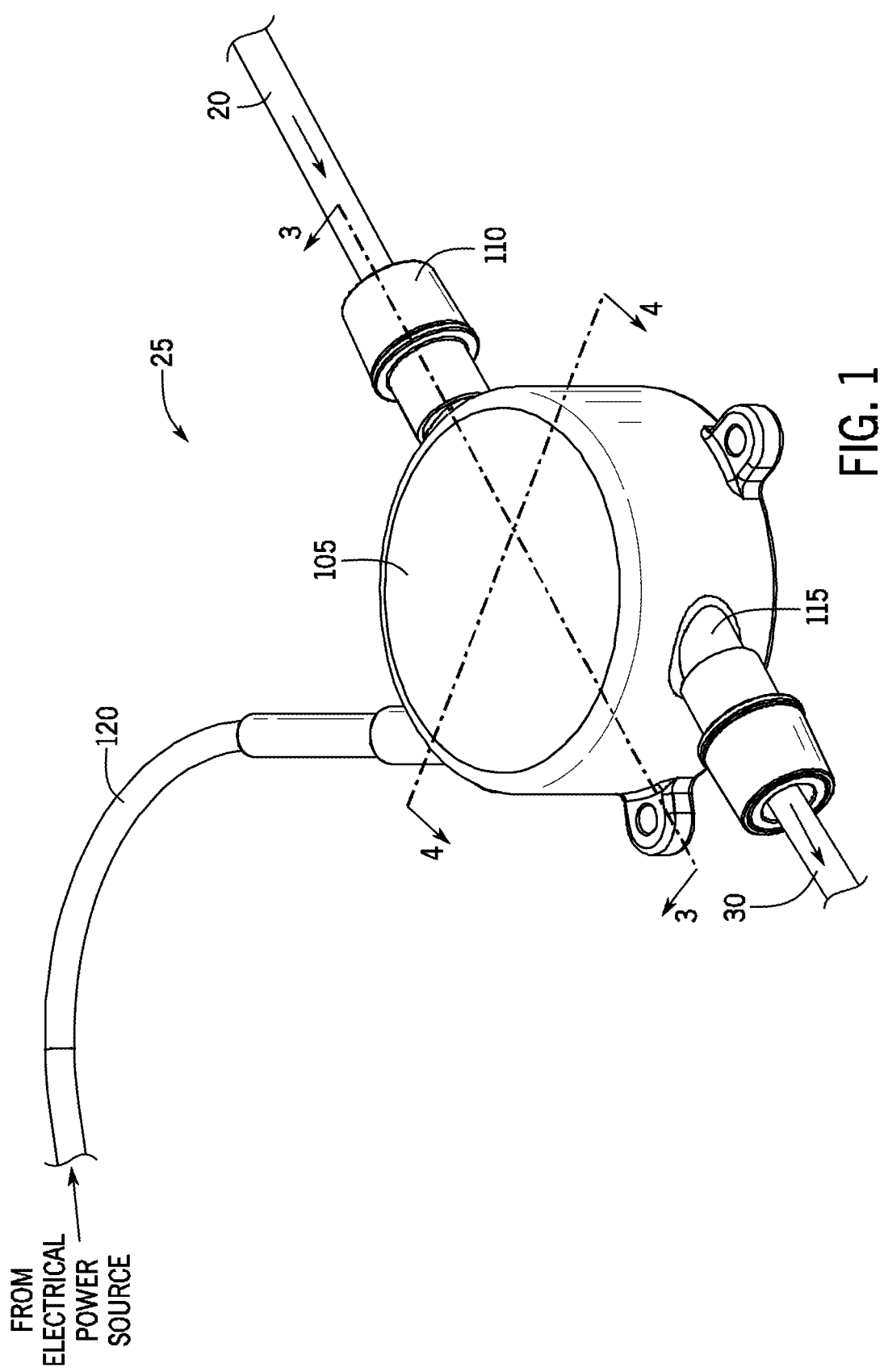
FIG. 1 is an isometric view of the pump.

The systems and components of the present application relate to a blood pump system. More specifically, in various embodiments, the present application relates to a blood pump designed and dimensioned to discharge blood into a target vessel or withdraw blood from a target vessel in such a way and for such a period of time that the diameter of the target vessel (vein or artery) is persistently increased. Even more specifically, the present application relates to a rotary blood pump system configured to persistently increase the mean and/or peak blood velocity and mean and/or peak wall shear stress in selected segments of veins or arteries for a period of time sufficient to persistently increase the overall diameter and the lumen diameter of selected segments of veins or arteries. The term "persistent increase" or "persistent dilation" when used to describe dilation or an increase in the overall diameter and lumen diameter of an artery or vein, is used herein to mean that even if the pump is turned off, an increase in the overall diameter or lumen diameter of a vessel can still be demonstrated when compared to the overall diameter or lumen diameter of the vessel prior to the period of blood pumping. That is, the overall diameter or lumen diameter of the vessel has become larger independent of the pressure generated by the pump. The blood pump system may therefore be useful to certain patients, including CKD patients in need of a vascular access site for hemodialysis. The blood pump system can include a rotary blood pump, one or more blood-carrying conduits, a control system, and a power source. The blood pump system withdraws blood from one location in the vascular system and discharges blood to another location in the vascular system. During operation, such a blood pump system may persistently increase mean and/or peak blood velocity and mean and/or peak WSS in a target blood vessel to a level and for a period of time sufficient to persistently increase the overall diameter and lumen diameter of the target blood vessel. The system functions in configurations where blood is withdrawn from the target blood vessel or in configurations where blood is discharged into the target blood vessel. Further, the system can be used simultaneously to increase the size of the donating and receiving vessels.

The optional blood-carrying conduits can include an inflow conduit to carry blood from a location in the vascular system (such as a donating vein, a donating artery, or the right atrium) to the blood pump and an outflow conduit to carry blood from the blood pump to a location in the vascular system (such as an accepting peripheral vein or artery, or an accepting location such as the right atrium). The blood pump system also includes a control system. A preferred control system is designed to collect information on the operating parameters and performance of the blood pump system, and changes in the vascular system, such as changes in the diameter of a donating artery, donating vein, accepting artery, or accepting vein of a patient. The blood pump system is primarily configured to pump a sufficient amount of blood such that a desired mean and/or peak wall shear stress (WSS) is achieved within a blood vessel segment (the "target blood vessel" or "target vessel") and for a sufficient period of time such that the permanent or persistent overall diameter and lumen diameter of the blood vessel segment is increased. The mean WSS can be calculated using the measured, estimated, or assumed vessel diameter and the measured, estimated, or assumed average blood flow rate through the blood pump system.

The diameter of blood vessels can be determined by measuring the diameter of the void within the center of the blood vessel. For the purpose of this application, this measurement is referred to as "lumen diameter". The diameter of blood vessels can be determined by measuring the diameter in a manner that includes the void within the center of the blood vessel and the wall of the blood vessel. For the purpose of this application, this measurement is referred to as "overall diameter". The invention relates to simultaneously and persistently increasing the overall diameter and lumen diameter of a peripheral vein by moving blood (preferably with low pulsatility) into the peripheral accepting vein, thereby increasing the speed of the blood in the peripheral accepting vein and increasing the WSS on the endothelium of the peripheral accepting vein. Systems and methods are described wherein the speed of the blood in a peripheral accepting vein and the WSS on the endothelium of the peripheral accepting vein is increased by using a pump. Systems and methods are also described that withdraw or "pull" blood such that the speed of the blood and the WSS is increased in the donating vessel, either an artery or a vein. Preferably, the pump actively discharges blood into the peripheral accepting vein, wherein the pumped blood has reduced pulsatility, such as when the pulse pressure is lower than blood in a peripheral artery.

To begin a detailed discussion of the blood pump 25 of the system 10, reference is made to FIG. 1, which is an isometric view of the blood pump 25. In one embodiment, the blood pump 25 is a miniaturized centrifugal pump having a magnetic drive wherein the impeller of the pump is rotationally driven by rotating magnetic fields. For example, the rotating magnetic fields may be generated by energizing a number of electromagnets in a particular sequence. In another example, the rotating magnetic fields may be generated by rotating a number of permanent magnets or energized electromagnets. The pump can have a diameter approximately equal to that of a coin on the order of, for example, a United States quarter, a United States half dollar, or a larger coin. As shown in FIG. 1, the blood pump 25 includes a body 105, an inlet 110, an outlet 115, and a power cable 120. The power cable 120 connects the blood pump 25 to the control device 21 of a control system 14 and power source. The power source can be part of the control device 21 or separate. The power cable allows for communication between the control device 21 and the motor of the blood pump 25. The cable can also be used to transfer power from a power source to the motor or pump. More particularly, the power cable 120 connects the electrical components of the magnetic drive inside the body 105 to an electrical power source (e.g., a battery).

The inlet 110 is capable of being fluidly coupled to the inflow conduit 20 via a coupling arrangement (e.g., a barbed-end, a flange, and a locking collar). The inlet 110 provides a fluid pathway into the intake region (i.e. center) of the pump impeller. The intake region of the impeller can be of a variety of constructions so long as blood is received out of the outlet at a speed greater than the intake. The outlet 115 is capable of being fluidly coupled to the outflow conduit 30 via a coupling arrangement similar to the inlet (e.g., a barbed-end, a flange, and a locking collar). The outlet 115 provides a fluid pathway from the outlet region (i.e. periphery) of the pump impeller.

Figure 2:
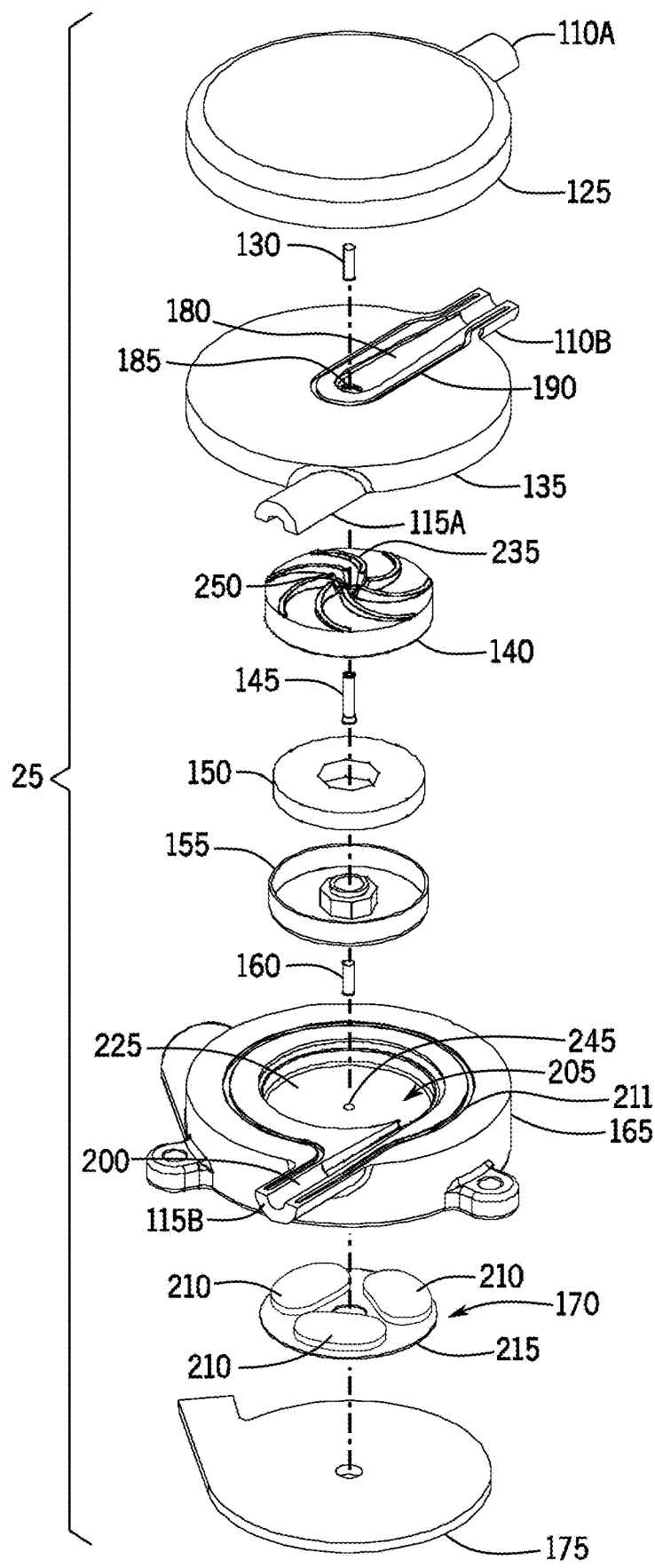
FIG. 2 is an exploded isometric view of the pump showing its components contained in the body identified in FIG. 1.

As illustrated in FIG. 2, which is an exploded isometric view of the blood pump 25 showing its components contained in the body 105 identified in FIG. 1, the blood pump 25 includes an inlet cap 125, a top bearing pin 130, a top impeller casing 135, an impeller 140, an impeller pivot 145, a magnet assembly 150, a magnet enclosure 155, a bottom bearing pin 160, a bottom impeller casing 165, an electrical coil assembly 170, and a coil assembly enclosure lid 175. The inlet cap 125 and top impeller casing 135 each include approximately half of the inlet 110.

Figure 3A:
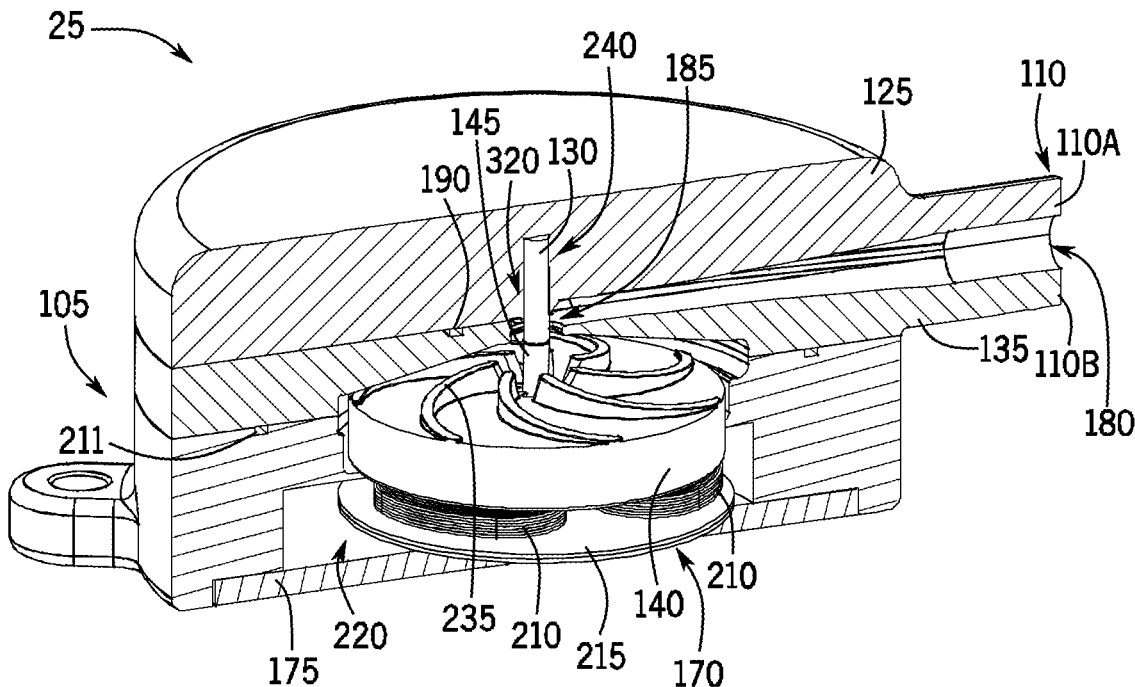
FIGS. 3A and 3B are, respectively, partial and full cross sectional elevations of the pump as taken along section line 3-3 in FIG. 1.
Figure 3B:
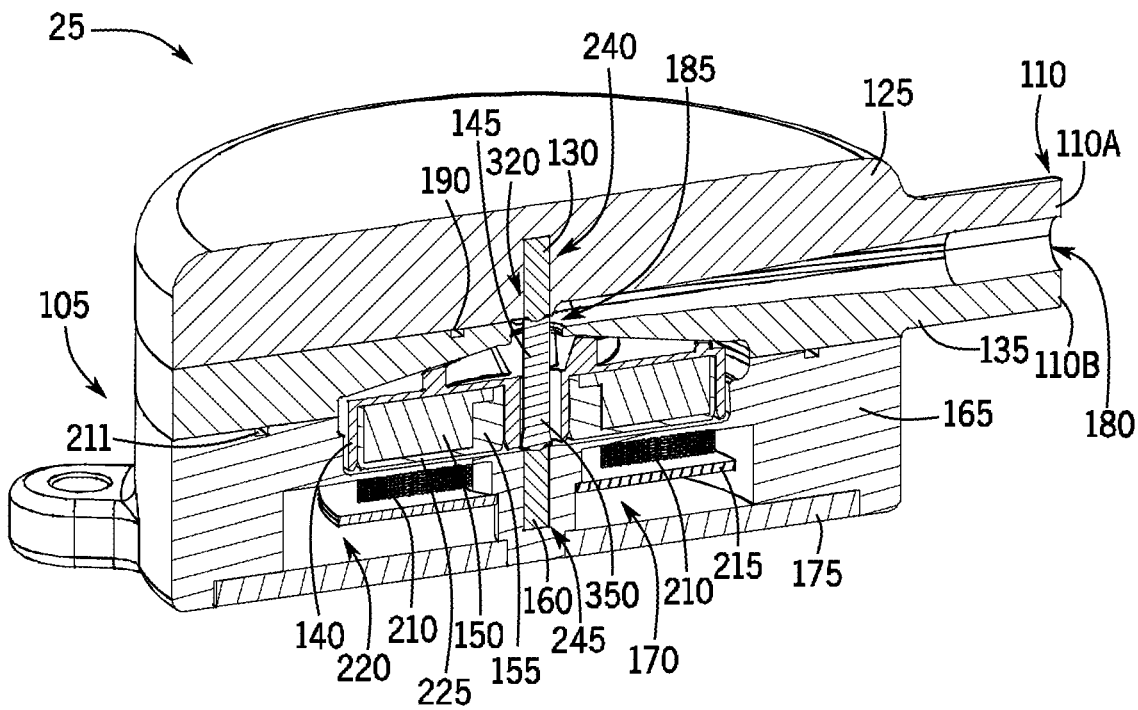

As shown in FIGS. 3A and 3B, which are, respectively, partial and full cross sectional elevations of the blood pump 25 as taken along section line 3-3 in FIG. 1, the components mentioned with respect to FIG. 2 generally sandwich together to form the pump. For example, as can be understood from FIGS. 2-3A, the inlet cap 125 and top impeller casing 135 respectively include a top horizontally extending inlet portion 110A and a bottom horizontally extending inlet portion 110B. Typically, the inlet and outlet are opposed and located in different planes. When the inlet cap 125 and top impeller casing 135 are sandwiched together, they define an inlet fluid channel 180 leading through the inlet 110 to the impeller inlet orifice 185. The inlet cap 125 and top impeller casing 135 respectively define approximately a top half and a bottom half of the channel 180. A seal groove 190 is defined in the top impeller casing 135 adjacent to the border of the channel 180 and is adapted to receive a resilient fluid seal member for creating a fluid tight seal between the inlet cap 125 and top impeller casing 135.

Figure 4A:
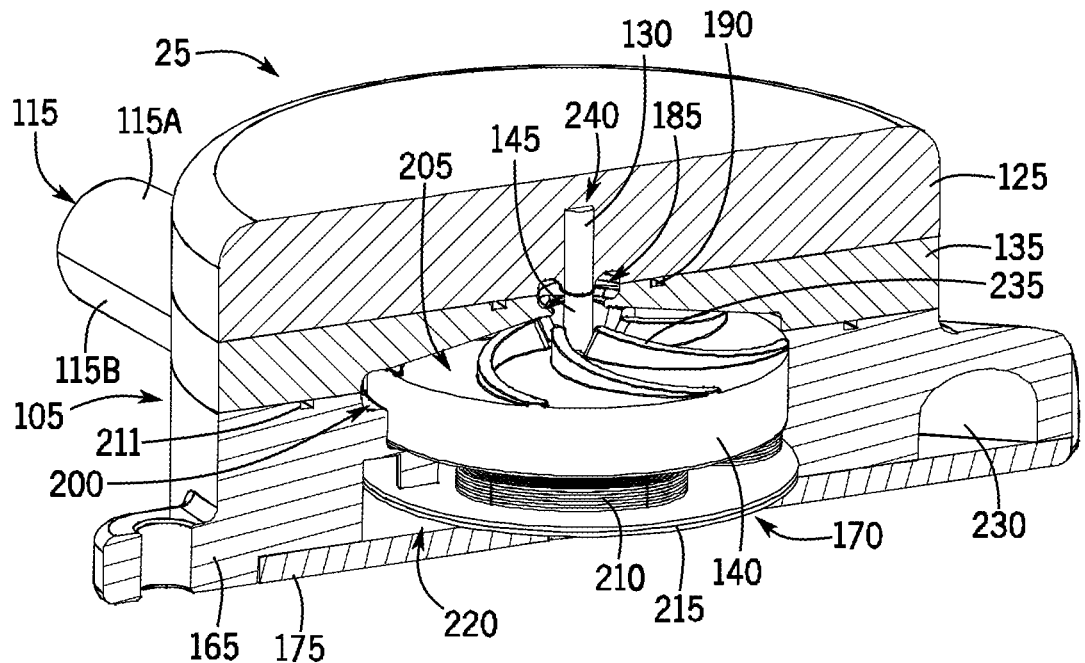
FIGS. 4A and 4B are, respectively, partial and full cross sectional elevations of the pump as taken along section line 4-4 in FIG. 1.
Figure 4B:
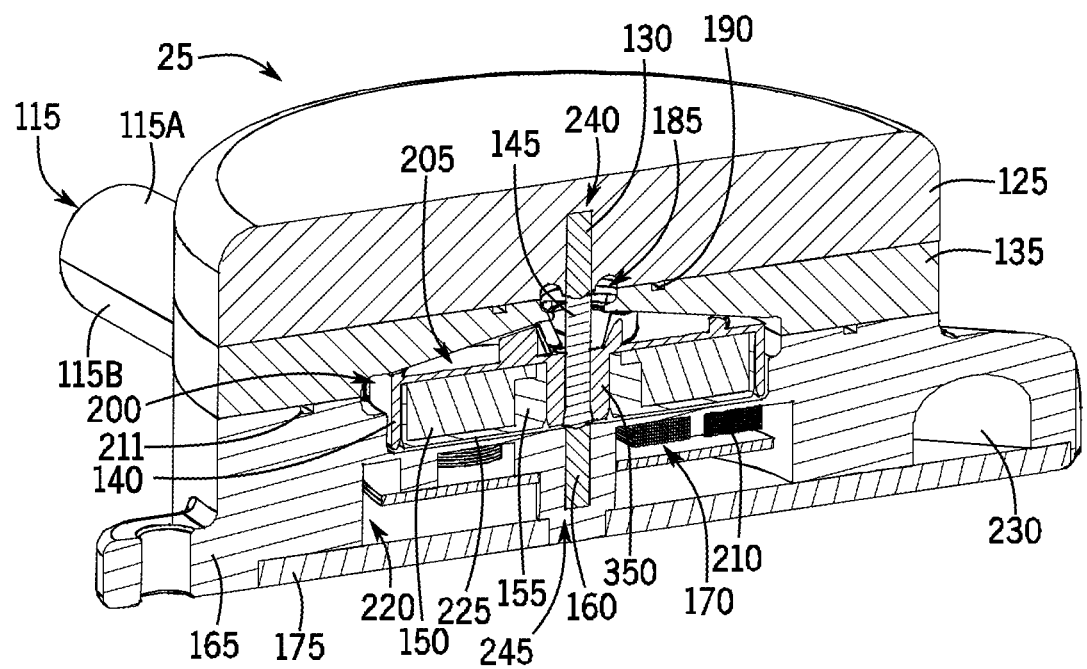

FIGS. 4A and 4B are, respectively, partial and full cross sectional elevations of the blood pump 25 as taken along section line 4-4 in FIG. 1. As can be understood from FIGS.

2, 4A, and 4B, the top impeller casing 135 and bottom impeller casing 165 respectively include a top horizontally extending outlet portion 115A and a bottom horizontally extending outlet portion 115B. When top impeller casing 135 and bottom impeller casing 165 are sandwiched together, they define an outlet fluid channel 200 (i.e. volute) leading from the impeller chamber 205 to the outlet 115. The top impeller casing 135 and bottom impeller casing 165 respectively define approximately a top half and a bottom half of the channel 200. A seal groove 211 is defined in the bottom impeller casing 165 adjacent to the border of the channel 200 and impeller chamber 205 and is adapted to receive a resilient fluid seal member for creating a fluid tight seal between the top impeller casing 135 and bottom impeller casing 165.

As indicated in FIGS. 2-4B, the magnets 150 are a plurality of magnets in the form of a ring or disk. The magnets 150 are located in the volume of the magnet enclosure 155 and the volume of the impeller 140. The magnet enclosure is received in the impeller. The magnet enclosure 155 and the impeller 140 respectively form the bottom and top portions of the volume in which the magnets 150 are located. The magnet enclosure, magnets, and impeller are coupled together in a fixed integral assembly that rotates as a unit within the impeller chamber 205. Alternative constructions can be used that cause rotation of the impeller.

As illustrated in FIGS. 2-4B, the electrical coil assembly 170 is a plurality of electrical coils 210 arranged in a circular arrangement on the lower impeller casing and optionally capped by a support disk 215. The electrical coil assembly 170 is fixed within the coil chamber 220 defined in the bottom impeller casing 165 and capped by the coil enclosure lid 175. An internal floor structure 225 separates the impeller chamber 205 from the coil chamber 220. The electrical cable 120 (see FIG. 1) extends through passage 230 in the bottom impeller casing 165 to the coil chamber 220 and the coils 210. Electrical power supplied to the coils 210 via the electrical cable 120 generates rotating magnetic fields, which act on the magnets 150 to cause the magnets, and the impeller 140 coupled to the magnets to rotate. The impeller rotation causes the impeller blades 235 to act upon the fluid (e.g., blood) present in the impeller chamber, resulting in momentum being transferred to the fluid that is recovered as a pressure increase in the outlet fluid channel 200. The fluid is thus drawn into the inlet 110 at low pressure and discharged from the outlet 115 at a higher pressure.

Figure 5A:
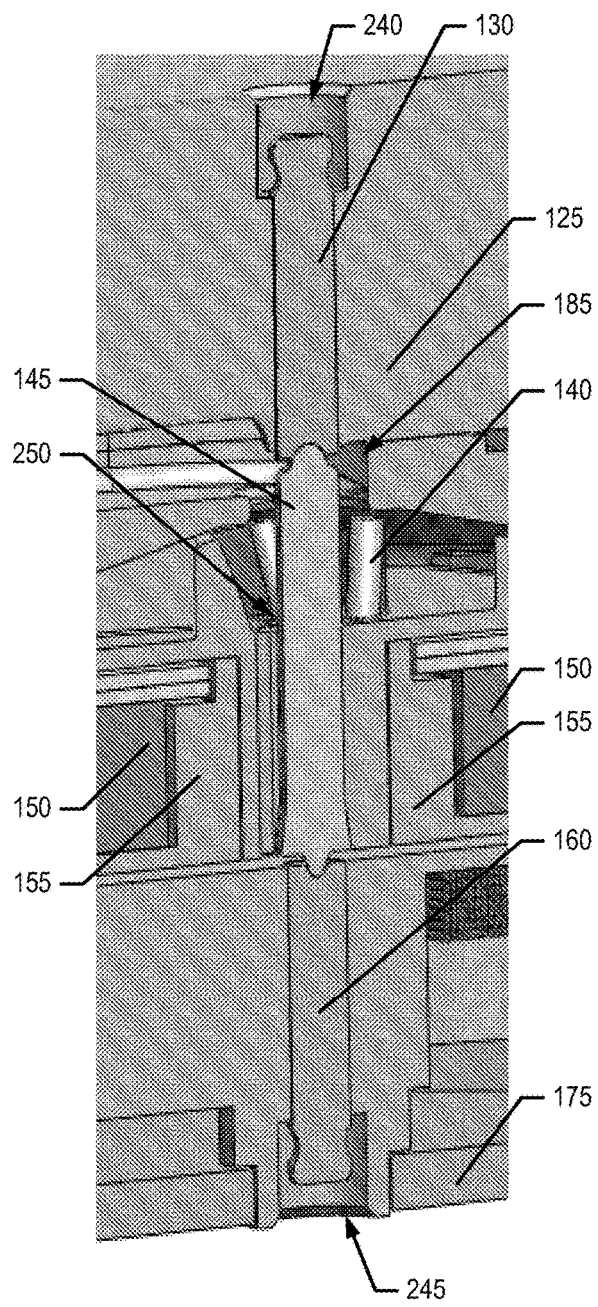
FIGS. 5A-B are enlarged views of the pivot axis area of FIGS. 3B and 4B.
Figure 5B:
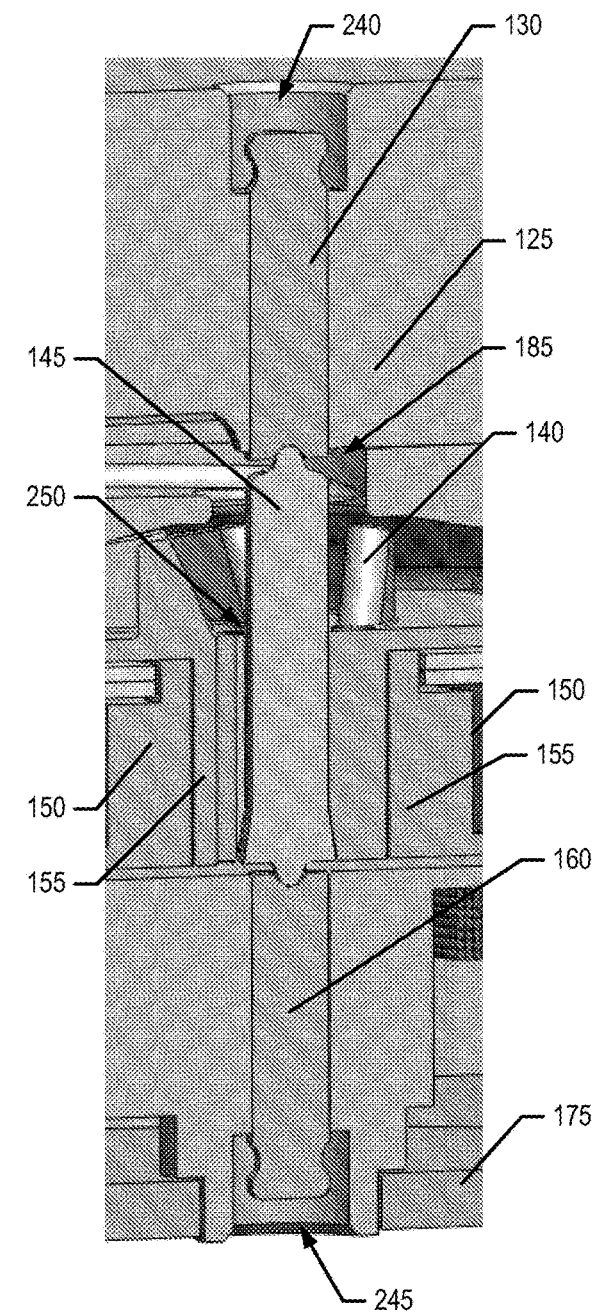

As shown in FIGS. 3A-4B, the pivot axis for the impeller 140, magnets 150, and enclosure 155 is the impeller pivot 145. As depicted in FIGS. 5A-B, the impeller pivot 145 is pivotally supported (i.e. restrained in all degrees of freedom except rotation about a single axis) via a top bearing pin 130 and a bottom bearing pin 160. The top bearing pin 130 is received and fixed in a cylindrical recess 240 in the inlet cap 125, while the bottom bearing pin 160 is received and fixed in a cylindrical recess 245 in the bottom impeller casing 165. The impeller pivot 145 extends through and is fixed to a center cylindrical opening 250 in the impeller 140.

In one embodiment of the impeller assembly, the impeller pivot 145, the top bearing pin 130, and the bottom bearing pin 160 are formed from high purity alumina, such as CoorsTek® AD-998. In another embodiment of the impeller assembly, the impeller pivot 145, the top bearing pin 130, and the bottom bearing pin 160 are formed from silicon carbide toughened alumina, such as Greenleaf® WG-300. In both embodiments, the dimensions of the impeller pivot 145, the top bearing pin 130, and the bottom bearing pin 160 are designed to limit the contact stresses to permissible levels for high purity alumina or silicon carbide toughened alumina, respectively, in view of peak thrust loads generated by hydrostatic forces and shock loads. In another embodiment of the impeller assembly, the impeller pivot 145 is formed from silicon carbide toughened alumina, such as Greenleaf® WG-300 or from high purity alumina, such as CoorsTek® AD-998, while the top bearing pin 130, the bottom bearing pin 160, or both are formed from ultrahigh molecular weight polyethylene. Additionally, the geometry of each component of the impeller assembly has been selected to limit fatigue and wear in order to satisfy the safety and durability requirements of the system 10.

Figure 6A:
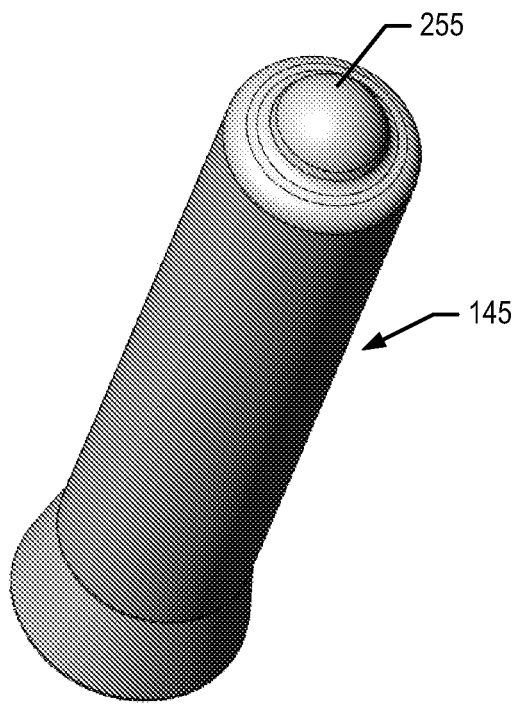
FIGS. 6A-B, respectively, are top and bottom isometric views of the impeller pivot.
Figure 6B:
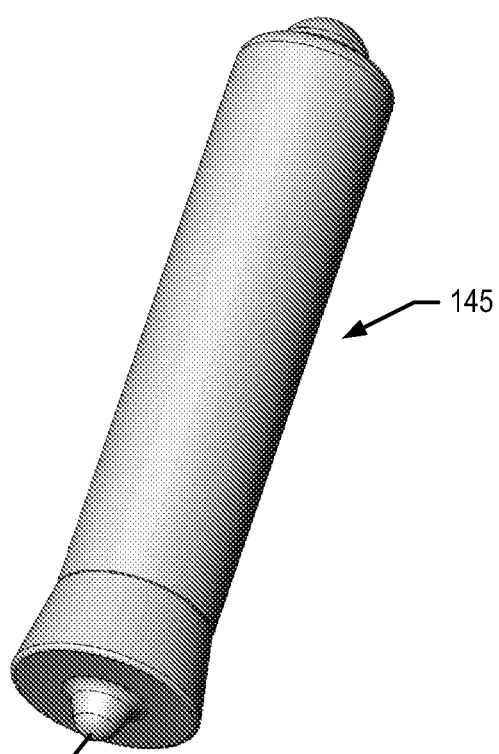
Figure 7A:
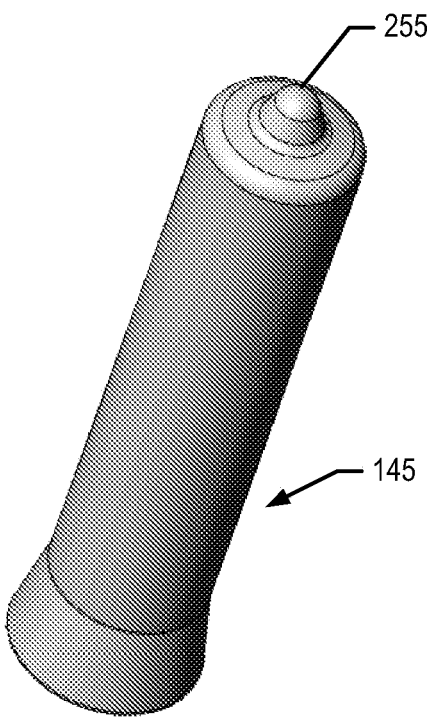
FIGS. 7A-B, respectively, are top and bottom isometric views of the impeller pivot.
Figure 7B:
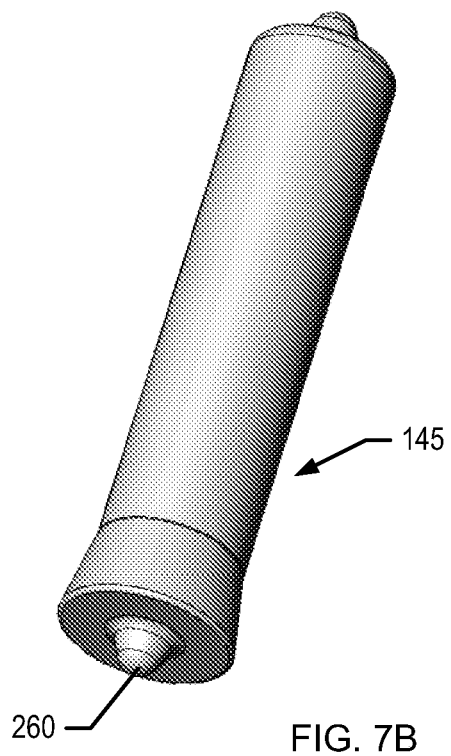
Figure 8A:
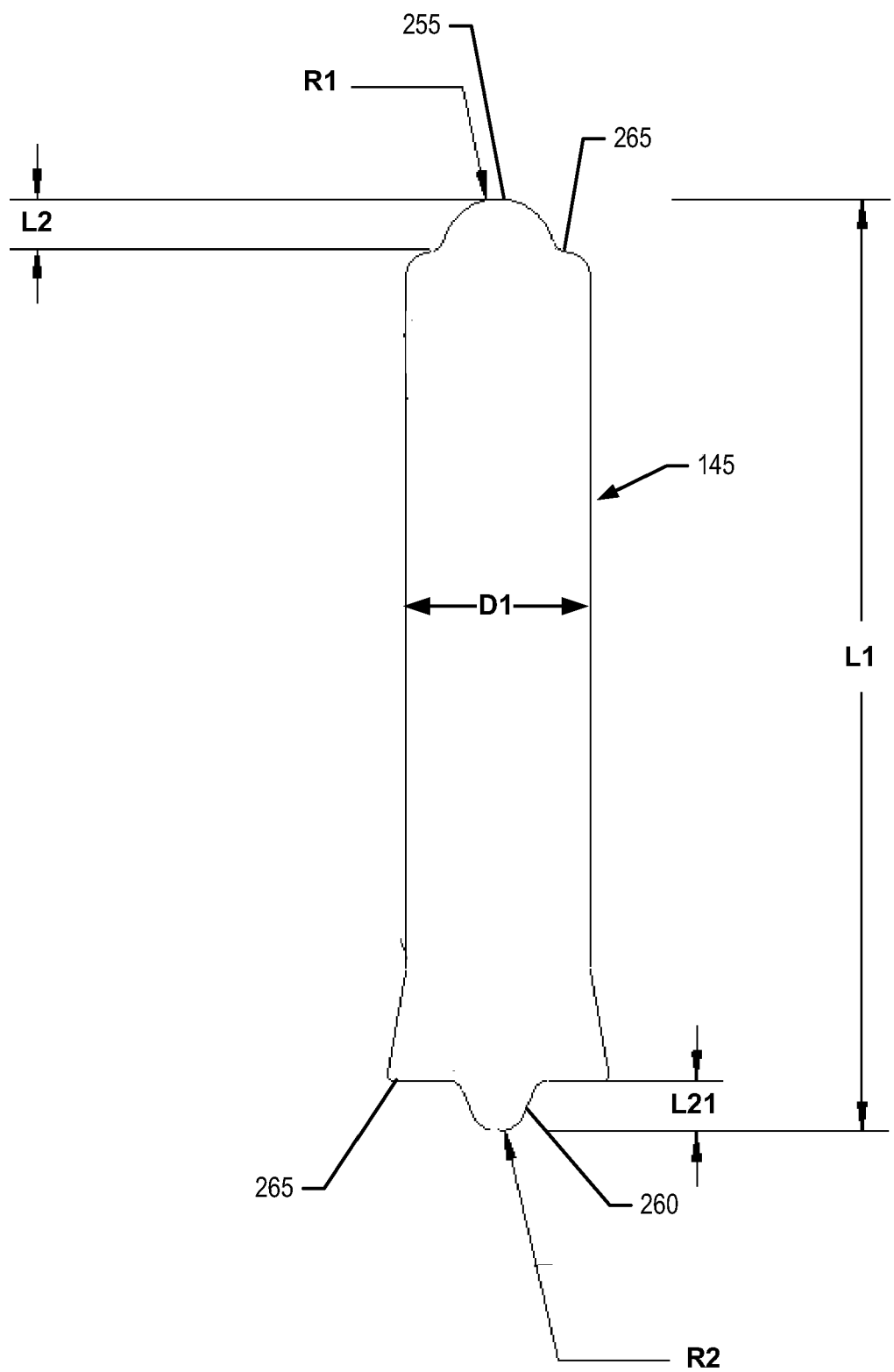
FIGS. 8A-B are side elevation views of embodiments of the impeller pivot.
Figure 8B:
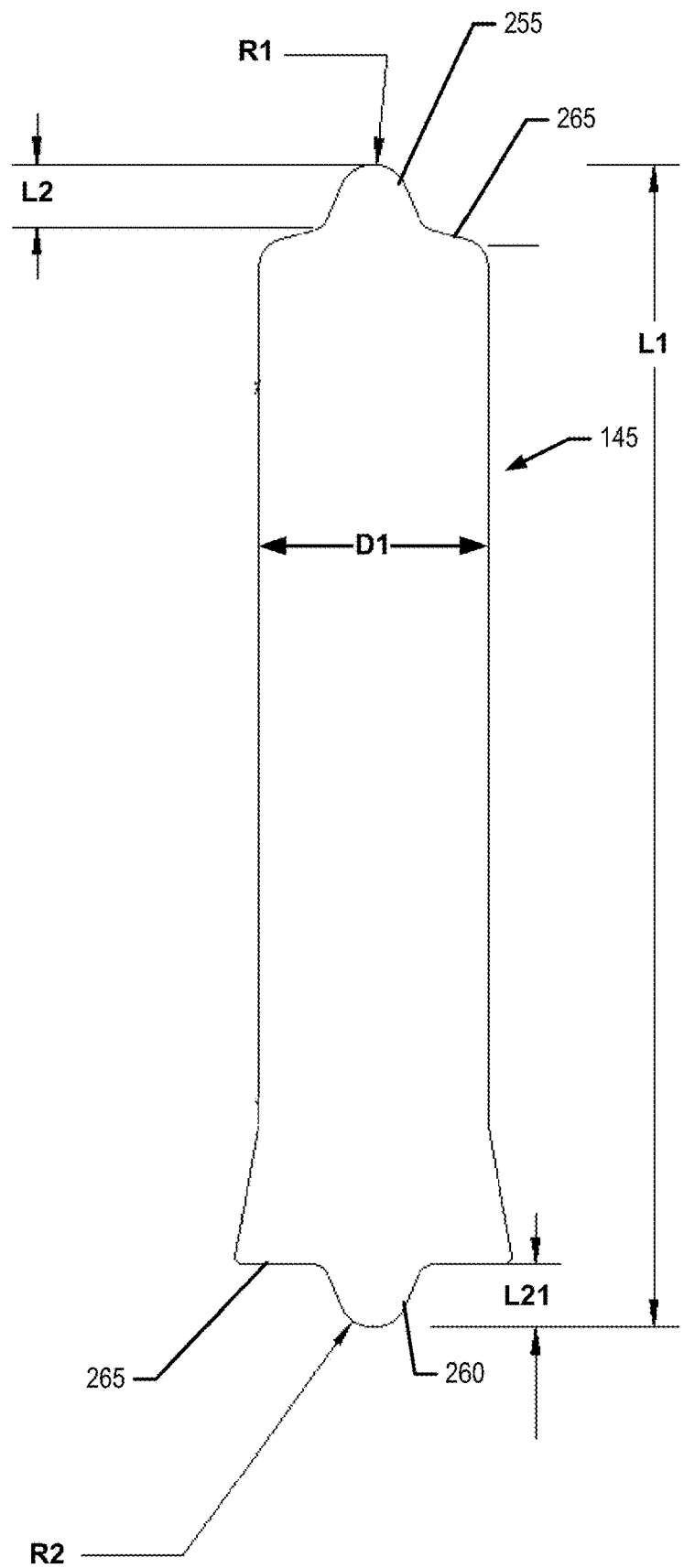

As illustrated in FIGS. 6A-7B, the impeller pivot includes an upper hemispherical convex bearing surface 255 and a bottom hemispherical convex bearing surface 260. As indicated in FIGS. 6A, 6B, and 8A, one embodiment of the impeller pivot has an overall length L1 of approximately 10.15 mm, plus or minus 0.05 mm, and a pivot diameter D1 of approximately 2 mm, plus or minus approximately 0.01 mm. The upper bearing surface 255 has a radius R1 of approximately 0.61 mm, plus or minus 0.02 mm and extends a length L2 past an adjacent lip 265 by approximately 0.55 mm, plus or minus 0.02 mm. The lower bearing surface 260 has a radius R2 of approximately 0.31 mm, plus or minus 0.02 mm and extends a length L21 past an adjacent lip 265 by approximately 0.55 mm, plus or minus 0.02 mm. Similarly, an alternate embodiment of the impeller pivot 145, as indicated in FIGS. 7A, 7B, and 8B, has an overall length L1 of approximately 10.15 mm, plus or minus 0.05 mm, and a pivot diameter D1 of approximately 2 mm, plus or minus approximately 0.01 mm. The upper bearing surface 255 has a radius R1 of approximately 0.31 mm, plus or minus 0.02 mm and extends a length L2 past an adjacent lip 265 by approximately 0.55 mm, plus or minus 0.02 mm. The lower bearing surface 260 has a radius R2 of approximately 0.31 mm, plus or minus 0.02 mm and extends a length L21 past an adjacent lip 265 by approximately 0.55 mm, plus or minus 0.02 mm. Other sizes and dimensions may be used depending upon the size and performance requirements of the pump. The sizes are such that the resultant pump can be used in a patient to increase the diameter of a vessel.

Figure 9A:
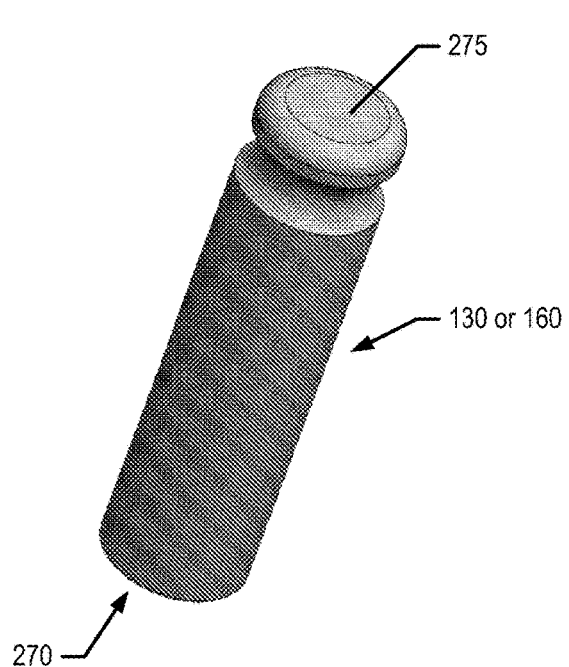
FIGS. 9A-B are, respectively, opposite end views of a representative bearing pin used on either end of the impeller pivot to support and allow rotation of the impeller pivot.
Figure 9B:
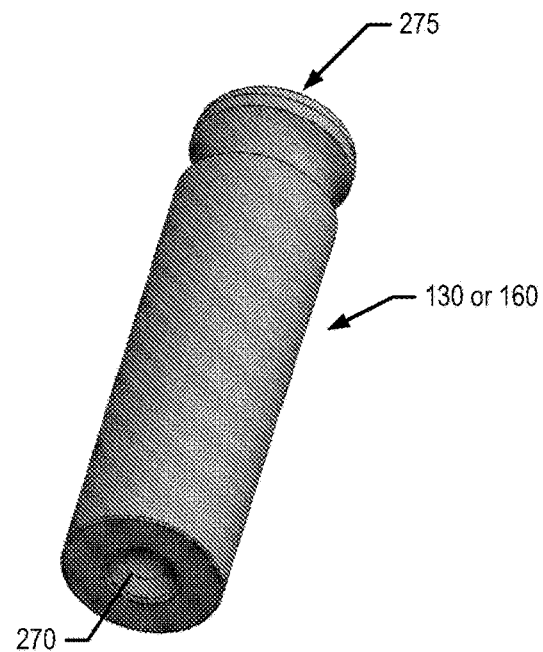
Figure 10:
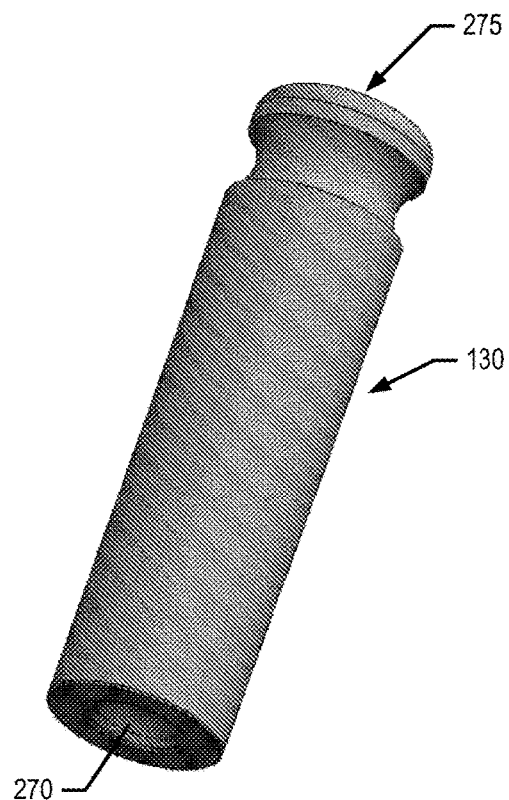
FIG. 10 is a view of an embodiment of the top bearing pin.

As can be understood from FIGS. 5A and 5B, the upper bearings pin 130 and bottom bearing pin 160 generally have the same configuration, but are oppositely oriented. As depicted in FIGS. 9A-B, the top bearing pin 130 and the bottom bearing pin 160, have a tea cup or hemispherical concave bearing surface 270 on one end and a generally planar surface 275 on the opposite end. Similarly, FIG. 10 depicts a particular embodiment of the top bearing pin 130, which has a tea cup or hemispherical concave bearing surface 270 on one end and a generally planar surface 275 on the opposite end. In this embodiment, the hemispherical concave bearing surface 270 of the top bearing pin 130 has a larger radius than the concave bearing surface on the bottom bearing pin 160.

Figure 11A:
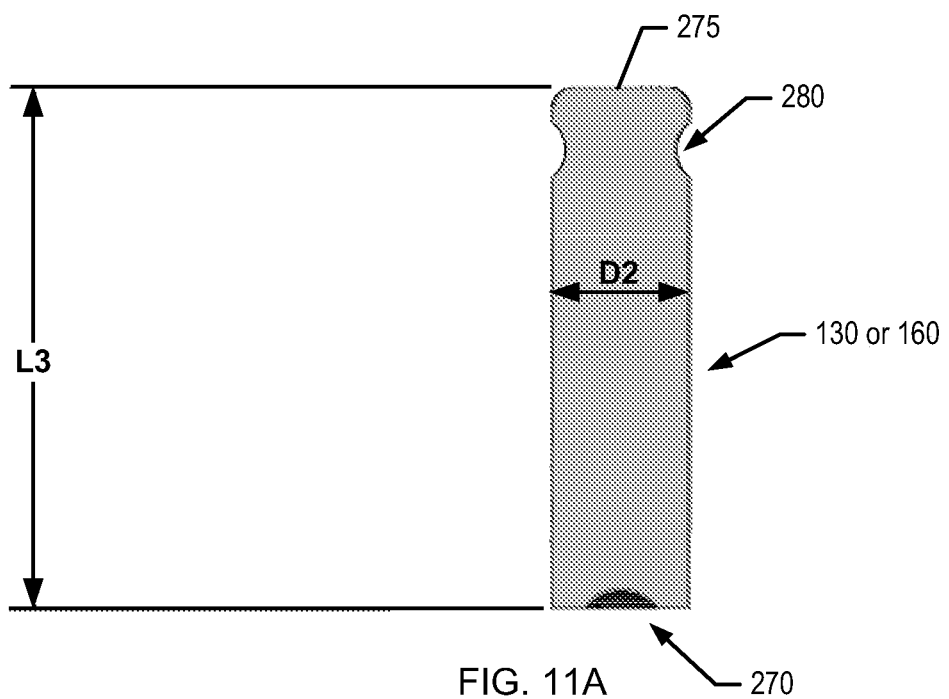
FIGS. 11A-B are side elevation views of embodiments of the representative bearing pin.
Figure 11B:
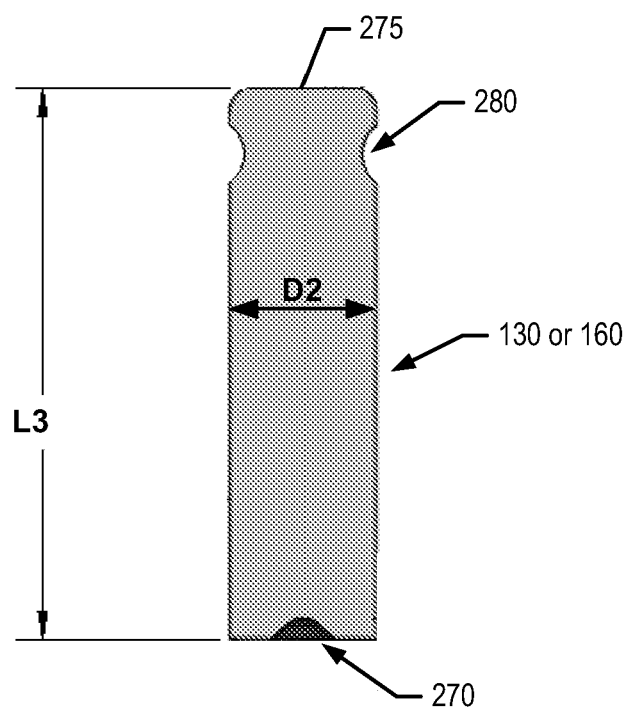

As illustrated in FIG. 11A, one embodiment of the bearing pin 130, 160 has an overall length L3 of approximately 7.5 mm, plus or minus 0.1 mm, a minimum pivot diameter D2 of approximately 2 mm, plus or minus 0.01 mm, and a radius of approximately 0.6 mm at the edge near the bearing surface 270. Near the non-bearing end 275 of the bearing pin 130, 160, a groove 280 extends circumferentially around the pin to provide a mechanical interlock for bonding the bearing pin in place within the blood pump 25. Similarly, an alternate embodiment of the bearing pins 130, 160, as illustrated in FIG. 11B, has an overall length L3 of approximately 7.5 mm, plus or minus 0.1 mm, a minimum pivot diameter D2 of approximately 3 mm, plus or minus 0.01 mm, and a radius of approximately 0.2 mm at the edge near the planar end 275. Near the non-bearing end of the bearing pin 130, 160 there is a groove 280 circumferentially extending around the pivot used to provide a mechanical interlock for bonding the bearing pin in place. Other sizes and dimensions may be used depending upon the size of the pump, the materials of the bearing pin, and the forces acting on the bearing pin.

As can be understood from FIGS. 3B, 4B, and 5A-11B, the convex upper bearing surface 255 of the impeller pivot 145 is rotationally received against the concave bearing surface 270 of the top bearing pin 130, and the convex lower bearing surface 260 of the impeller pivot 145 is rotationally received against the concave bearing surface 270 of the bottom bearing pin 160. Thus, the convex bearing ends 255, 260 of the impeller pivot 145 are pivotally supported by complementary concave bearing surfaces 270 of the top and bottom bearing pins 130 and 160, respectively. Accordingly, the impeller assembly may freely rotate in the impeller chamber 205 on the impeller pivot 145, which is supported end to end with the bearing pins 130 and 160, in a configuration commonly known as a "double pin bearing."

In yet another embodiment of the impeller assembly, the impeller assembly is a composite of the impeller shaft 145, top bearing pin 130, and bottom bearing pin 160. The composite design is beneficial with regard to the simplicity, tolerances, and cost of the machined bearing components. All of these constructions are designed to allow the motor to function in a continuous state for around a day to 1-12 weeks or longer, without breakdown.

Figure 12:
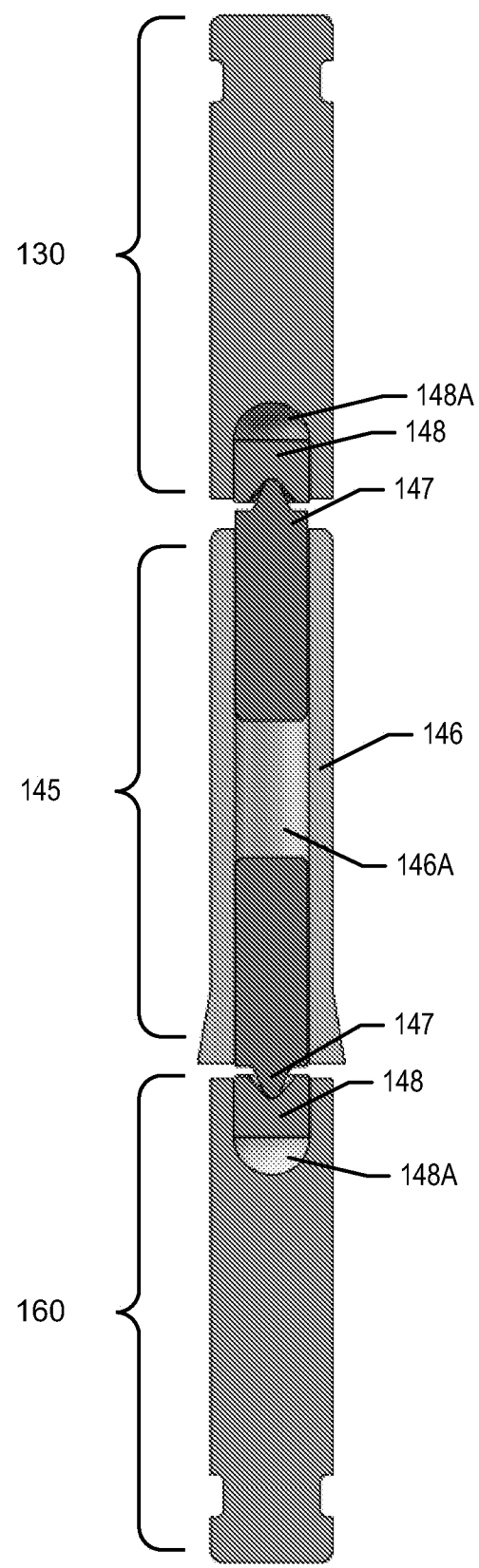
FIG. 12 is a longitudinal cross section of a representative bearing pin assembly.

As illustrated in FIG. 12, the impeller shaft 145 comprises an impeller pivot body 146 and two impeller pivot inserts 147. The impeller pivot body 146 comprises a machinable metal, such as stainless steel, and the impeller pivot inserts 147 comprise a high purity alumina, such as CoorsTek AD-998, or a silicon carbide toughened alumina, such as Greenleaf WG-300. The impeller pivot inserts 147 are affixed to the impeller pivot body 146 by an adhesive and/or an interference fit. Optionally, the chamber 146A may be filled with an adhesive or other potting material that is resistant to compression. The aforementioned composite configuration and materials can be applied to embodiments of both the top bearing pin 130 and bottom bearing pin 160, where the pin inserts 148 engage the impeller pivot inserts 147. Optionally, the chambers 148A for each bearing pin 130 and 160, may be filled with an adhesive or other potting material that is resistant to compression.

The inlet cap 125 and its inlet channel 180 may have a variety of configurations, depending on the embodiment of the blood pump 25. For example, the inlet cap 125 depicted in FIG. 2 is shown as being generally coextensive with the top impeller casing 135. In other embodiments, the inlet cap 125 may be substantially smaller than, and not coextensive with, the top impeller casing 135, as depicted in FIGS. 13-15, which are views of the inlet cap and impeller casing.

As shown in FIGS. 14-16, which are, respectively, cross sectional elevations taken along section lines 14-14, 15-15, and 16-16 in FIG. 13, the inlet 110 is a two part construction having portions 110A and 110B that each form approximately half of the inlet 110 and are respectively part of the inlet cap 125 and top impeller casing 135. Each portion 110A and 110B has defined therein approximately half of the inlet channel 180. As illustrated in FIG. 14, the inlet channel 180 initially has a circular diameter D5 of approximately 4 mm. As indicated in FIG. 15, the inlet channel 180 transitions from a circular cross section to a generally rectangular cross section having a width W5 of approximately 8.4 mm and a height H5 of approximately 1.5 mm. Again, as dimensions change so will the listed measurements.

Figure 17:
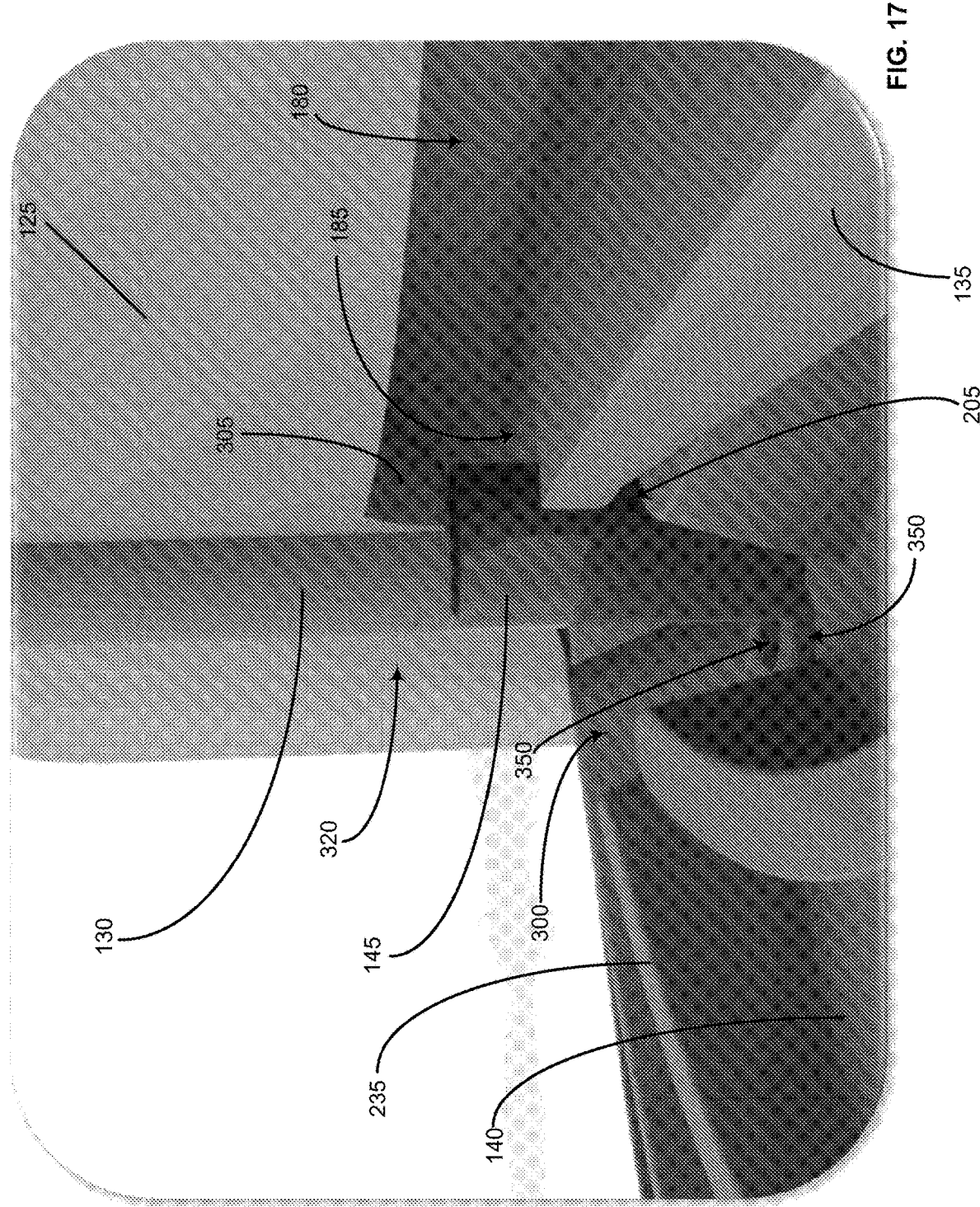
FIG. 17 is an isometric partial cross section of the impeller chamber inlet orifice.

As depicted in FIG. 16, the inlet channel 180 surrounds the impeller chamber inlet orifice 185, which extends around the top bearing 145 received in, and affixed to, the inlet cap 125. As shown in FIG. 17, which is an isometric partial cross section of the impeller chamber inlet orifice 185, the impeller chamber inlet orifice 185 leads to the impeller chamber 205 near the intake region 300 of the impeller 140. The upper bearing end of the impeller pivot 145 extends up through the orifice 185 to pivotally interface with the top bearing pin 130 supported in the inlet cap 125. Impeller blades 235 extend radially outward from the intake region 300 of the impeller 140.

Figure 18B:
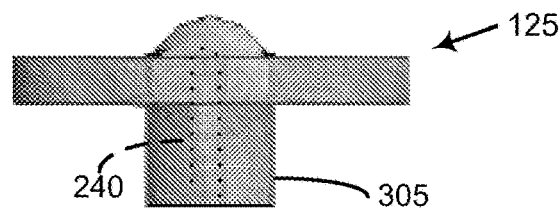
FIGS. 18A and 18B are, respectively, a plan view of the inlet cap portion defining the inlet channel and an end elevation view of the same.
Figure 18A:
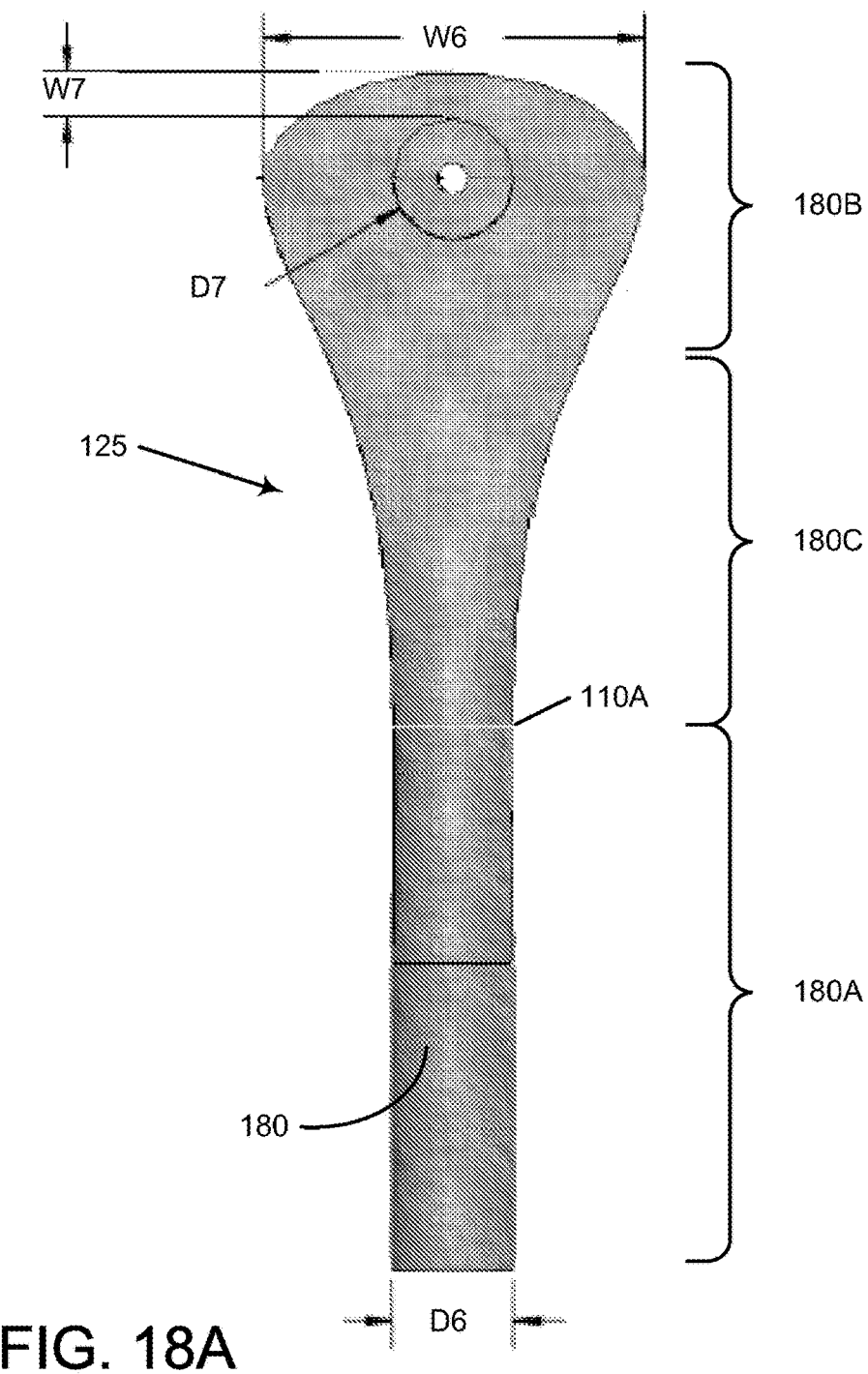

As depicted in FIGS. 18A and 18B, which are, respectively, a plan view of the inlet cap portion 110A defining the inlet channel 180 and an end elevation view of the same, in one embodiment, the inlet channel 180 may be said to have an elliptic configuration. Specifically, a cylindrical channel portion 180A transitions in portion 180C into an elliptical channel portion 180B. A cylindrical island portion or bezel 305 supporting the top bearing pin 130 is generally centered in the elliptical channel portion 180B and includes a cylindrical hole 240 that receives the top bearing pin 130 similar to as illustrated in FIG. 17. In one embodiment, the cylindrical channel portion 180A has a diameter D6 of approximately 4 mm. The elliptical channel portion 180B has a width W6 of approximately 12.4 mm. The distal distance W7 between the wall of the bezel 305 and the distal end of the wall defining the elliptical channel portion 180B is approximately 1.5 mm. In other embodiments, the cylindrical channel portion 180A has a diameter D6 of approximately 5 mm or 6 mm.

As depicted in FIGS. 19A and 19B, which are the same respective views as FIGS. 18A and 18B, except of another embodiment, the inlet channel 180 may be said to have a circular configuration. Specifically, a cylindrical channel portion 180A transitions in portion 180C into a circular channel portion 180B. A cylindrical island portion or bezel 305 supporting the top bearing pin 130 is generally centered in the circular channel portion 180B and includes a cylindrical hole 240 that receives the top bearing pin 130 similar to as illustrated in FIG. 17. In one embodiment, the cylindrical channel portion 180A has a diameter D9 of approximately 3.5 mm to 4.5 mm, preferably 4 mm. The circular channel portion 180B has a width W9 of approximately 11.5 mm to 13 mm, preferably 12.4 mm. The distal distance W10 between the wall of the bezel 305 and the distal end of the wall defining the circular channel portion 180B is approximately 3.5 mm to 4.5 mm, preferably 4.2 mm. In other embodiments, the cylindrical channel portion 180A has a diameter D6 of approximately 5 mm or 6 mm.

Figures 20A, 20B:
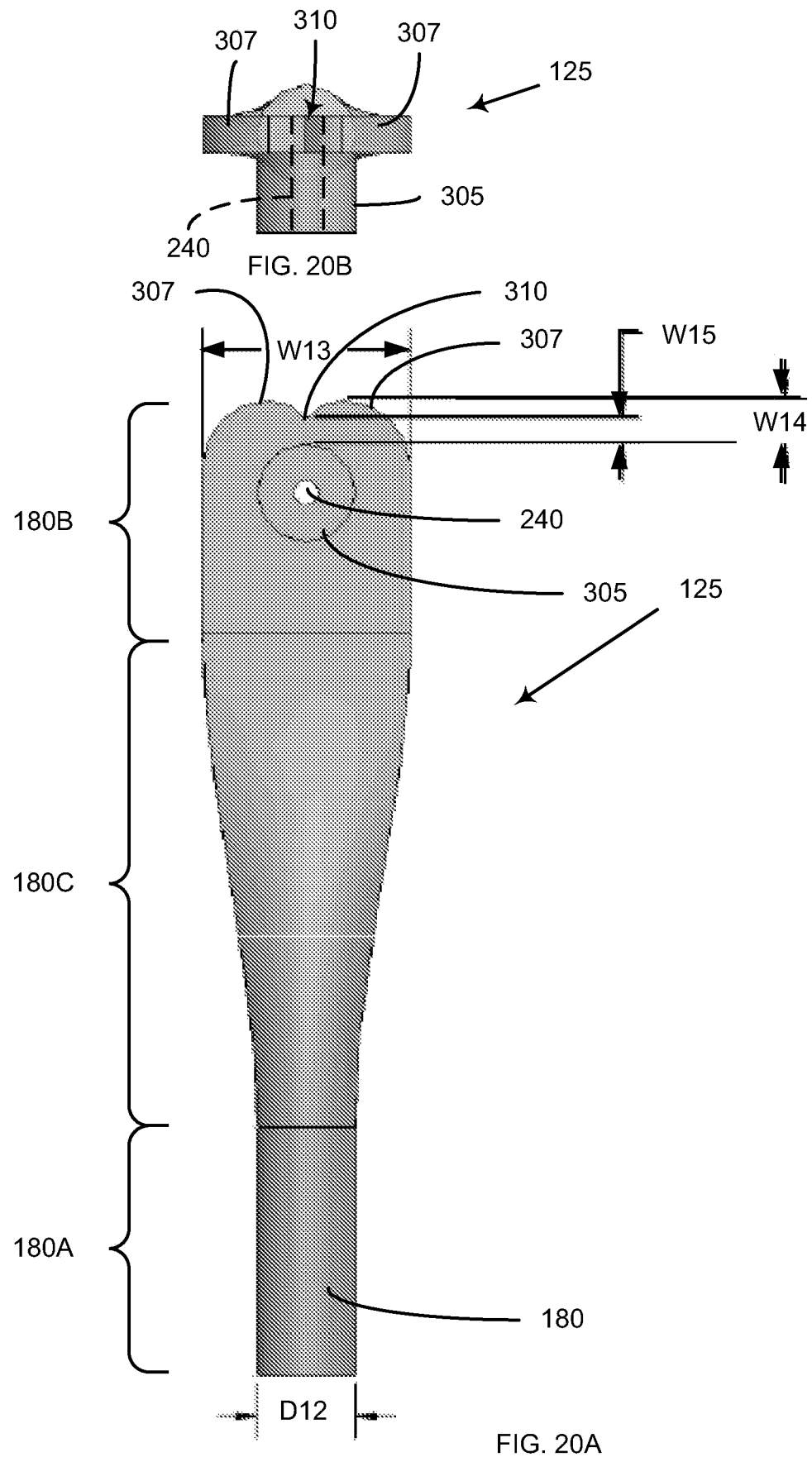
FIGS. 20A and 20B are the same respective views as FIGS. 18A and 18B, except of another embodiment.

As depicted in FIGS. 20A and 20B, which are the same respective views as FIGS. 18A and 18B, except of another embodiment, the inlet channel 180 may be said to have a complex arcuate configuration. Specifically, a cylindrical channel portion 180A transitions in portion 180C into a complex arcuate channel portion 180B. A cylindrical island portion or bezel 305 supporting the top bearing pin 130 is generally centered in the complex arcuate channel portion 180B and includes a cylindrical hole 240 that receives the top bearing pin 130 similar to as illustrated in FIG. 17. In one embodiment, the cylindrical channel portion 180A has a diameter D12 of approximately 4 mm. The complex arcuate channel portion 180B has a width W13 of approximately 8.4 mm. The distal distance W14 between the wall of the bezel 305 and the distal end dome 307 of the wall defining the complex arcuate channel portion 180B is approximately 1.75 mm. The distal distance W15 between the wall of the bezel 305 and the distal end cleft 310 of the wall defining the complex arcuate channel portion 180B is approximately 0.5 mm to 1.5 mm, preferably 1 mm. In other embodiments, the cylindrical channel portion 180A has a diameter D6 of approximately 5 mm or 6 mm.

Figure 21:
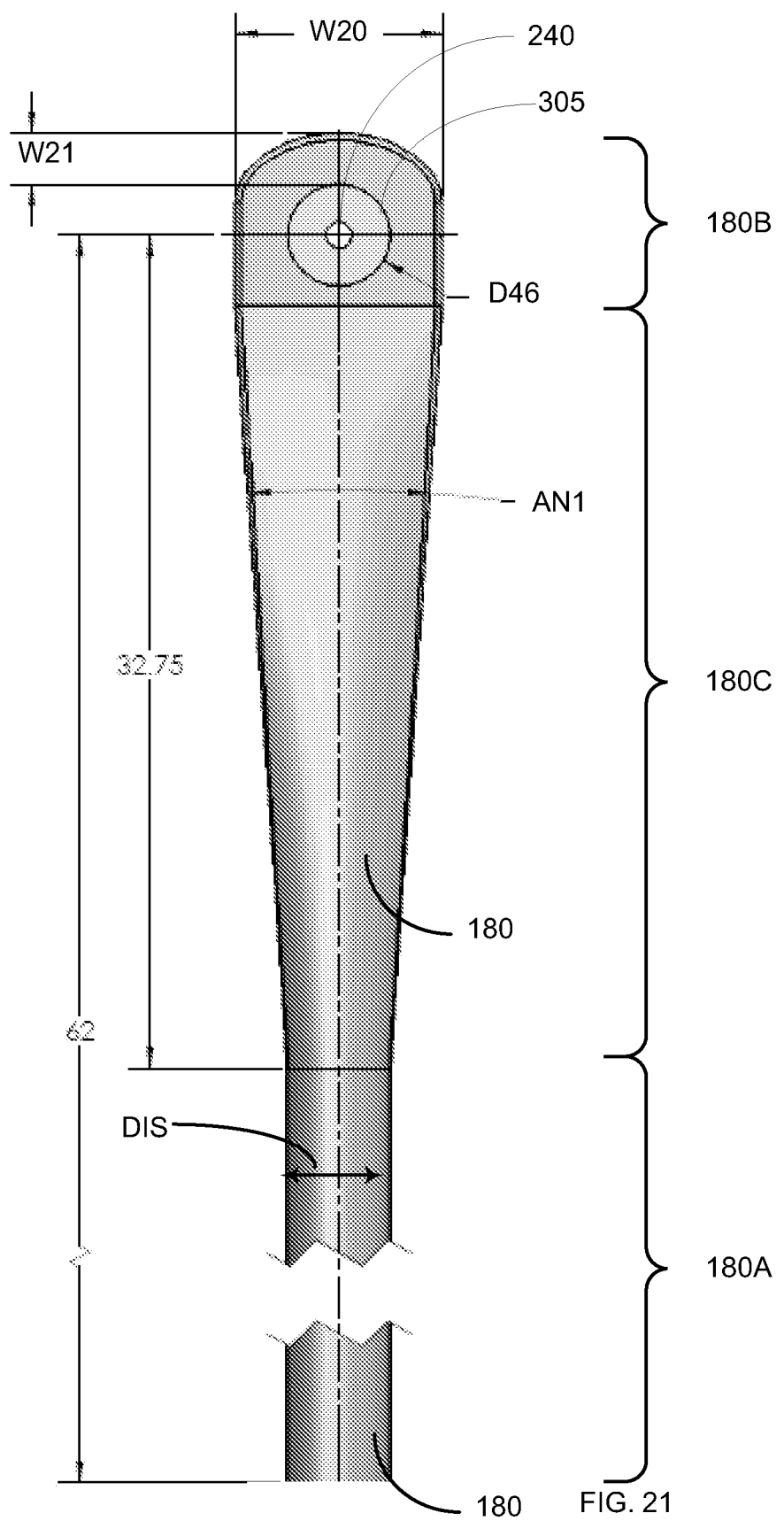
FIGS. 21-23 are the same views as FIG. 18A, except of three other embodiments.
Figure 22:
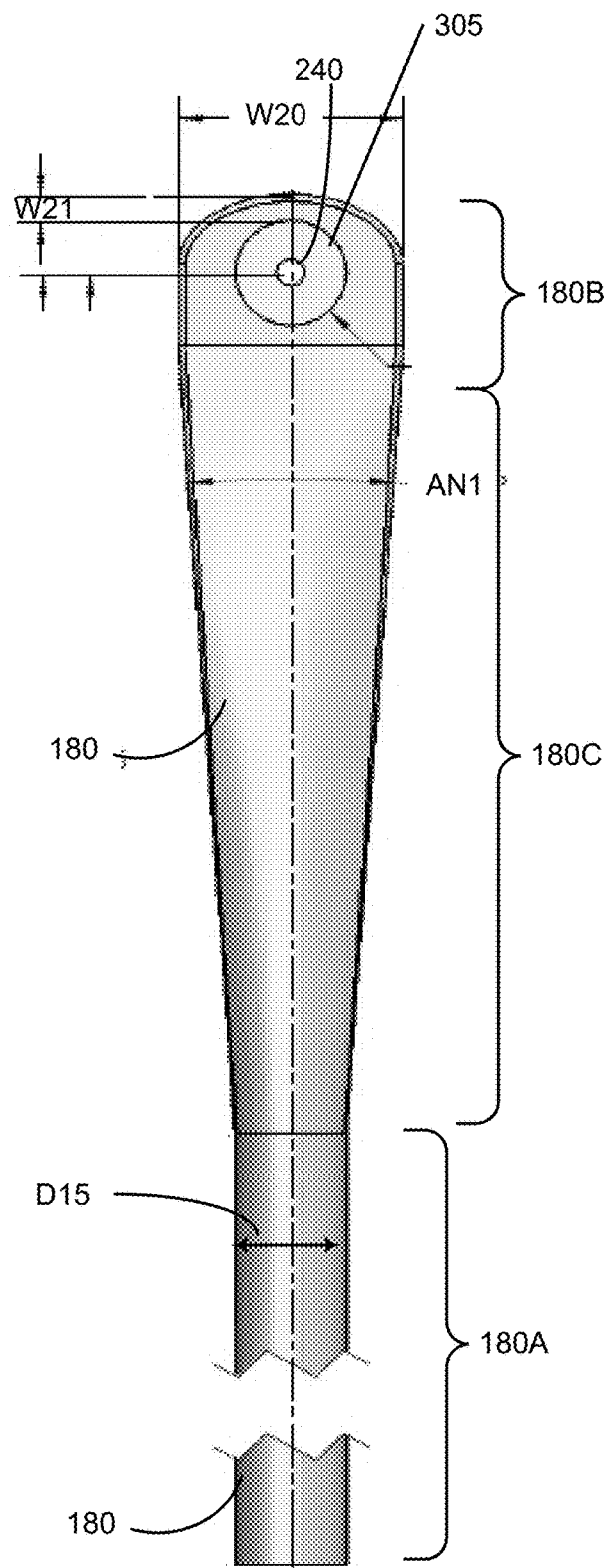
Figure 23:
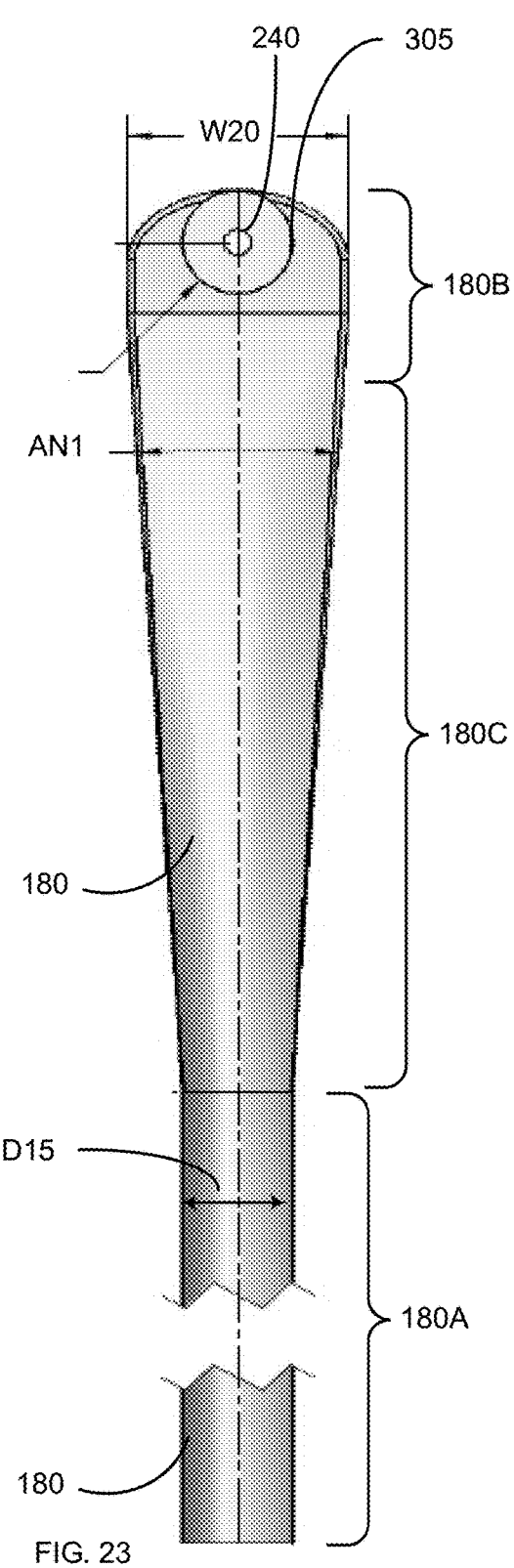

As depicted in FIGS. 21-23, which are the same views as FIG. 18A, except of three other embodiments, the inlet channel 180 may be said to have a tear drop configuration. Specifically, a cylindrical channel portion 180A transitions into a tear drop channel portion 180B. A cylindrical island portion or bezel 305 supporting the top bearing pin 130 is generally centered in the tear drop channel portion 180B and includes a cylindrical hole 240 that receives the top bearing pin 130 similar to as illustrated in FIG. 17. In one embodiment, the cylindrical channel portion 180A has a diameter D15 of approximately 4 mm. The tear drop channel portion 180B has a width W20 of approximately 8 mm. The bezel 305 has a diameter D16 of 4 mm. A transition region 180C of the channel 180 between the tear drop portion 180B and the cylindrical portion 180A has walls that diverge from each other at an angle AN1 of approximately 8 degrees. In other embodiments, the cylindrical channel portion 180A has a diameter D6 of approximately 5 mm or 6 mm.

For the embodiment of FIG. 21, the distal distance W21 between the wall of the bezel 305 and the distal end of the wall defining the tear drop channel portion 180B is approximately 2 mm. For the embodiment of FIG. 22, the distal distance W21 between the wall of the bezel 305 and the distal end of the wall defining the tear drop channel portion 180B is approximately 1 mm. For the embodiment of FIG. 23, the distal distance W21 between the wall of the bezel 305 and the distal end of the wall defining the tear drop channel portion 180B is approximately 0 mm because the bezel intersects the distal end of the wall defining the tear drop channel portion.

As illustrated in FIGS. 24A and 24B, which are, respectively, plan and side elevation views of another embodiment of the inlet cap 110 and inlet channel 180 similar to that described in FIG. 21, an arcuate wedged portion 320 may extend between the distal wall of the tear drop channel portion 180B to the distal side of the bezel 305. In such an embodiment, the cylindrical island portion or bezel 305 is generally centered in the tear drop channel portion 180B and includes a cylindrical hole 240 that receives the top bearing pin 130 similarly to as illustrated in FIG. 17. In one embodiment, the dimensional configuration of the embodiment depicted in FIGS. 24A and 24B is substantially the same as discussed with respect to FIG. 21, the significant difference being the presence of the arcuate wedge portion 320. As can be understood from FIGS. 24A and 24B, the wedge portion 320 has walls that are arcuate to smoothly curve from the roof and adjacent wall of the tear drop channel portion 180B to the vertical extension of the bezel 305. Such a wedged portion 320 may be seen to exist in the embodiment depicted in FIGS. 3A, 3B, and 17 and may reduce areas of inlet channel flow stagnation and facilitate tangential inflow of fluid through the impeller chamber inlet orifice 185.

Figure 25:
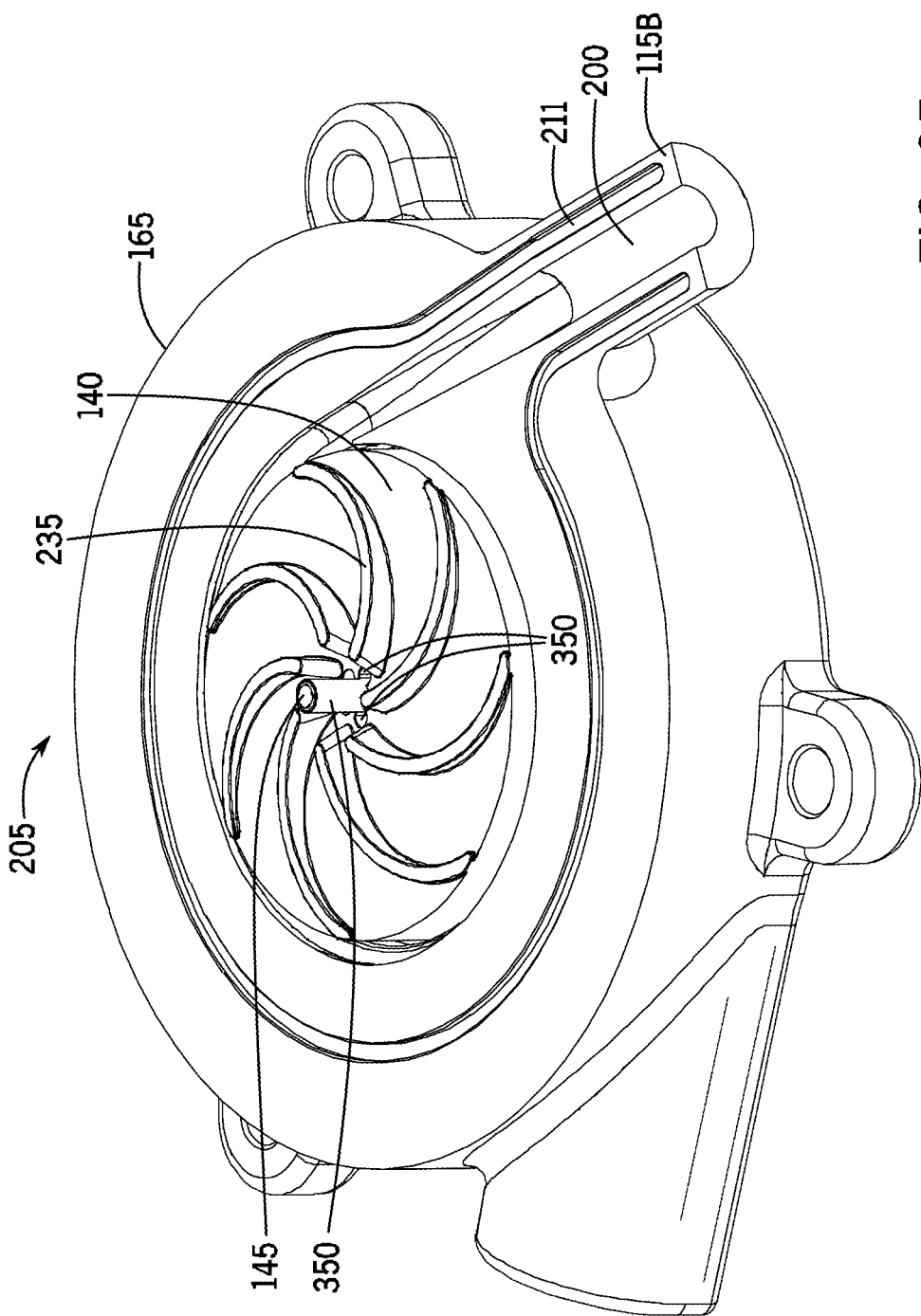
FIG. 25 is an isometric view of the pump with the top impeller casing removed to reveal the impeller occupying the impeller chamber.

As shown in FIG. 25, which is an isometric view of the blood pump 25 with the top impeller casing removed to reveal the impeller 140 occupying the impeller chamber 205, the outlet fluid channel 200 exits the impeller chamber substantially tangential to the outer circumferential edge of the impeller. As indicated in FIGS. 3B, 4B, 17, and 25, a plurality of bores 350 (i.e. washout holes) are circumferentially distributed about the impeller pivot center hole 250, and the bores 350 are generally parallel to the center hole 250 and extend though the full thickness of the impeller to daylight on both top and bottom boundaries of the impeller. The bottom openings of the bores 350 are located near the bottom bearing interface between the bottom bearing 165 and the impeller pivot bottom bearing surface 260 (see FIG. 8). As a result, a fluid can be flowed through the bores 350 to cleanse the bottom bearing interface. For example, a fluid can be flowed through the impeller chamber inlet hole 185, radially-outward along the impeller blades 235, through the gap under the impeller, and then back to the region of the impeller chamber inlet hole 185. This flow of blood serves to cleanse the underside of the impeller, the bottom bearing interface, the upper bearing interface, and the region behind the bezel 305.

As can be understood from FIGS. 3B, 5, 17, and 25, in one embodiment, the impeller 140 is rotationally supported in the impeller chamber 205 on a shaft 145 extending through a center of the impeller. The shaft has an upper bearing end and a bottom bearing end, each end rotatably operably coupled to the pump housing. The impeller has a top face, a bottom face, and multiple bores 350 extending through the impeller from the top face to the bottom face. The multiple bores are generally evenly distributed radially about center of the impeller. Further, the multiple bores extend through the impeller generally parallel to each other and the shaft. The inlet channel 180 leads to an inlet orifice 185 of the impeller chamber. The inlet channel opens into the impeller chamber generally perpendicular to the inlet channel. The inlet orifice extends along at least a portion of an outer circumferential surface of the shaft near the upper bearing end. The inlet orifice and the holes open in directions that are generally parallel to each other. During operation of the pump, at least a portion of the blood pumped through the impeller chamber circulates along the top and bottom faces of the impeller via the bores. Thus, the bores of the impeller eliminate flow dead ends around the impeller by generally keeping blood flowing along all blood contacting surfaces of the impeller. Accordingly, the bores help to prevent blood accumulation in the vicinity of the shaft/impeller intersection and along the sides and bottom face of the impeller.

The body and impeller of the blood pump 25, including blood-contacting surfaces, are made from a variety of rigid biocompatible materials. One option includes plastics, more preferably injection moldable plastics such as PEEK. In various embodiments, the blood-contacting surfaces of the blood pump 25 may comprise $Ti_6Al_4V$, $Ti_6Al_7Nb$, or other commercially pure titanium alloys. In one embodiment, the surfaces of the pump components to be exposed to the patient's blood may have antithrombotic coatings. For example, the luminal surfaces may be coated with Astute®, a heparin based antithrombotic coating by BioInteractions Ltd., or Applause™, a heparin coating by SurModics, Inc.

In other embodiments, the surfaces of the blood pump system components in contact with the patient's tissue may have antimicrobial coatings. For example, the external surfaces of the synthetic conduits 16 and 18 or the external surfaces of the pump or the power cord 120 (which is also know as a "lead") may be coated with Avert®, a surface-active antimicrobial coating by BioInteractions Ltd.

Figure 34:
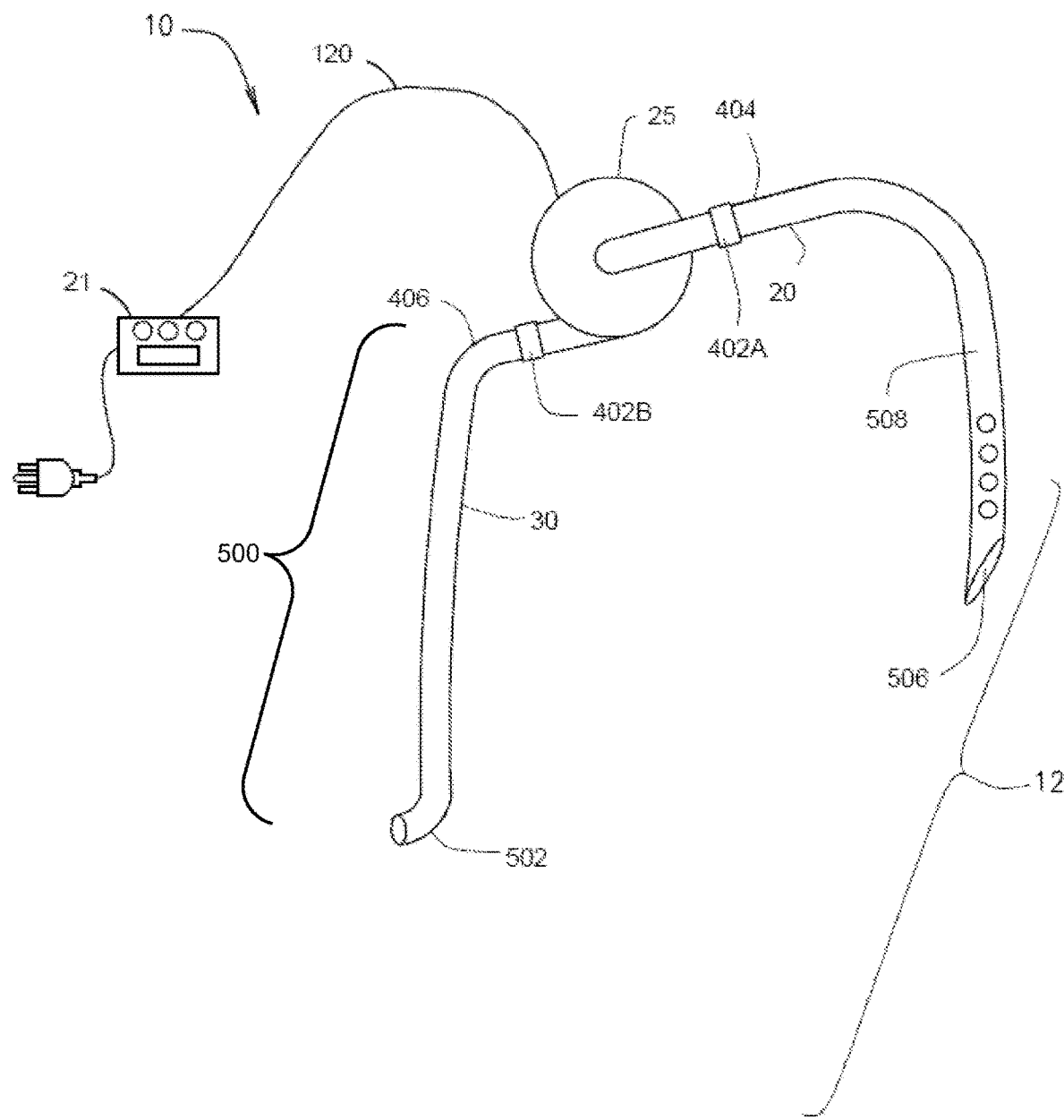
FIG. 34 is a schematic view of the pump system according to another embodiment.

In various embodiments, the blood pump 25 may be implanted within a patient. Conversely, in other embodiments, the blood pump 25 may remain external to the patient. For example, when located externally to the patient, the blood pump 25 may be secured to the patient using tape, sutures, or other suitable means to affix the pump to the patient. The system 10 may be powered by wearable electronics having rechargeable batteries 28, as shown in FIG. 34.

The pump for the pump system 10 disclosed herein may be a rotary pump, including, for example, a centrifugal flow pump, an axial flow pump, a radial flow pump, or a mixed flow pump. As shown in FIGS. 1-15, in one embodiment, the pump is a centrifugal pump. Without recognizing specific limitations, the blood pump 25 can be configured to routinely pump about 0.05 to 1.0 L/min, 0.2 to 1.5 L, or 0.5 to 3.0 L/min, for example.

While the pump configuration discussed above with respect to FIGS. 1-25 is advantageous, other pump configurations may be employed with the pump systems and methods disclosed herein. Accordingly, the systems and methods disclosed herein should not be limited to the pump configuration discussed above with respect to FIGS. 1-25, but should include all types of pumps applicable for the systems and methods disclosed herein.

A preferred embodiment of the pump system 10 disclosed herein with respect to FIGS. 1-25 satisfies several unique needs that cannot be satisfied by any blood pump systems known in the art. Specifically, the Arteriovenous Fistula Eligibility ("AFE") pump system ("AFE System") may be configured for up to 12 weeks of intended use. Further, the AFE pump system may be configured as a centrifugal rotary blood pump system for low flow rate (e.g., 50 to 1500 mL/min) and medium pressure range (e.g., 25 to 350 mmHg). A control scheme used with the AFE pump system may be optimized to maintain a steady and elevated mean WSS of 0.76-23 Pa in target veins that are directly fluidly connected to the blood pump or a conduit of the blood pump system, or target veins that are fluidly connected to a vein that is directly fluidly connected to the blood pump or a conduit of the blood pump system. The AFE pump system is configured to operate for a period of time such that the overall diameter and lumen diameter of the target vein will persistently increase by 25%, 50%, or 100% or more, utilizing sensing of operating parameters and periodic speed adjustment.

For certain embodiments, the inflow conduit may be placed by percutaneous approach, with a portion of the inflow conduit residing in an intravascular location, and the outflow conduit may be placed by surgical approach adaptable to initial vein diameters of between 1-6 mm. In this setting, elevated mean WSS in the target blood vessel results from discharging blood into the target blood vessel.

For other embodiments, the outflow conduit may be placed by percutaneous approach, with a portion of the outflow conduit residing in an intravascular location, and the inflow conduit may be placed by surgical approach adaptable to initial vein or artery diameters of between 1-6 mm. In this setting, elevated mean WSS in the target blood vessel results from removing blood from the target blood vessel. In certain settings, WSS can be elevated in both a blood vessel where blood is removed and a blood vessel where blood is discharged, making both blood vessels target blood vessels. The pump system 10 achieves both ease of insertion/removal and resistance to infection. The pump system 10 is a mobile system with a pump that is adaptable for either implanted or extracorporeal placement. In various embodiments, the pump system 10 is powered by wearable electronics with rechargeable batteries.

Figure 26:
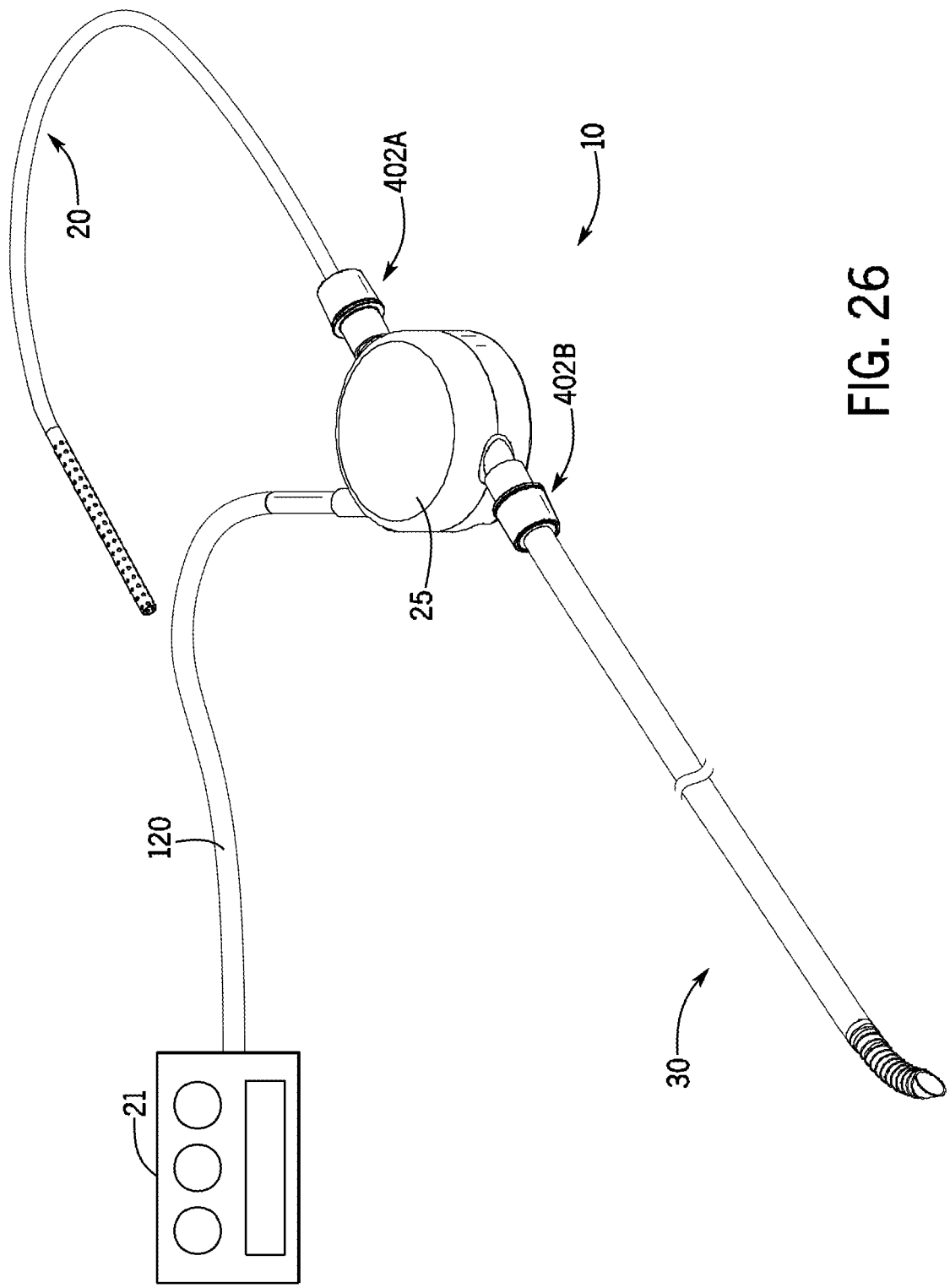
FIG. 26 is a perspective view of a blood pump system according to one embodiment.
Figure 27A:
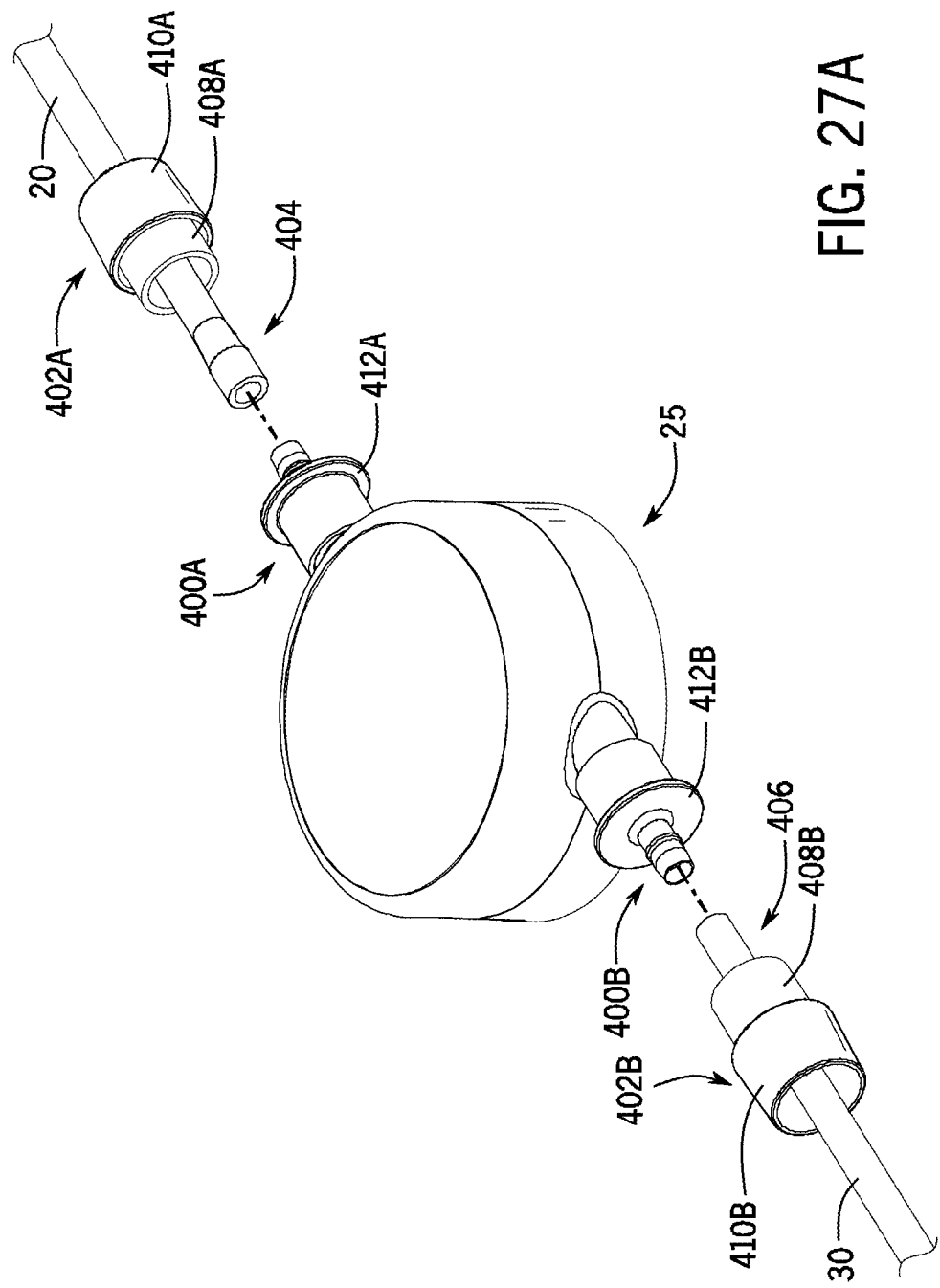
Figure 27B:
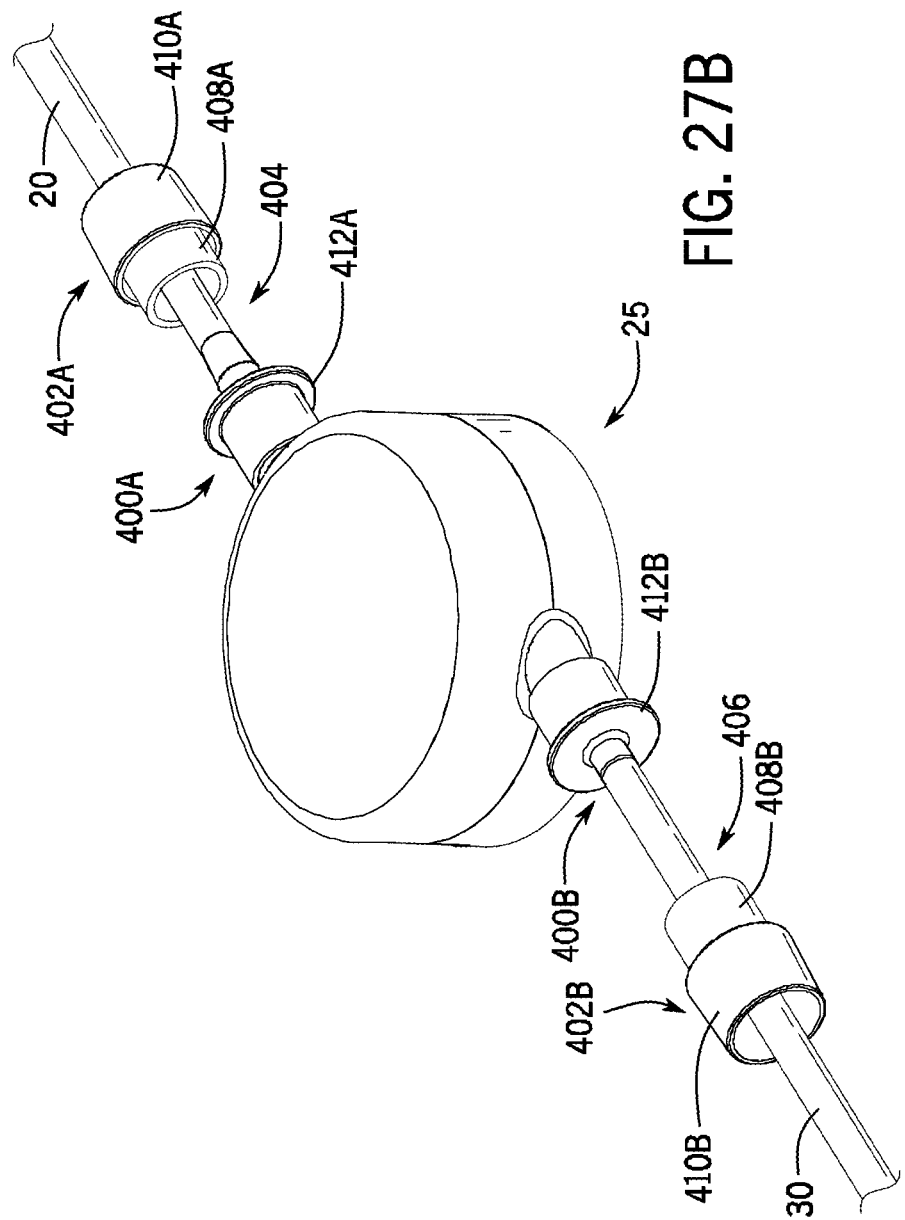
Figure 27D:
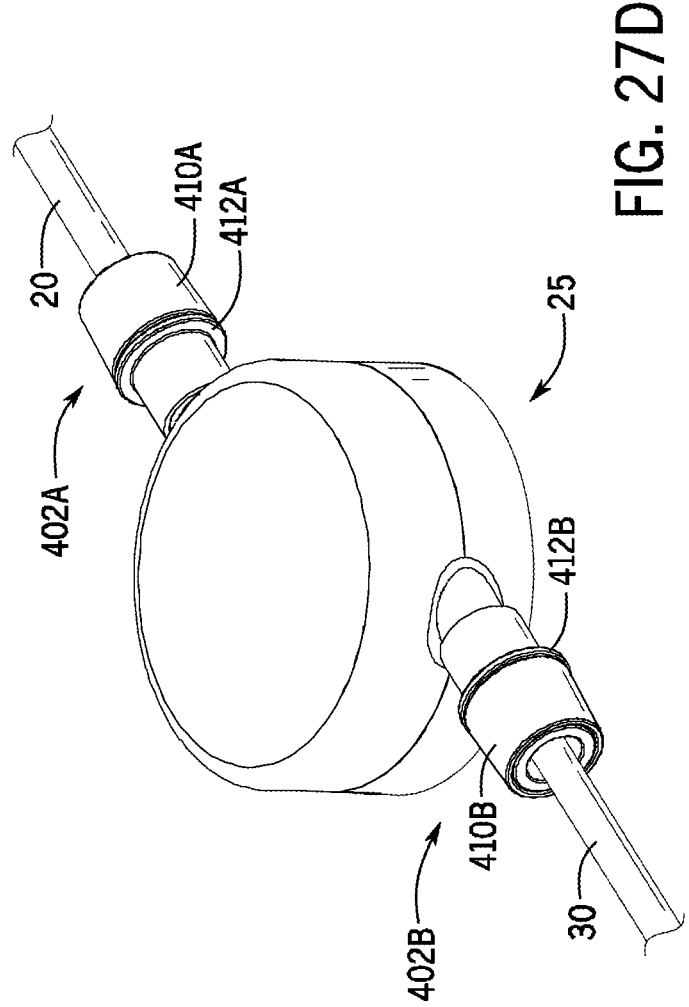

The pump system 10 includes an inflow conduit 20 and an outflow conduit 30, as shown in FIG. 26. The inflow conduit 20 is placed in fluid communication with one location in the vascular system, draws blood from this location, and carries it to the blood pump 25. In certain embodiments, the inflow conduit 20 is configured for placement of at least a portion of the inflow conduit within the lumen of the vascular system. In other embodiments, the inflow conduit 20 is joined to a blood vessel by a surgical anastomosis. The outflow conduit 30 is configured for making a fluid communication with another location in the vascular system and directs blood from the blood pump 25 to the other location in the vascular system. In certain embodiments, the outflow conduit 20 is configured for placement of at least a portion of the outflow conduit within the lumen of the vascular system. In other embodiments, the outflow conduit 30 is joined to a blood vessel by a surgical anastomosis.

The conduits 20 and 30 may each have a length that ranges between 2 cm and 110 cm and a total combined length of 4 cm to 220 cm. The length of the each conduit 20 and 30 may be trimmed to a desired length as determined by the location of the blood pump 25 and the location of the connections between the conduits and the vascular system. The conduits 20 and 30 also have thin but compression-resistant and kink-resistant walls that have a thickness of between 0.5 mm and 4 mm and inner diameters that are between 2 mm and 10 mm. Preferably, the inner diameters for the conduits are 4 to 6 mm.

The inflow and outflow conduits 20 and 30 may be connected to the blood pump 25 using any suitable connector that is durable, resists leaks, and is not susceptible to unintentional disengagement. Typically, the leading edge of the connector is thin, in order to minimize the step change in fluid path diameter between the inner diameter of the conduits 20 and 30 and the inner diameter of the connector. Preferably, the step change in fluid path diameter should be less than 0.5 mm. In one embodiment, as shown FIGS. 27A-27D, the conduits 20 and 30 are connected to the blood pump 25 using barb fittings 400A and 400B and radially compressive retainers (i.e. locking collars) 402A and 402B. By way of example, and not limitation, the radially compressive retainers 402A and 402B, may be BarbLock® retainers manufactured by Saint-Gobain Performance Plastics, a division of Saint-Gobain S.A. headquartered in Courbevoie, France. In another embodiment, the conduits 20 and 30 are connected to the blood pump 25 using Pure-Fit® sterile connectors, also manufactured by Saint-Gobain Performance Plastics.

The radial compressive retainers 402A and 402B are placed over the proximal ends 404 and 406 of the inflow and outflow conduits 20 and 30, respectively. The conduits 20 and 30 are then placed over the barb fitting 400A and 400B to form a fluid connection between the conduits and the blood pump 25. Collets 408A and 408B of the radial compressive retainers 402A and 402B are placed along the conduits 20 and 30 to encircle the conduits and the barb-fittings 400A and 400B. Outer sleeves 410A and 410B of the radial compressive retainers 402A and 402B are then moved along a longitudinal axis of the retainers to compressively engage the respective collets 408A and 408B, conduits 20 and 30, and the barb fittings 400A and 400B. In one embodiment, the outer sleeves 410A and 410B are moved by a compressive tool configured to engage the outer sleeves and a support shelf 412A and 412B of the barb fittings 400A and 400B, respectively. The compressive tool may also be configured to remove the radial compressive retainers 402A and 402B.

Figure 28A:
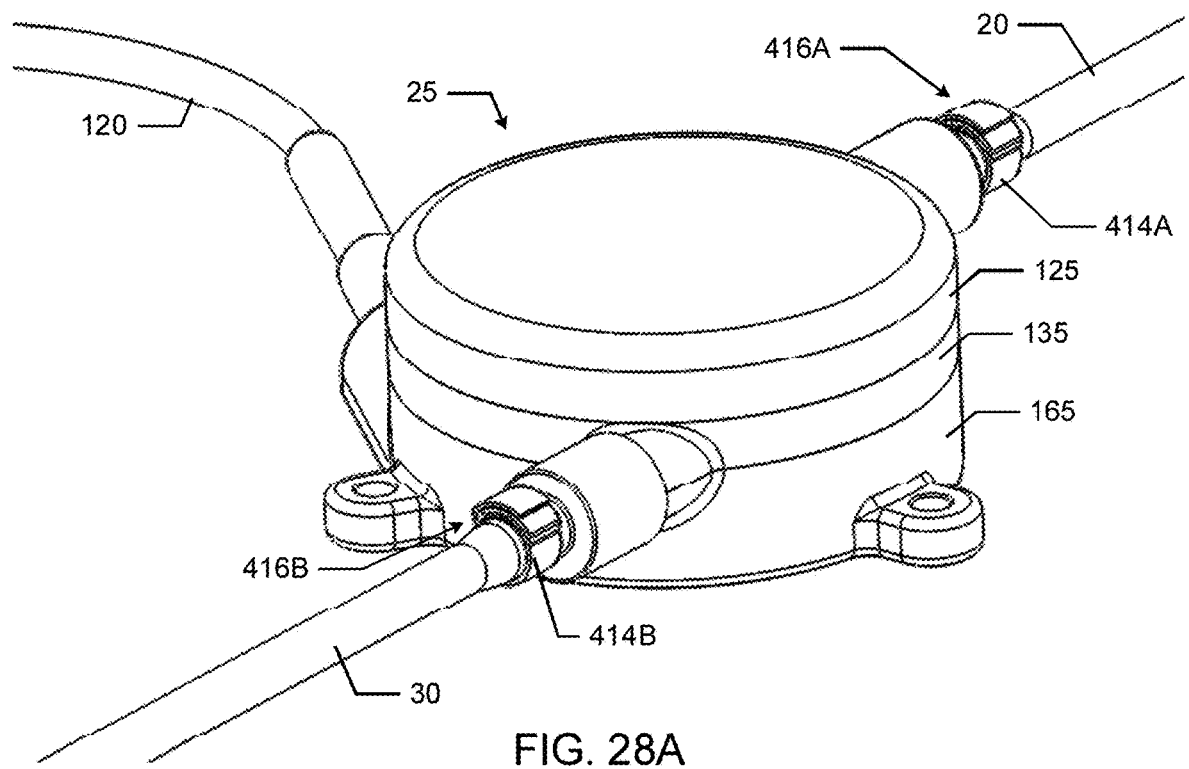
FIGS. 28A and 28B are perspective views of the connection between the pump and conduits according to one embodiment.
Figure 28B:
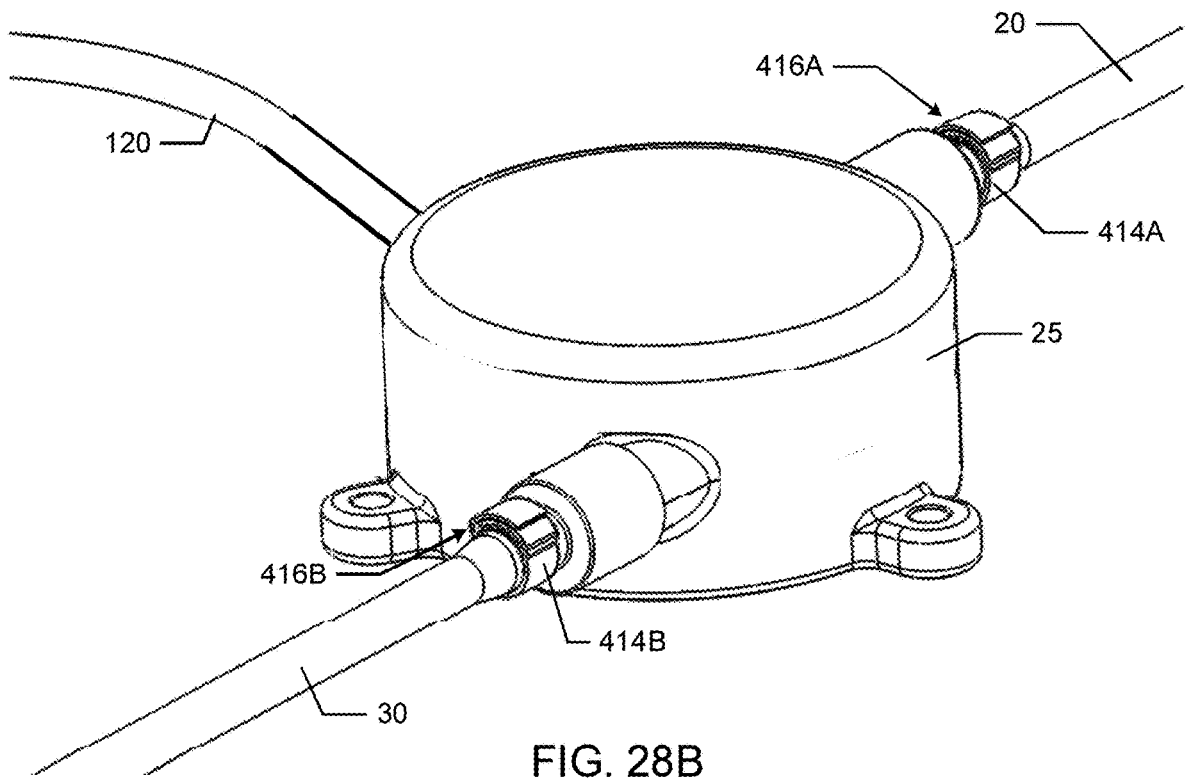

In other embodiments, alternative connectors may be used. Preferably, the alternative connectors are durable, resist leaks, and resist unintentional dislodgment. For example, as shown in FIG. 28A-B, the conduits 20 and 30 engage barb fittings, similar to barb fittings 400A and 400B, to form a fluid connection between the conduits and the blood pump 25. The conduits 20 and 30 are secured to the barb fittings using circular clips 414A and 414B that apply radial compressive force to the portion of the conduits on the barb fittings by way of a ratcheting mechanism 416A-416B of the clips. The circular clips 414A and 414B provide a leak-resistant and durable connection that may be removed with a removal tool (not shown) which releases the ratcheting mechanisms 416A-416B of the clips.

Figure 29A:
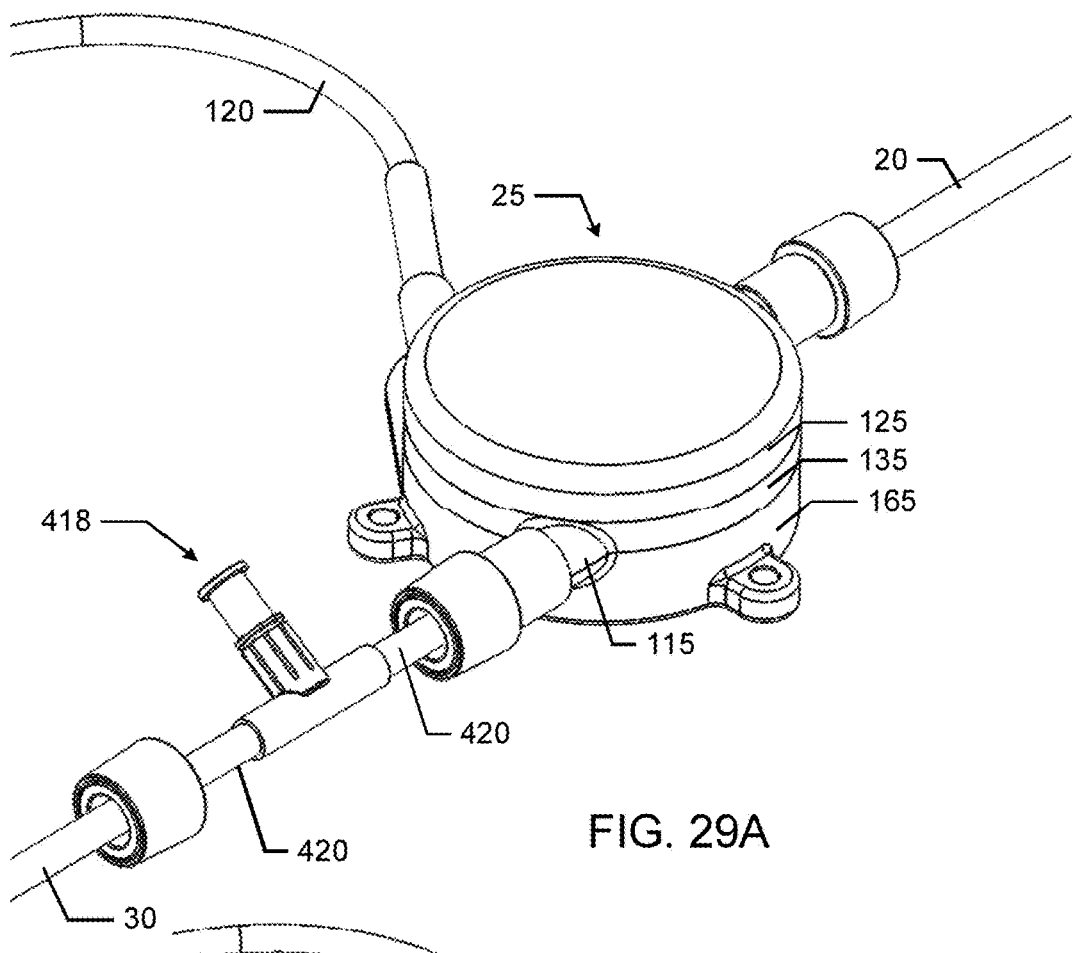
FIGS. 29A and 29B are perspective views of the connection between the pump and conduits that include a side port according to one embodiment.
Figure 29B:
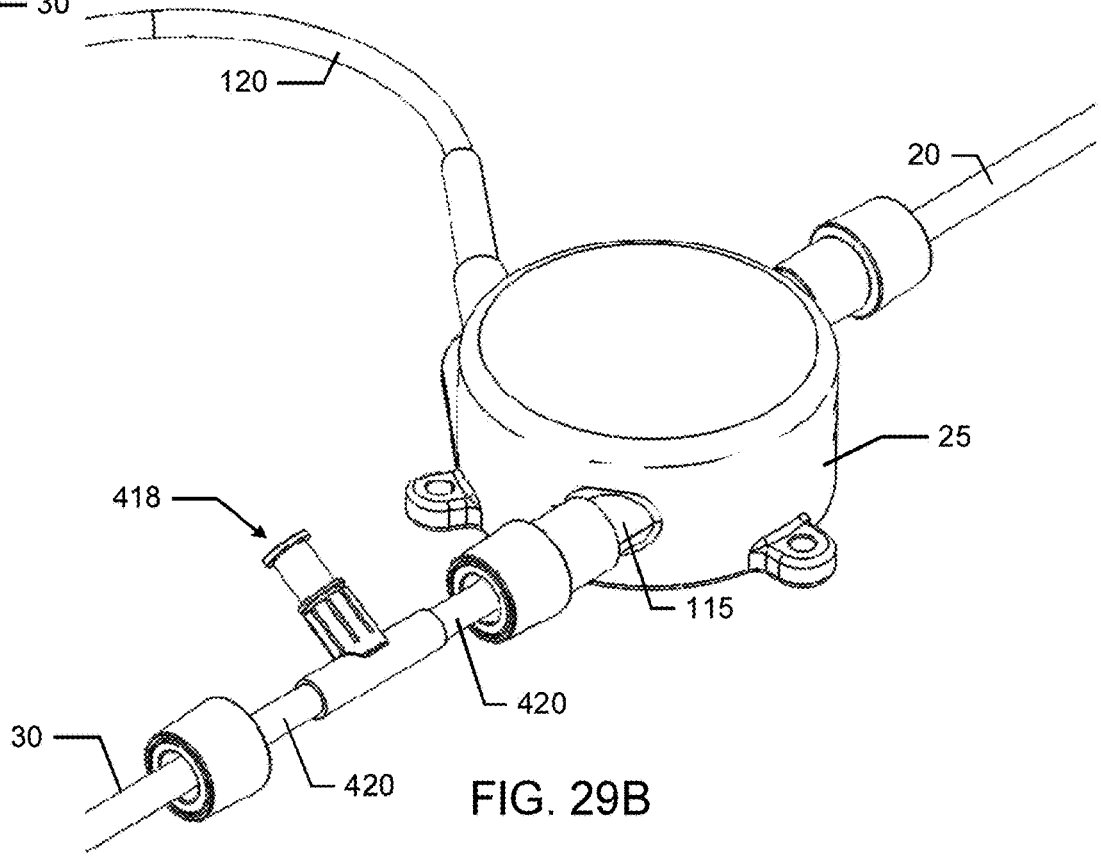

In another embodiment, the inflow conduit 20 and the outflow conduit 30 contain side ports that provide controlled access to the fluid path. Side ports may be used periodically to introduce contrast into the fluid path to enable visualization by fluoroscopy, to obtain blood samples, to infuse medications, or for other clinically useful purposes. Any side port design that allows periodic access to the fluid path and does not leak or alter the fluid flow path when not accessed is suitable. By way of example, and not limitation, the side port may be a "T" port fitting that includes a check valve that opens when a syringe is inserted and closes when the syringe is removed. As shown in FIGS. 29A-B, a "T" port assembly 418 with auxiliary tubing 420 is in fluid communication with the pump outlet 115 and outflow conduit 30.

Figure 30A:
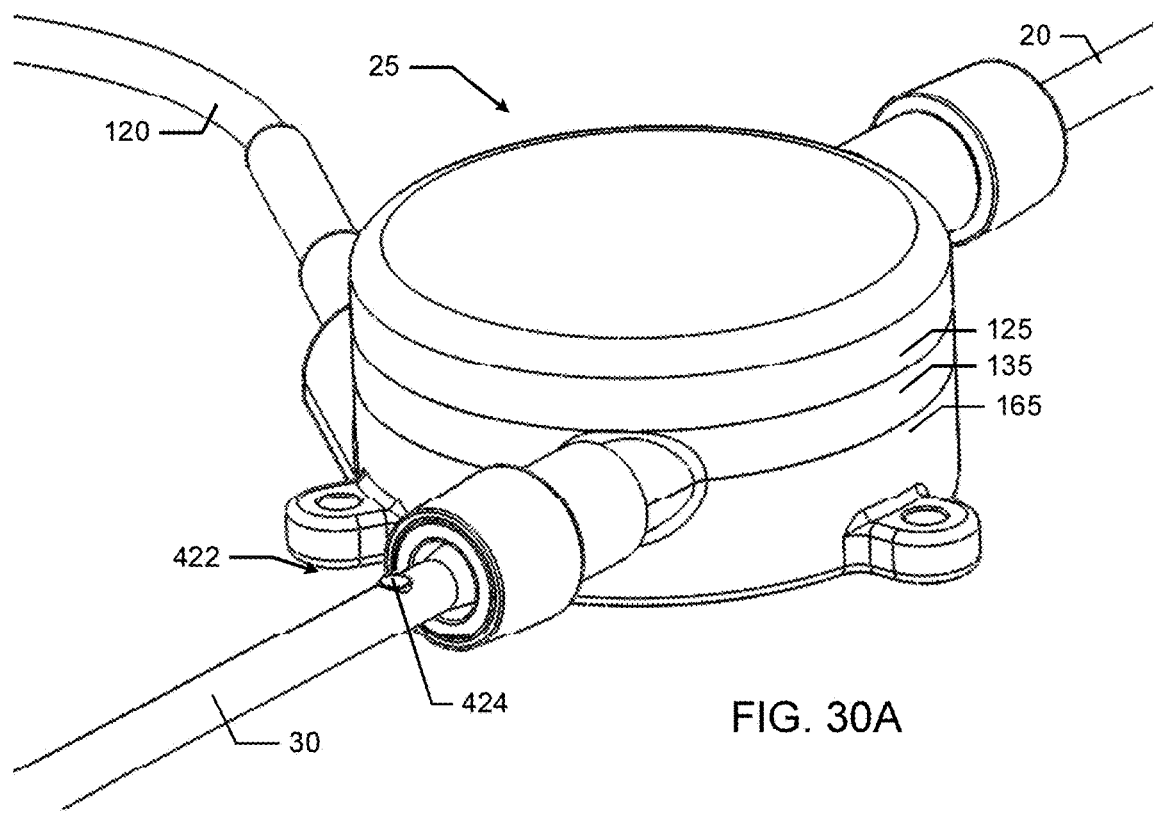
FIGS. 30A and 30B are perspective views of the connection between the pump and conduits that include a septum according to one embodiment.
Figure 30B:
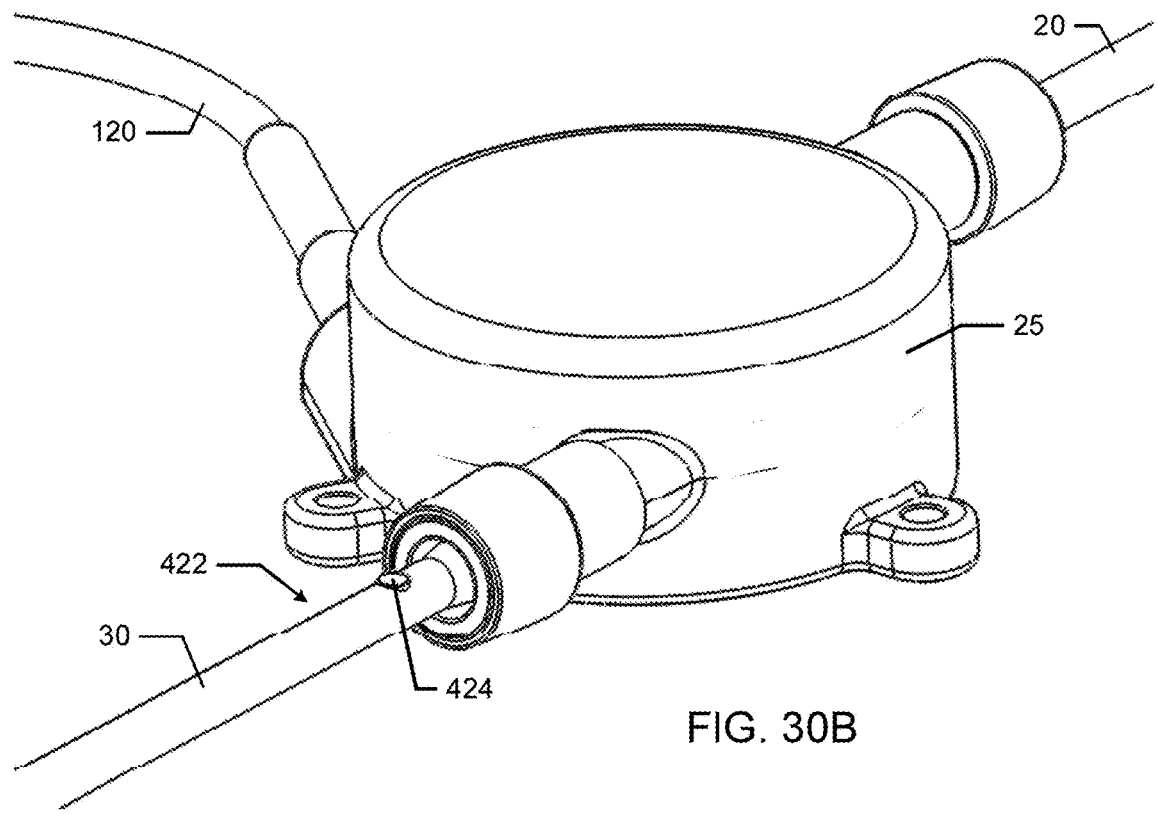

In another embodiment, a side port for the inflow conduit 20, the outflow conduit 30, or both utilizes a septum access port 422 having a septum 424, as shown in FIGS. 30A-B, through which a suitable hypodermic needle can be inserted for access and then removed, after which the septum closes, preventing fluid loss from the conduit. Suitable materials for the septum 424 include, but are not limited to, silicone, polyurethane, and other elastomeric polymers. The segment of the inflow and/or outflow conduit 20 or 30, respectively, which includes the septum 424, is of a suitable thickness to close a hypodermic puncture hole when the needle is removed. As shown in FIGS. 30A-B, the septum access port 422 is shown in which the septum 424 makes up a portion of the outflow conduit 30. By way of example, and not limitation, the septum access port 422 may extend about one centimeter over the length of the outflow conduit 30. The septum 424 may be attached to the outflow conduit 30 by any suitable means including, but not limited to, adhesive attachment, thermal bonding, and thermal bonding between inner and outer layers of the conduit tubing.

In various embodiments, the conduits 20 and 30 may be comprised of materials commonly used to make hemodialysis catheters such as polyurethane, polyvinyl chloride, polyethylene, silicone, and polytetrafluoroethylene (PTFE), and including Pellethane® or Carbothane®. In other embodiments, the conduits may be comprised of materials commonly used to make hemodialysis grafts or synthetic peripheral bypass grafts such as expanded polytetrafluoroethylene (ePTFE) or Dacron. In further embodiments, conduits may be comprised of combinations of polyurethane, polyvinyl chloride, polyethylene, silicone, PTFE, Pellethane®, Carbothane®, Carbothane® PC-3575, ePTFE, or Dacron.

For example, the entire length of the inflow conduit 20 may be composed of polyurethane. In another embodiment, shown in FIG. 31, a segment 500 of the outflow conduit 30 configured to make a fluid communication with the blood pump 25 is composed of polyurethane while a segment 502 of the outflow conduit configured to make a fluid communication with the vascular system is composed of ePTFE.

Figure 41:
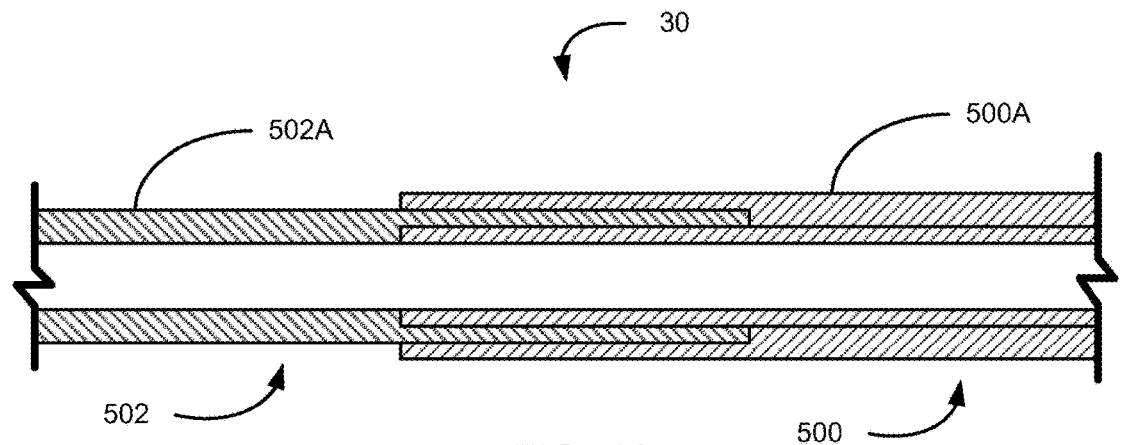
FIG. 41 is a longitudinal cross section of the junction between the proximal segment and distal segment.

By way of example and not limitation, and as shown in FIG. 41, which is a longitudinal cross section of the junction between the proximal segment 500 and distal segment 502, the proximal segment 500 of the outflow conduit 30 is joined to the distal segment 502 of the outflow conduit during the manufacturing process by placing one or more layers 502A of ePTFE from the distal segment between layers 500A of polyurethane from the proximal segment. The overlapping layers of polyurethane and ePTFE are then heat laminated to bond the proximal segment 500 and the distal segments 502 together.

In another example, one or more holes are made within the overlapped sections of the ePTFE of segment 502 prior to heat laminating the conduit. When the outflow conduit 30 is heated to a temperature that is sufficient to melt the polyurethane without melting the ePTFE (e.g. 200° F. to 500° F.), the molten polyurethane fills in and then cools within the holes created in the ePTFE segment 502. The inner and outer polyurethane layers of the segment 500 are joined with in the holes to mechanically join the two segments 500 and 502 together as well as mechanically join the inner and outer layers of polyurethane in the overlapped segment.

The embodiment of the outflow conduit 30 manufactured to have the ePTFE layer 502A sandwiched between the polyurethane layers 500A is advantageous in that the ePTFE layer 502A can be readily sutured to blood vessels using standard techniques. This is also the case for an inflow conduit 20 manufactured as discussed above with respect to FIG. 41.

Figure 42:
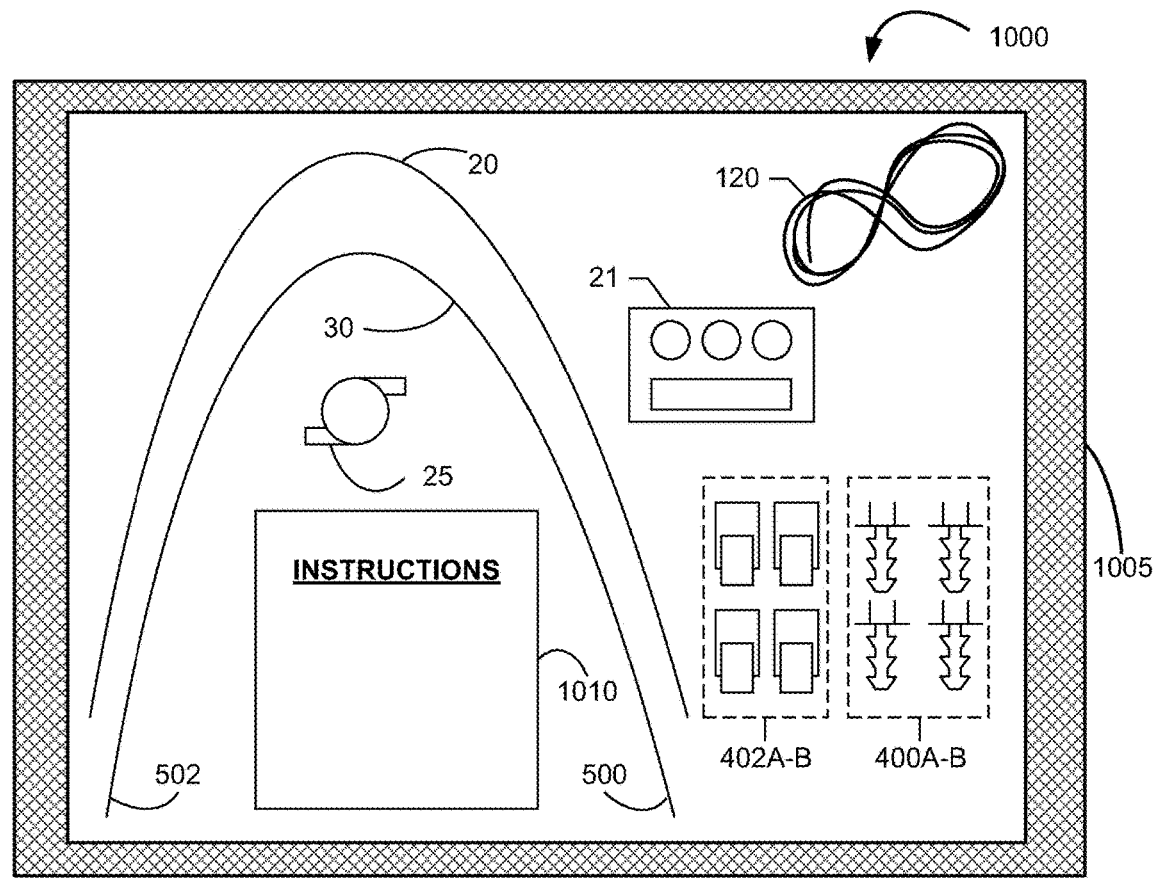
FIG. 42 is a plan view of a medical kit.

As illustrated in FIG. 42, which is a plan view of a medical kit 1000, the blood pump 25, inflow conduit 20, outflow conduit 30, control device 21, and power cord 120 can be provided in a sterile package 1005 with instructions 1010 on how to assemble and implant the pump system in a patient. The medical kit 1000 may also include the barb fittings 400A and 400B and the radially compressive retainers 402A and 402B. In one embodiment, one or both conduits 20, 30 are manufactured as described above with respect to FIG. 41 and enclosed within the sterile package 1005 along with the blood pump 25. The medical kit 1000, at a minimum, includes a system for discharging or removing blood and instructions for implementation and usage.

Figure 43:
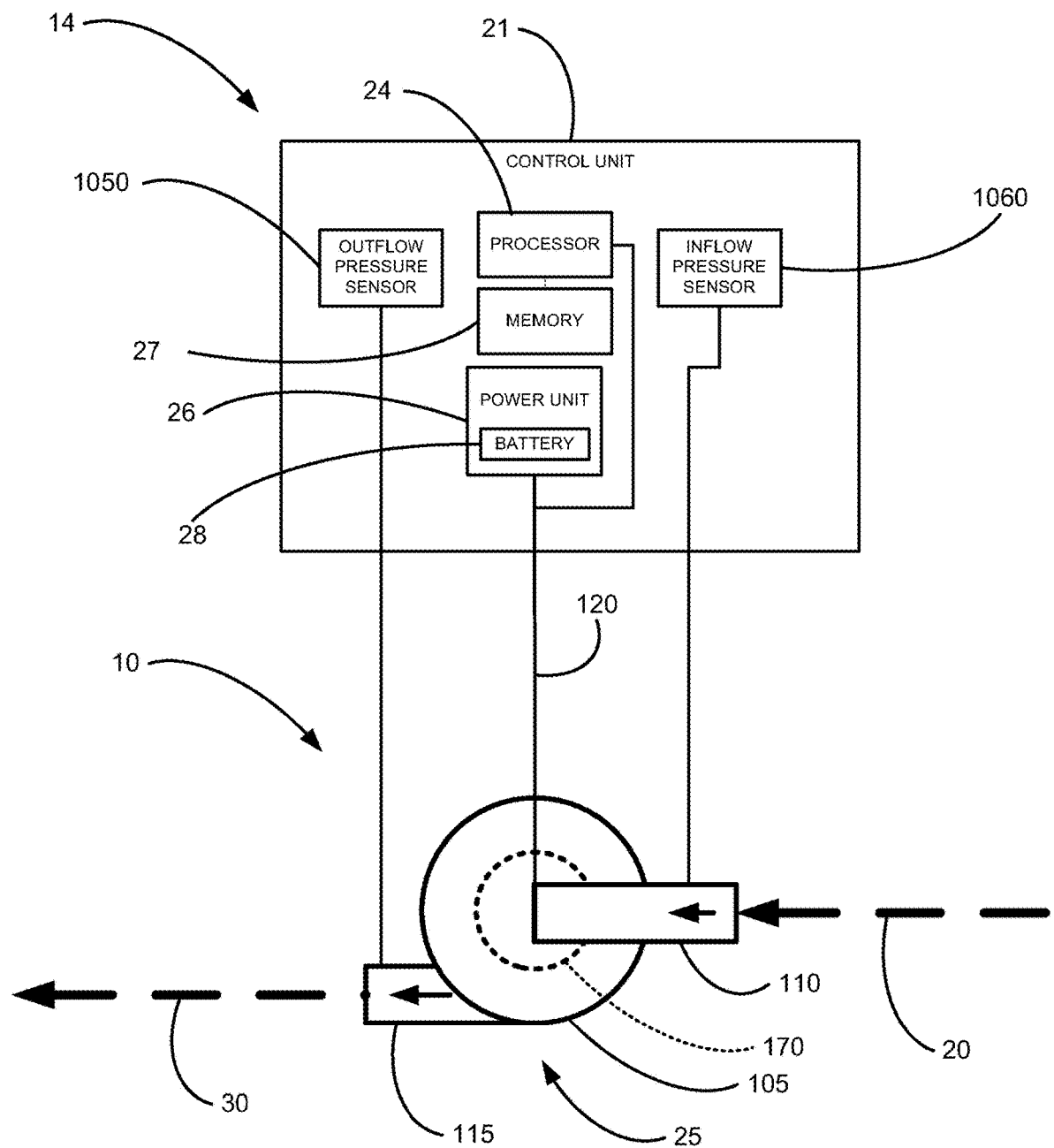
FIG. 43 is a schematic diagram of a pump system controlled according to outflow pressure.

In one embodiment, the operation of the blood pump 25 is controlled via the control unit 21 of a pump control system 14 by reading the outflow pressure and adjusting the pump speed accordingly. For example, as depicted in FIG. 43, which is a schematic diagram of a pump system 10 controlled according to outflow pressure, an outflow pressure sensor 1050 may be operably coupled to the outlet 115 of the blood pump 25 or further downstream, such as, for example, somewhere along the length of the outflow conduit 30. The processor 24 may compare the pressure reading from the outflow pressure sensor 1050 to a range of target outflow pressures stored in the memory 27. The processor will then adjust the speed of the pump drive 170 accordingly to cause the pressure reading from the outflow pressure sensor 1050 to be within the range of target outflow pressures stored in the memory.

In one embodiment, the control system 14 also includes an inflow pressure sensor 1060 that may be operably coupled to the inlet 110 of the blood pump 25 or further upstream, such as, for example, somewhere along the length of the inflow conduit 20. The processor 24 may read both the pressure reading from the outflow pressure sensor 1050 and the pressure reading from the inflow pressure sensor 1060 and calculate a pressure difference. This pressure difference may then be compared to a range of target pressure differences stored in the memory 1055. The processor will then adjust the speed of the pump drive 170 to cause the calculated pressure difference to be within the range of target pressure differences stored in the memory.

In other embodiments, the inflow and outflow conduits 20 and 30 can be any material or combination of materials so long as the conduits 20 and 30 exhibit desirable characteristics, such as flexibility, sterility, resistance to kinking and compression, and can be connected to a blood vessel via an anastomosis or inserted into the lumen of a blood vessel, as needed. In addition, the conduits 20 and 30 preferably exhibit the characteristics needed for subcutaneous tunneling as desired, such as comprising lubricious external surface coatings such as Harmony™ advanced lubricity coatings.

As another example, the inflow and outflow conduits 20 and 30 may have an exterior layer composed of a different material than the interior layer. All or a portion of the external layers of the inflow and outflow conduits 20 and 30 may also be coated with a lubricating agent, such as silicon or a hydrophilic coating to aid in subcutaneous tunneling and removal from the body, and to mitigate possible allergic reactions to latex. In certain embodiments, at least a portion of the surface of the exterior layer of the inflow and outflow conduits 20 and 30 may have an antimicrobial coating. In other embodiments, at least a portion of the surface of the blood pump 25 or the power cord 120 may have an antimicrobial coating. For example, Avert™, a surface active antimicrobial coating may be used. In certain embodiments, a portion of the surface of the exterior layer of an inflow and outflow conduit may include a material to resist infection and encourage tissue incorporation, such as Dacron velour, polyester velour, or silicone. One such material is the VitaCuff® antimicrobial cuff by Vitaphore Corp. The Vita-Cuff cuff is comprised of two concentric layers of material. The internal layer is constructed of medical grade silicone. The external, tissue-interfacing layer comprises a collagen matrix with an antimicrobial activity that is attributable to silver ions bound to the collagen. In certain embodiments, this material absorbs physiological fluids, quickly expands, and helps provide a physical barrier at the exit site. Tissue in-growth occurs, further securing the conduit in place, and reducing conduit movement to reduce the incidence of exit site infection.

When a portion of a pump-conduit assembly or pump-catheter assembly is located external to the body, then an antimicrobial coating can be incorporated onto the external surface to at least the portion of the device including conduits, catheters, pumps, leads, or any combination thereof, especially portions that connect the implanted and external components. For example, when a controller and/or power source is strapped to the arm or wrist, attached to a belt, or carried in a bag or pack, then the antimicrobial coating is incorporated on the surface of materials that enters the patient's body, such as synthetic conduits, catheters, or pump leads. In another embodiment, a cuff may be applied to the portions of the device that connect the implanted and external components. The cuff may reduce the risk of infection by facilitating tissue incorporation and may reduce the incidence of wound opening by the reducing the mobility of the connection point. In another embodiment, a coating that reduces the accumulation of thrombus (such as an anti-thrombotic coating) can be incorporated onto the internal blood-contacting surfaces of the pump-conduit assembly and pump-catheter assembly. This anti-thrombotic coating can be incorporated into the conduits, catheters, pumps, or any combination thereof.

In certain embodiments, at least a portion of the blood-contacting luminal surfaces of the inflow and outflow conduits 20 and 30 may be coated with an antithrombotic agent or material. Similarly, at least a portion of the blood-contacting surfaces of the blood pump 25 may be coated with an antithrombotic agent or material. For example, the surfaces may be coated with the Applause® coating from SurModics, Inc., or the Astute® coating from BioInteractions Ltd., which are both hydrophilic copolymer coatings containing heparin.

Figure 31:
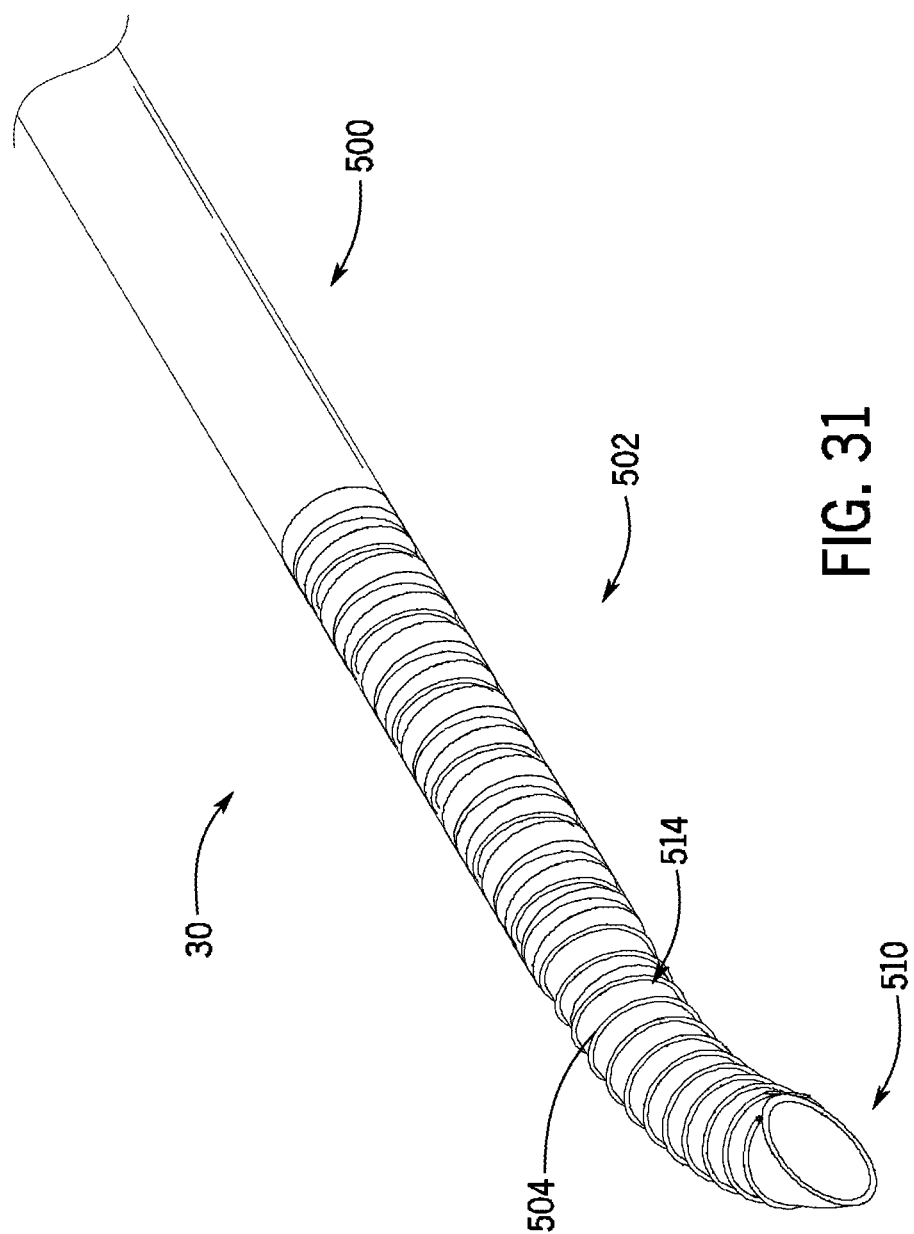
FIG. 31 is a view of the distal portion of the outflow conduit according to one embodiment.

In certain embodiments, at least a portion of the inflow conduit 20 and outflow conduit 30 are preferentially reinforced to resist kinking and compression. For example, the conduits 20 and 30 may be reinforced with nitinol or another shape memory alloy or self-expanding or radially expansive material. Preferably, a layer of braided nitinol is wrapped around at least a portion of each of the conduits 20 and 30 or incorporated into the walls of conduits. In one embodiment, the inflow conduit 20 is reinforced by braided nitinol incorporated into the walls of the conduit. In another embodiment, the inflow conduit may be reinforced by braided stainless steel that is incorporated into the wall of the conduits 20 and 30. Alternately, a coil of nitinol or PTFE may be wrapped around portions of the conduits 20 and 30 or incorporated therein. For example, as shown in FIG. 31, the distal segment 502 of the outflow conduit 30 has a PTFE coil 504 incorporated around the ePTFE conduit forming the wall 514 of the conduit. In other embodiments, a coil of nitinol may be wrapped around portions of the conduits 20 and 30 or incorporated therein.

The braid density of the braided nitinol incorporated into both the inflow and the outflow conduits 20 and 30, commonly measured in pixels per inch ("PPI"), is typically between about 10 and 200, and preferably between about 20 and about 60. In various embodiments, the braid density may vary along the lengths of the inflow and the outflow conduits 20 and 30. For example, the braid density may be greater in portions of the conduits 20 and 30 adjacent to the blood pump 25, in order to maintain greater stiffness of the conduits and minimize the risk of external conduit compression or conduit collapse during suction, while allowing for more flexibility in different segments of the conduits.

Figure 32B:
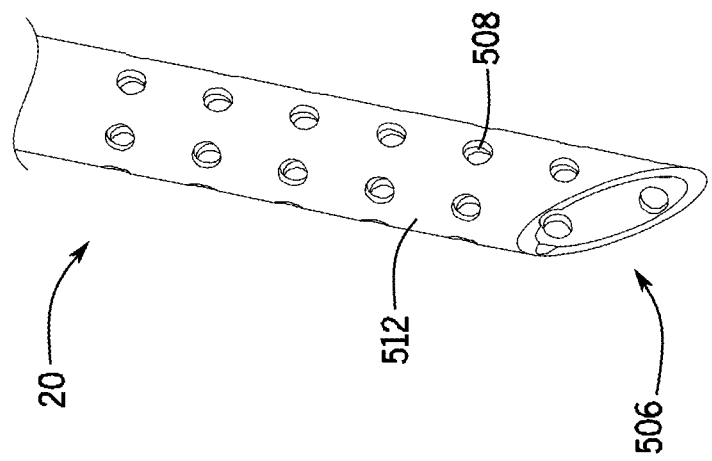
FIGS. 32A and 32B are views of the intravascular portion of an inflow conduit according to one embodiment.
Figure 32A:
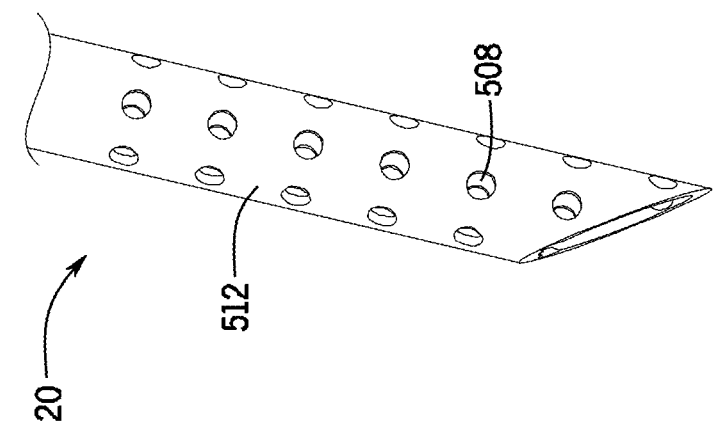
Figure 33:
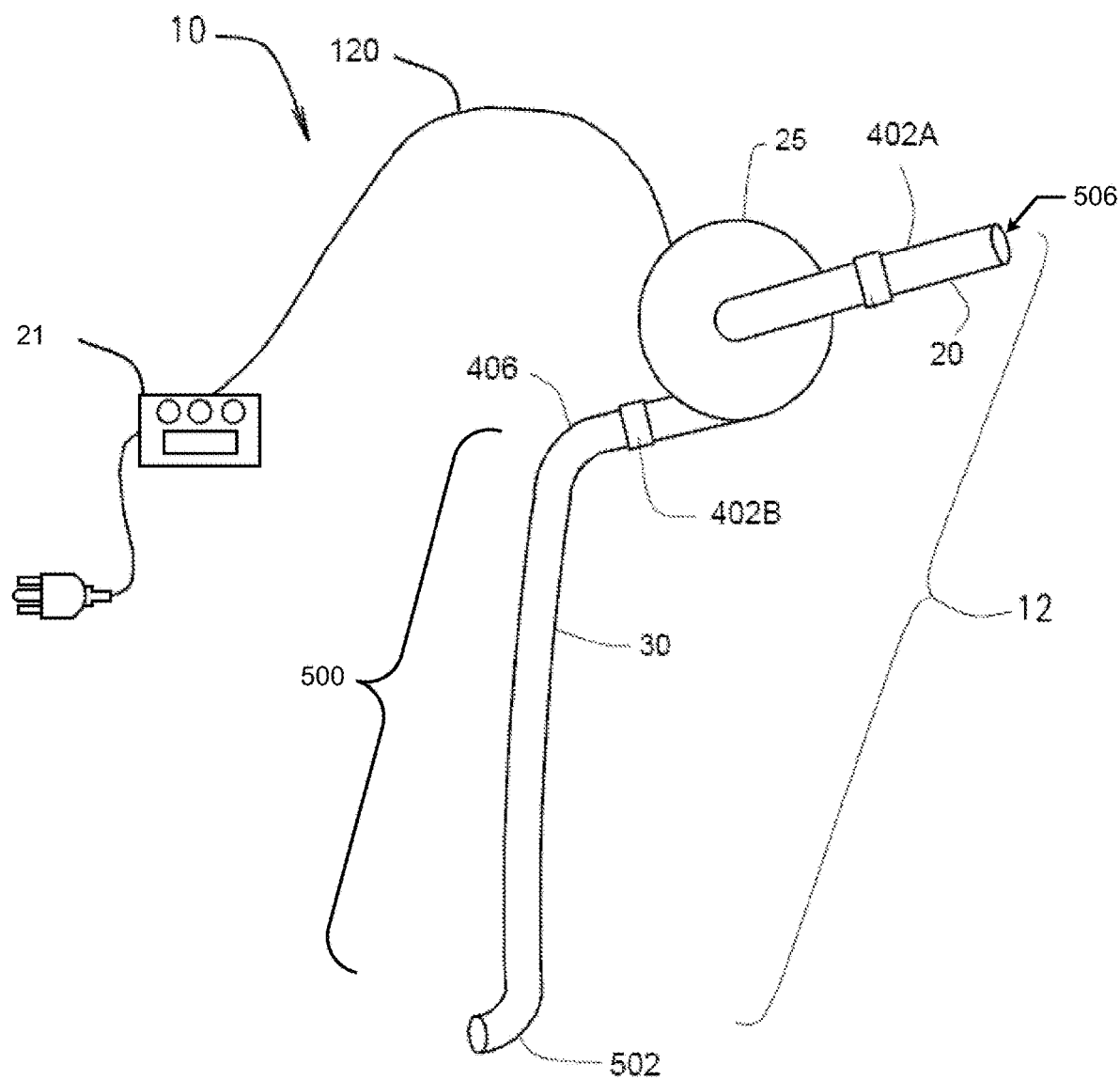
FIG. 33 is a schematic view of the pump system according to one embodiment.

In one embodiment, as shown in FIGS. 32A-32B, the intravascular portion 506 of the inflow conduit 20 is fenestrated by means of multiple side holes 508. These side holes enhance blood inflow and reduce the risk of suction of the vein or right atrium wall by the end hole in the event of partial obstruction of the conduit tip. Preferably, the side holes 508 are circular and range in diameter from 0.5 mm to 1.5 mm. In other embodiments, however, the side holes 508 may be elliptical or any other shape and size suitable for the intravascular aspiration of blood.

As shown in FIGS. 31 and 32A-32B, the distal end 506 of the inflow conduit 20 and the distal end 510 of the outflow conduit 30 may be cut and chamfered at an angle between 10° and 80°. In certain embodiments, the chamfer reduces the risk of suction of the vein or right atrium wall by the end hole in the event of partial obstruction of the tip of the conduit during aspiration of blood. In other embodiments, the chamfer increases the area of the conduit as it joins the vascular system in an anastomotic connection. Preferably, but without limitation, the distal ends 506 and 510 are chamfered at 45°. The inflow and outflow conduits 20 and 30 are adapted for ease of insertion, subcutaneous tunneling, and removal, while also providing a resistance to infection and thrombosis.

In one embodiment, a portion of the inflow conduit 20 may be inserted into the lumen of a blood vessel and advanced to the desired position using a percutaneous approach or an open surgical approach. To aid in the positioning of the inflow and outflow conduits 20 and 30, the conduits may have radiopaque marker bands or other radiopaque materials embedded within the walls 512 and 514 of the inflow and outflow conduits, respectively, that are visible under fluoroscopy. For example, portions of the inflow and outflow conduits 20 and 30 may be composed of Carbothane® PC-3575 polyurethane embedded with barium sulfate salts. In other embodiments the portions of the inflow and outflow conduits 20 and 30 that are configured to be inserted into the lumen of the vascular system may have self-expanding or radially expansive (such as can be accomplished by incorporating nitinol) walls so that the diameter of the intravascular portion of the inflow and outflow conduits 20 and 30 will match the diameter of the vascular system at that location, such as is seen with the self expanding segment of the GORE® Hybrid Vascular Graft.

Figure 37:
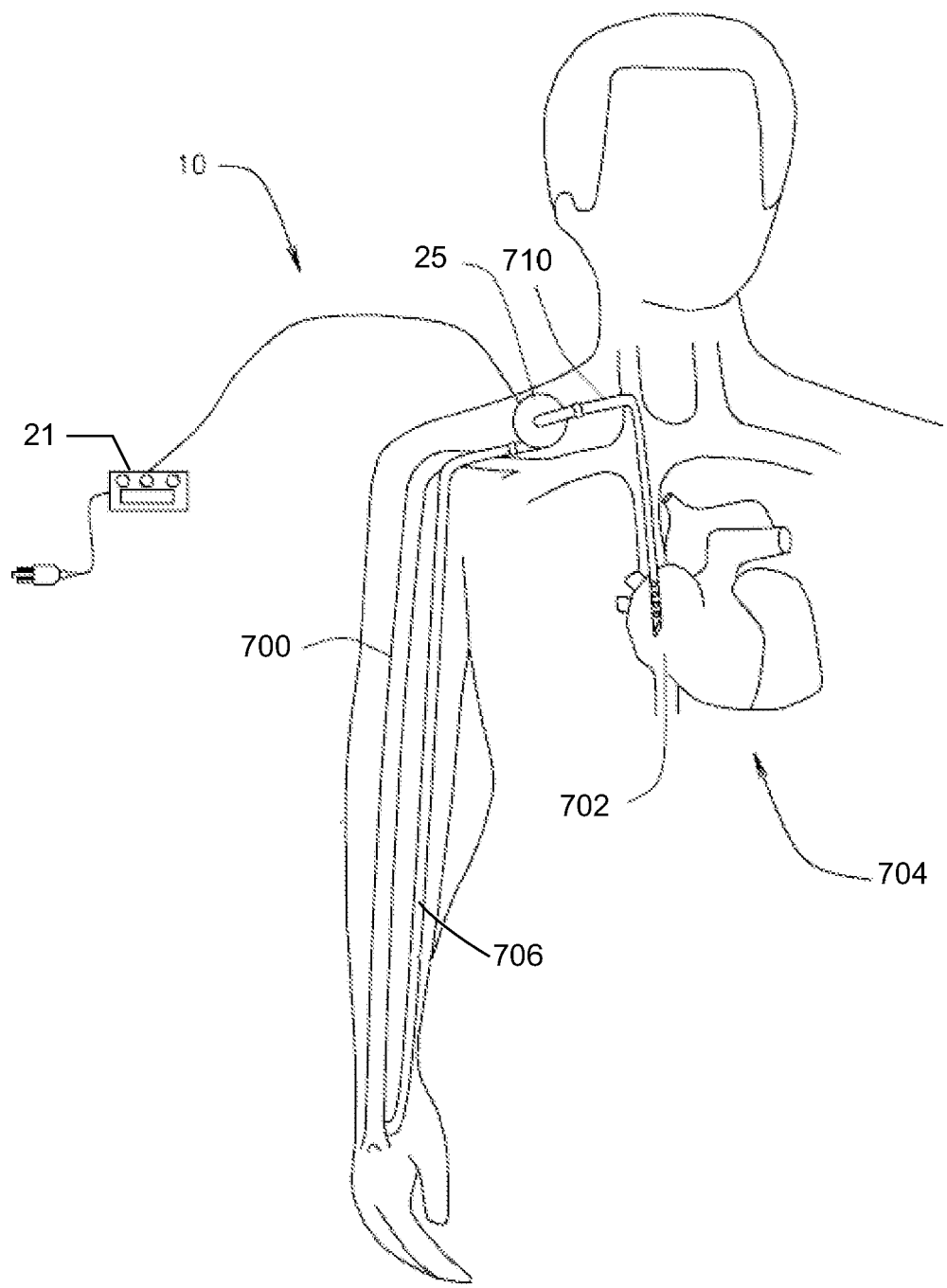
FIG. 37 is a schematic view of the pump system as applied to a circulatory system of a patient according to one embodiment.

In various embodiments, including the embodiment shown in FIG. 37, the inflow and outflow conduits 20 and 30 may be attached to blood vessels using a surgical anastomosis, using suture in a running or divided fashion, henceforth described as an "anastomotic connection." An anastomotic connection can also be made with surgical clips and other standard ways of making an anastomosis. For example, an anastomotic connection may be made between the ePTFE distal segment 502 of the outflow conduit 30 and a blood vessel.

In certain embodiments where an anastomotic connection is made, the outflow conduit 30 is secured to blood vessels having an initial diameter between 1 mm and 20 mm, and preferably vessels having an initial diameter between 1 mm and 6 mm.

Conversely, in other embodiments shown in FIGS. 32A-B and 37-40, portions of the inflow and outflow conduits 20 and 30 are placed within a blood vessel or the right atrium. For example, the distal end 506 of the inflow conduit 20 may be positioned within the right atrium or the superior vena cava. As shown in FIGS. 32A-32B, the side holes 508 aid in the aspiration or discharge of blood when the distal end 506 has been placed intravascularly.

In various other embodiments, at least one of the inflow and outflow conduits 20 and 30 may be compatible for use with a hemodialysis machine. For example, a patient using the blood pump system 10 may also need to receive a hemodialysis treatment. In this example, blood may be withdrawn from the blood pump system, passed through a hemodialysis machine, and then discharged back into the blood pump system for delivery back into the vascular system, thereby eliminating the need to create an additional vascular access site in the patient.

Figure 35:
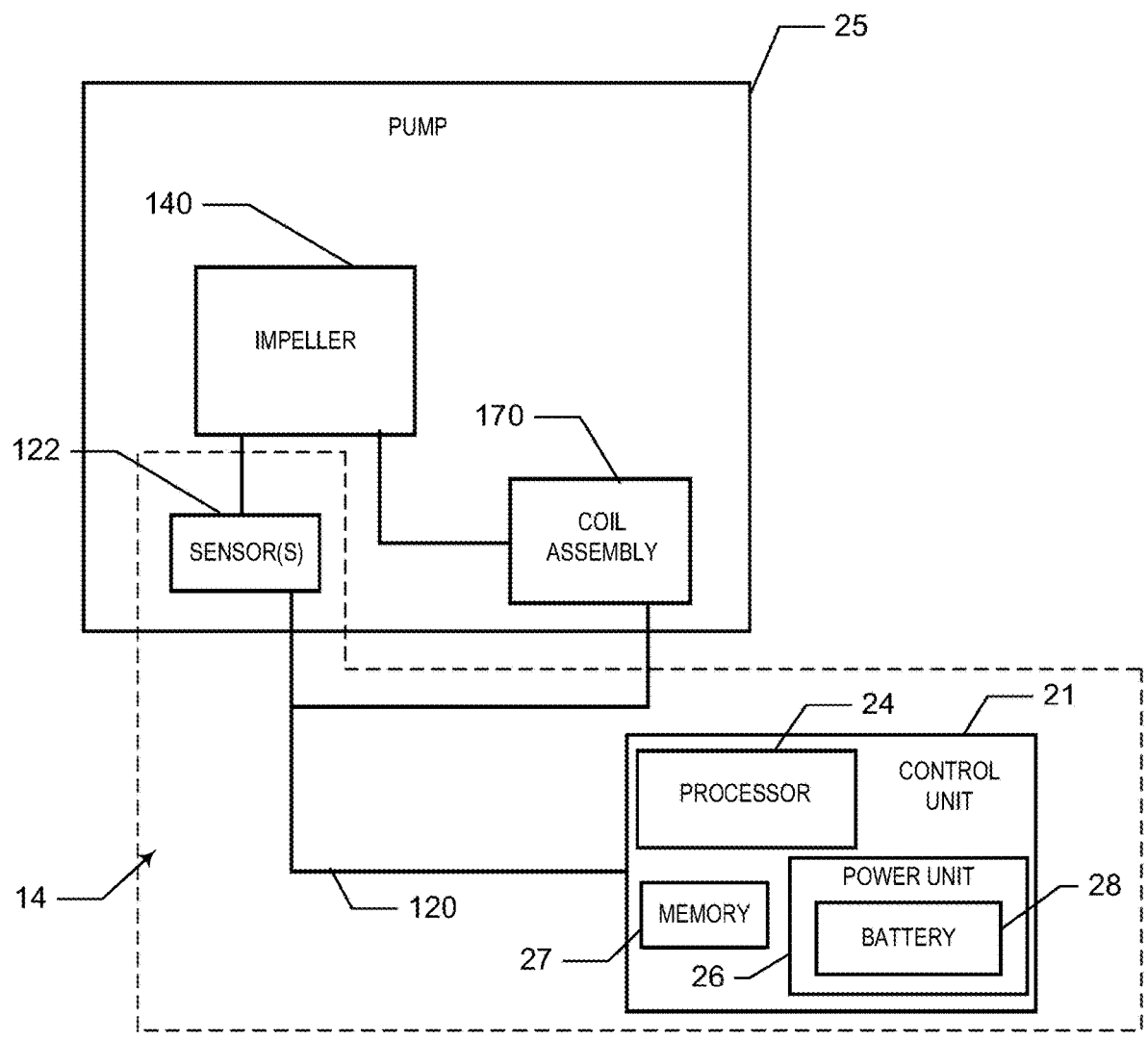
FIG. 35 is a schematic view of a control systems according to one embodiment.

As shown in FIG. 35, one embodiment of the control system 14 includes a control device 21 having at least one processor 24 and memory 27 for delivering power to the pump and receiving information from the blood pump 25, whereby the information is used to set and control pump speed and estimate the flow rate of fluid through the pump system. The processor 24 is configured to read, process, and execute systems, methods, and instructions encoded on a computer-readable medium. The control system 14 then estimates the wall shear stress in the target vessel using the measured or estimated vessel diameter and the measured or estimated average flow rate of the pump system. The control device also includes a power source 26, optionally having a battery 28.

In one embodiment, the control system 14 receives sensor feedback from one or more sensors 122. Any of a variety of suitable sensors may be used to detect any of a variety of changes in a physical quantity of the blood, blood pump 15, the blood pump system 10, and/or the target vessel. The sensors 122 generate a signal indicative of the change to be analyzed and/or processed. Essentially, the sensors 122 monitor a variety of properties of the blood pump system 10, the blood flowing through the system, and the target blood vessel for changes that can be processed and compared to desired reference values or predetermined standards. The desired reference values or predetermined standards may be stored in a database or other suitable medium.

In various embodiments, one or more sensors 122 may be in communication with the blood pump 25, the inflow conduit 20, the outflow conduit 30, the donating vessel or location, or the accepting vessel or location. In various embodiments, the control system 14 or portions thereof may be located internally within the housing or casing of the blood pump 25. For example, one or more of the sensors 122 may be located in the inlet 110 or outlet 115 of the blood pump 25. In other embodiments, the control system 14 may be external to the pump.

Wall shear stress can be used as a variable to configure the operation of the pump system 10 to result in an increase in the overall diameter and lumen diameter of the target vessel or an increase in the length of the target vessel.

Assuming Hagen-Poiseuille blood flow (i.e. laminar flow with a fully developed parabolic velocity profile) in the lumen of a vessel having a circular cross section, then WSS can be determined using the equation:

$$WSS(Pa) = 4Q\mu/\pi R^3 \qquad [\text{Eqn. 1}]$$

where:
Q=flow rate (m$^3$/s)
μ=viscosity of blood (Pa·s)
R=radius of vessel (m)

Wall Shear Stress Control Method #1: Manual

Figure 36A:
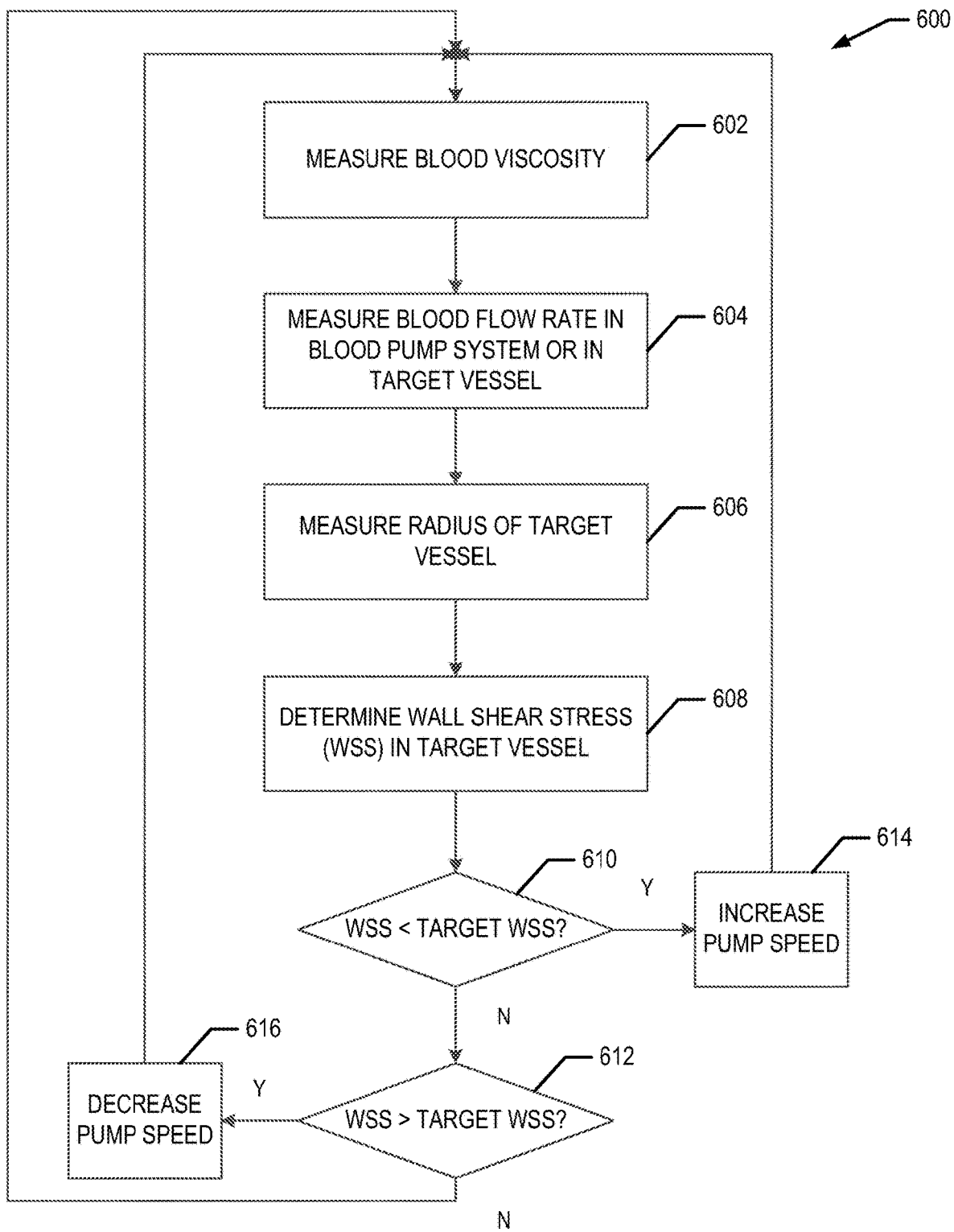
FIGS. 36A-36D are flowcharts of control system methods according to various embodiments.

Mean and/or peak WSS in the target blood vessel can be controlled by adjusting pump speed, which affects the blood flow rate through the pump-conduit system and therefore blood flow through the target vessel. As shown in FIG. 36A, a manual control method 600 may involve the direct measurement of blood viscosity at block 602 (by sampling the patient's blood and analyzing it in a viscometer), blood flow rate in the blood pump system or blood flow rate in the target vessel at block 604 (by placement of an ultrasonic flow sensor on either the inflow or outflow conduit or by ultrasound or thermal dilution methods, respectively) and vessel radius at block 606 (by various imaging methods including angiography, ultrasound, computed tomography, or magnetic resonance imaging). The WSS acting on the vessel wall is determined at block 608, compared to the desired level at blocks 610 or 612, and then the pump flow rate (Q) is adjusted through changes in the rotational speed of the pump impeller at blocks 614 or 616. Changes in pump speed are effected by varying the duty-cycle of the pulse width modulation of the motor input voltage.

Figure 36B:
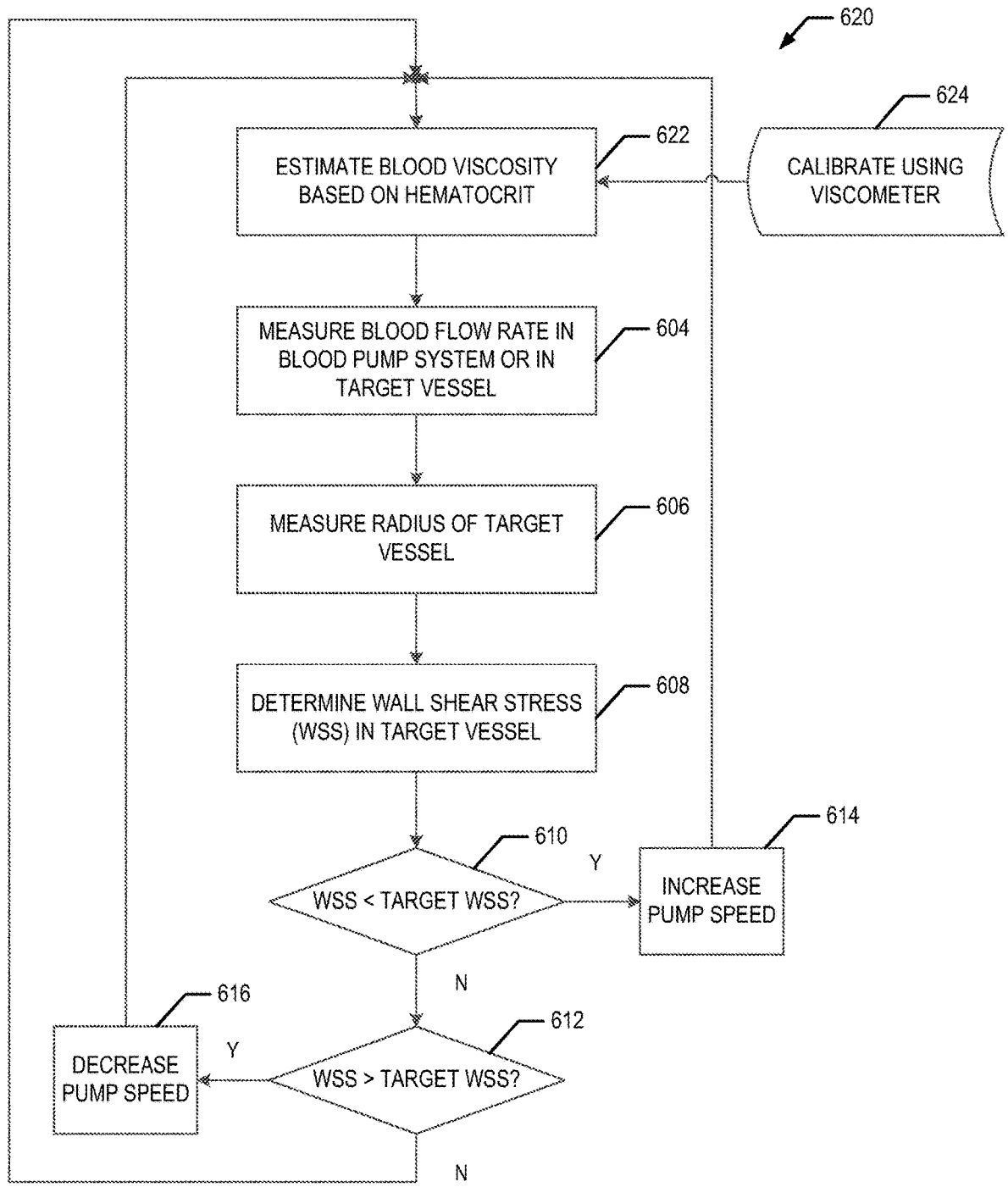
Figure 36C:
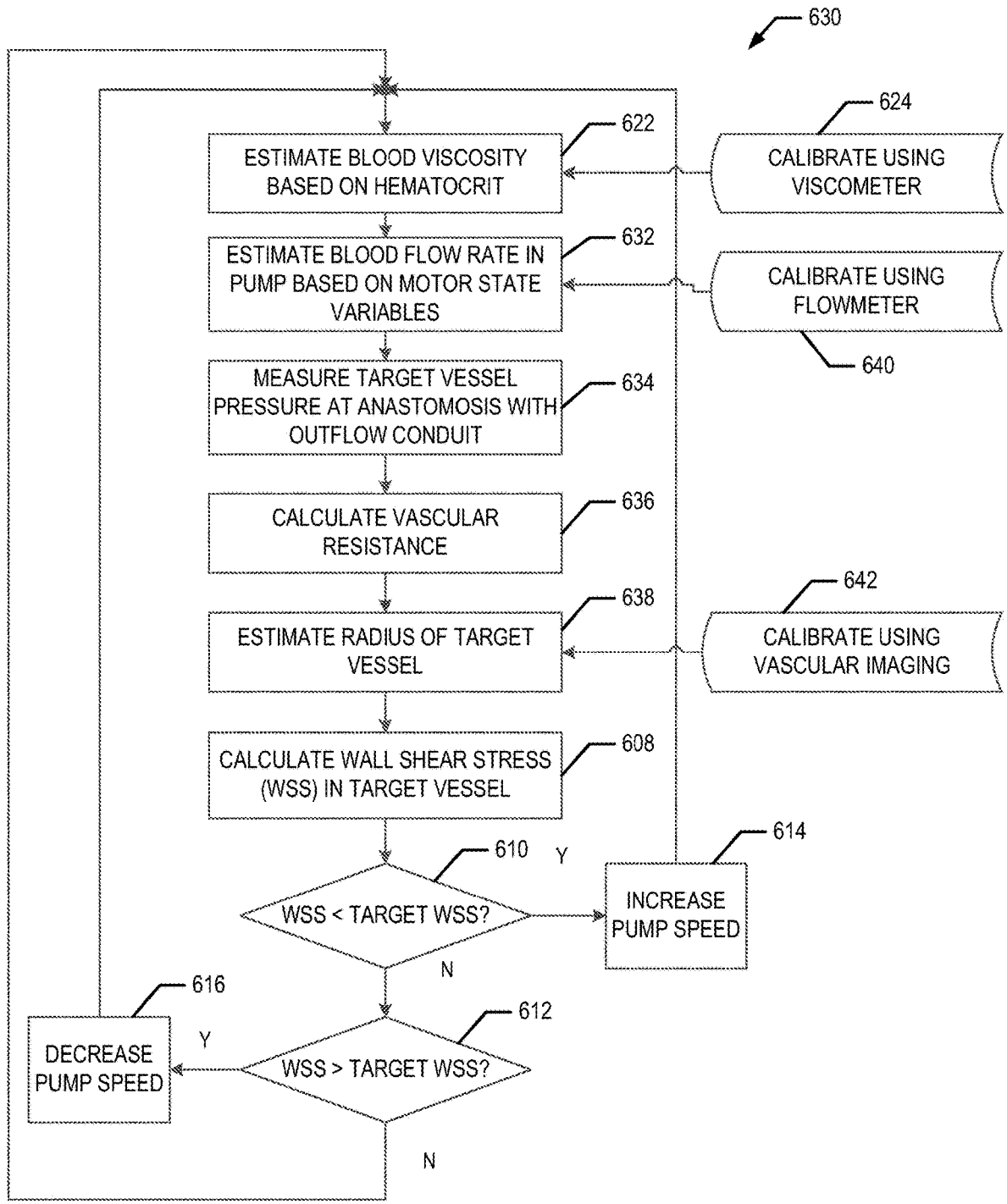

Wall Shear Stress Control Method #2: Automatic with Indirect Blood Viscosity, Direct Blood Flow, and Target Blood Vessel Diameter Measurements An automatic WSS control system may involve direct measurement of blood flow rate in the pump system or the target vessel, and direct measurement of the diameter of the target vessel blood vessel. As shown in FIG. 36B, this automatic WSS control method 620 may involve indirect measurements of blood viscosity at block 622 (estimated based on its known relationship with measured hematocrit and approximate mean WSS). Periodic calibration of the viscosity estimator at block 624 may be performed using direct measurements of viscosity as previously described. In clinical practice, the blood viscosity usually varies slowly.
Wall Shear Stress Control Method #3: Automatic with Indirect Blood Viscosity, Blood Flow, Target Blood Vessel Diameter Measurements, and Direct Vein Pressure Measurements As shown in FIG. 36C, an automatic WSS control method 630 may involve indirect measurements of blood viscosity (estimated based on its known relationship with measured hematocrit and approximate mean WSS) at block 622, blood flow rate through the blood pump system (estimated based on its relationship to motor state variables) at block 632, measurements of the target blood vessel pressure at block 634, and measurements of the vessel radius (estimated based on vascular resistance) at block 638. Vascular resistance is calculated at block 636 based on the estimated pump flow rate and the measured blood pressure in the vessel. Periodic calibration of the blood viscosity, pump flow, and target vessel radius estimators respectively, may be performed using direct measurements at blocks 624, 640, and 642, respectively, as previously described.

Figure 36D:
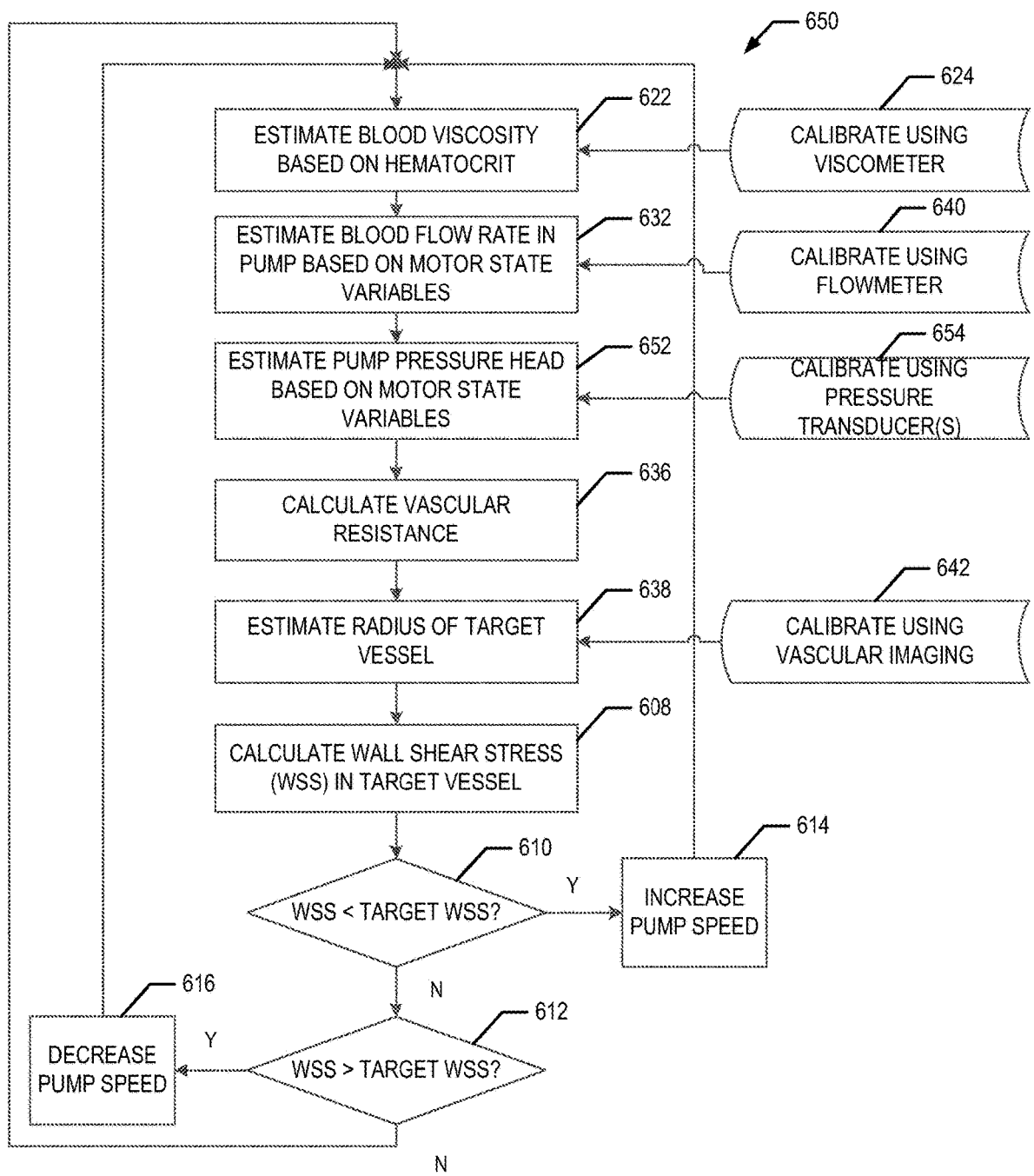

Wall Shear Stress Control Method #4: Automatic with Indirect Blood Viscosity, Blood Flow, Pump Pressure Head, and Target Blood Vessel Diameter Measurements As shown in FIG. 36D, an automatic WSS control method 650 may involve indirect measurements of blood viscosity (estimated based on its known relationship with measured hematocrit and approximate mean WSS) at block 622, blood flow rate through the blood pump system (estimated based on its relationship to motor state variables) at block 632, and vessel radius (estimated based on vascular resistance) at block 638. Vascular resistance is calculated at block 636 based on the pump flow rate estimated at block 632 and pump pressure head, where pump pressure head is also estimated at block 652 based on its relationship to motor state variables. Periodic calibration of the blood viscosity, pump flow, and target vessel radius estimators may be performed using direct measurements at blocks 624, 640, and 642, respectively, as previously described. Periodic calibration of the pump pressure head estimator may be performed by measuring pump inlet and pump outlet pressures with separate pressure transducers and calculating their difference at block 654, or by directly measuring pressure head across the pump with a differential pressure sensor.

Sensorless Determination of Blood Pump System Flow Rate and Pressure Head:

Referring to FIG. 35, the processor 24 is adapted to detect and monitor electric current appearing in one or more of the electric coils of the coil assembly 170 of the pump via the power cable 120 which, in conjunction with monitoring the voltage provided to the coil assembly permits the processor 24 to derive the input power ($P_{in}$) consumed by the blood pump 25 and an actual rotational speed of the impeller 140 ($\omega$). The processor 24 can estimate pump flow rate (Q) or changes in flow rate ($\Delta Q$) as a function of Pin and w. For example, $Q=f[P_{in}, \omega]$. More specifically, the following equation is used:

$$Q = a + b \cdot \ln(P_{in}) + c \cdot \omega^{0.5} \quad \text{[Eqn. 2]}$$

where:
 Q=flow rate (L/min)
 $P_{in}$=Motor input power (W)
 $\omega$=Pump speed (rpm)

Motor input power is derived from the measured motor current and voltage. The values for a, b, and c are derived from curve fitting the plot of pump flow rate as a function of motor speed and input power.

The processor 24 can also estimate pump pressure head ($H_p$) or changes in pump pressure head ($\Delta H_p$) as a function of $P_{in}$ and $\omega$. For example, $H_p = f[P_{in}, \omega]$. More specifically, the following equation is used:

$$H_p = d + e \cdot \ln(P_{in}) + f \cdot \omega^{2.5} \quad \text{[Eqn. 3]}$$

The values for d, e, and f are derived from curve fitting the plot of pump pressure head as a function of pump speed and motor input power, where $H_p$ is measured across the inflow conduit 20, pump 25, and outflow conduit 30.

Determination of Vascular Resistance and Estimation of Vessel Radius:

Vascular resistance (Rv) is the resistance to flow that must be overcome to push blood through the circulatory system. Resistance is equal to driving pressure ($H_v$) divided by the flow rate. When the blood pump system is connected to a target vessel that is a vein, the vascular resistance is calculated using the following equation:

$$R_v = (P_v - \text{CVP})/Q \quad \text{[Eqn. 4]}$$

where:
 $H_v$=pressure head lost across the peripheral vessel on the return path of the blood to the heart (mmHg)
 $P_v$=vein pressure at anastomosis (mmHg)
 CVP=central venous pressure (mmHg)
 $R_v$=vascular resistance ((mmHg min)/L)

Figure 36E:
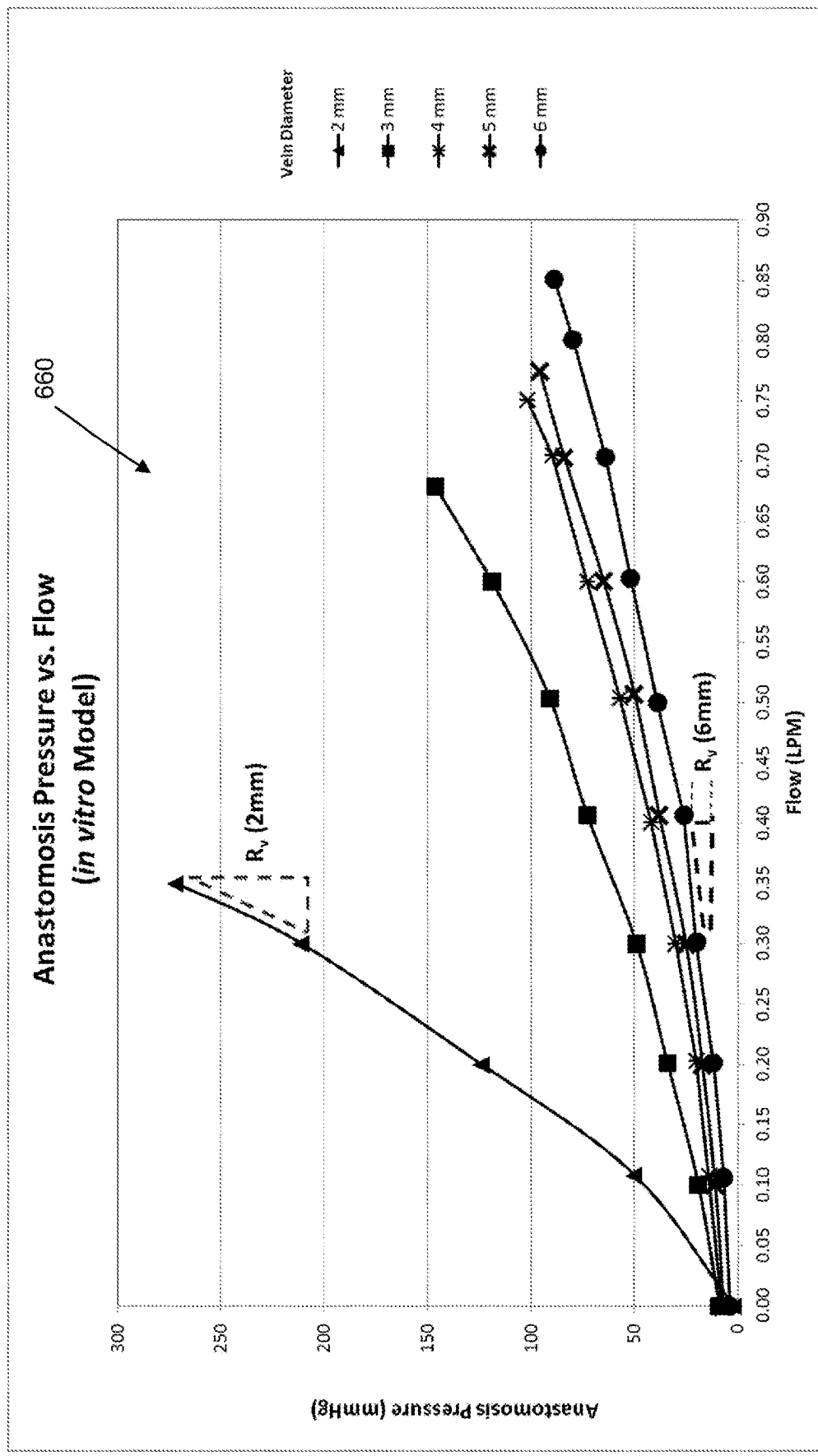
FIG. 36E is a plot of anastomosis pressures and blood flow rates for an in vitro model of the pump system according to one embodiment.

Normally, CVP ranges between 2-8 mmHg and can be neglected in the above equation because the operating ranges of $P_v$ and Q are proportionally much greater. As illustrated in FIG. 36E, vascular resistance can be represented graphically as the slope of various $P_v$ vs. Q curves 660. Since the curves 660 are nonlinear, the slope is a function of Q. As illustrated by the following equation, the vascular resistance may be derived by temporarily increasing speed by several hundred rpm ($\Delta \omega$), measuring the resulting change in vein pressure ($\Delta P_v$), and estimating the resulting change in pump flow ($\Delta Q$):

$$R_v(Q) = \Delta P_v / \Delta Q \quad \text{[Eqn. 5]}$$

It is noted that the vascular resistance is a strong function of vessel diameter or radius, with smaller veins having high vascular resistance. Vascular resistance can be quantified in various units, for example, Wood units ((mmHg·min)/L) can be multiplied by eight to convert to SI units ((Pa·s)/m³).

Alternatively, pump pressure head ($H_p$) may be used as a basis for calculating vascular resistance. When the pump-conduit system is configured to withdraw blood from one location in the vascular system to discharge it into a peripheral artery or vein it is a reasonable assumption that the pressure head gained across the system (Hp) is exactly equal to the pressure head lost across the peripheral vessel on the return path of the blood to the heart ($H_v$):

$$H_v = H_p \quad \text{[Eqn. 6]}$$

The radius of the peripheral vessel is inversely proportional to its vascular resistance ($R_v$), the ratio of $H_v$ to Q. Assuming Hagen-Poiseuille blood flow in the vessel of circular cross section, the vascular resistance can be represented using the equation:

$$R_v(\text{Pa·s/m}^3) = P_v/Q = 8 \cdot \mu \cdot L / \pi \cdot R^4 \quad \text{[Eqn. 7]}$$

where:
 $P_v$ is expressed in units of Pa
 Q is expressed in units of (m³/s)

μ=viscosity of blood (Pa·s)
R=radius of vessel (m)
L=length of vessel (m)

In practice, Eqn. 7 would be refined based upon in vivo measurements of pressure drop across specific veins of known diameter. This provides an empirical form of the equation:

$$R_v(Pa \cdot s/m^3) = K \cdot \mu / R^4 \quad [\text{Eqn. 8}]$$

where:
K is an empirical constant for the target vein (m)

Determination of Wall Shear Stress:

The wall shear stress in the target vessel can be determined based on the above equations. Using Eqn. 4, the pump flow rate can be expressed according to the following equation:

$$Q = P_v / R_v \quad [\text{Eqn. 9}]$$

Using Eqn. 8, vessel radius can be expressed according to the following equation:

$$R = (K \cdot \mu / R_v)^{0.25} \quad [\text{Eqn. 10}]$$

Using Eqns. 1, 9, and 10, the wall shear stress can be expressed according to the following equation:

$$WSS(Pa) = ((4 \cdot P_v)/(\pi \cdot K^{0.75})) \cdot (\mu / R_v)^{0.25} \quad [\text{Eqn. 11}]$$

In various embodiments, the estimated variables used by the control system are periodically calibrated. For example, the estimates of flow rate and pressure head are periodically calibrated using actual measured values at an interval ranging from 1 minute and up to 30 days. Similarly, the estimate of artery or vein radius is periodically calibrated using actual measured values at an interval ranging from 1 minute and up to 30 days.

Figure 36F:
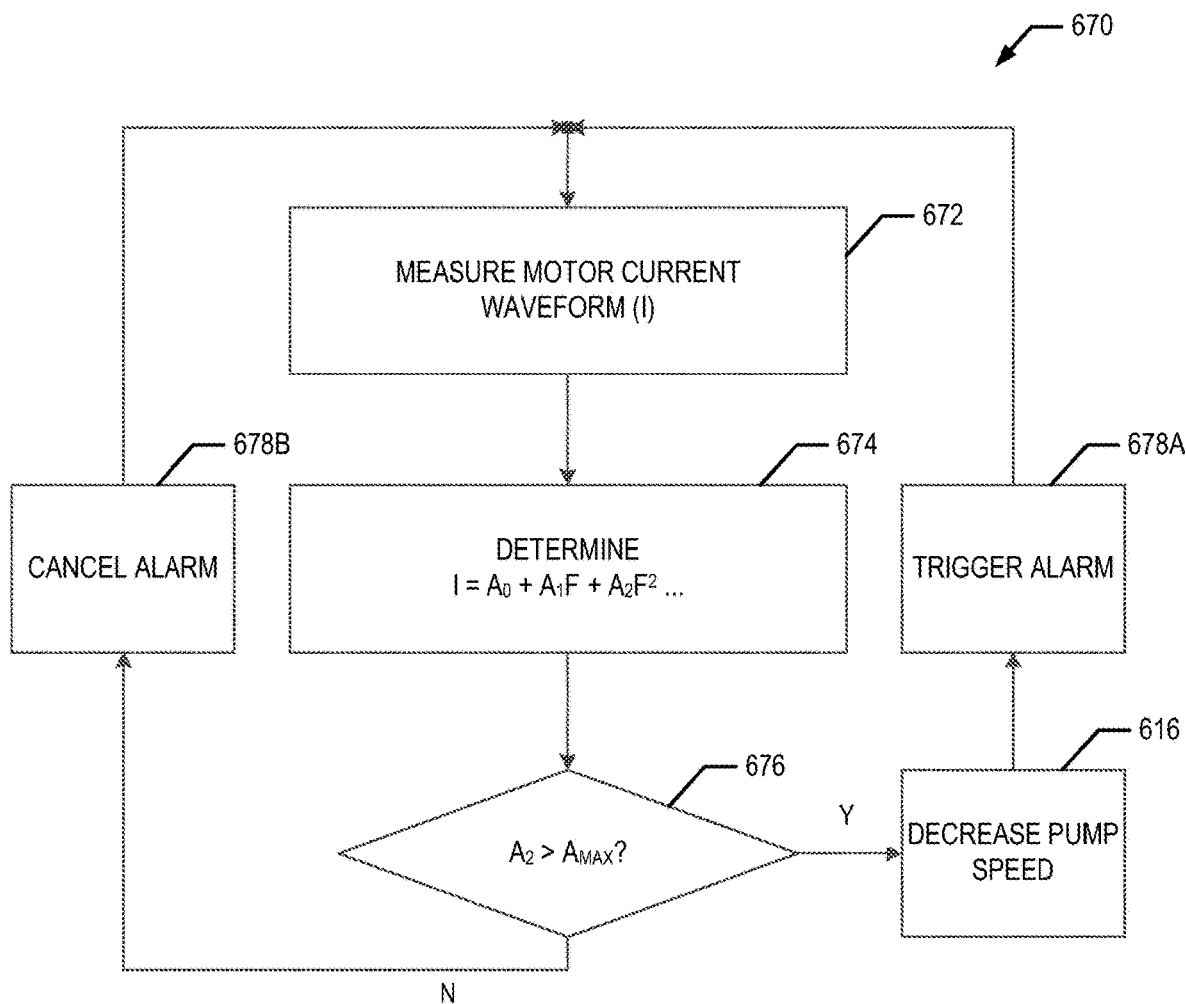
FIGS. 36F-36H are flowcharts of control system methods according to various embodiments.

Safety Features and Alarms:

The automatic control system may also include safety features to avoid hazards associated with changes in the patient's cardiovascular system or malfunctions of the pump system or pump control system. As shown in FIG. 36F, a speed control method 670 can detect characteristic changes in the motor current waveform associated with decreased preload or increase in afterload (e.g. due to thrombosis), suction, flow limitation, and imminent collapse of the vessel around the inflow conduit tip at block 672. Spectral analysis of the motor current waveform is performed using a Fourier transform at block 674. When the amplitude of the second harmonic term of the Fourier series exceeds a predetermined value at block 676, suction has occurred and collapse is deemed imminent. Pump speed is immediately decreased at block 616 and an alarm is triggered at block 678A within the control device 21. When normal operation is restored, the alarm is canceled at block 678B.

Figure 36G:
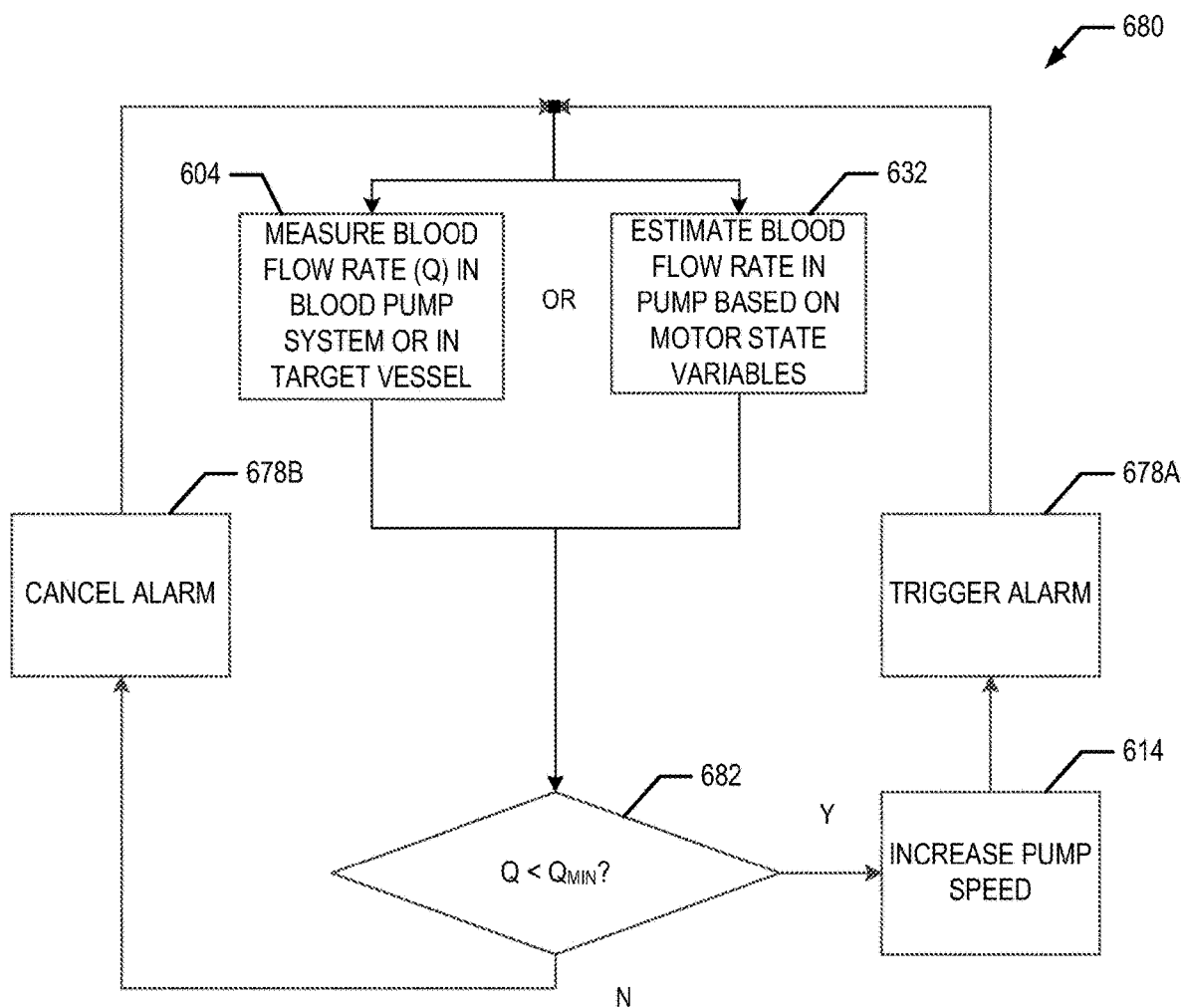

As shown in FIG. 36G, a speed control method 680 can detect low flow conditions. When the pump flow rate drops below the safe threshold level to avoid thrombosis of the pump-conduit system 10 at block 682, the pump speed is immediately increased at block 614 and an alarm is triggered at block 678A within the control device 21. When normal operation is restored, the alarm is canceled at block 678B.

Figure 36H:
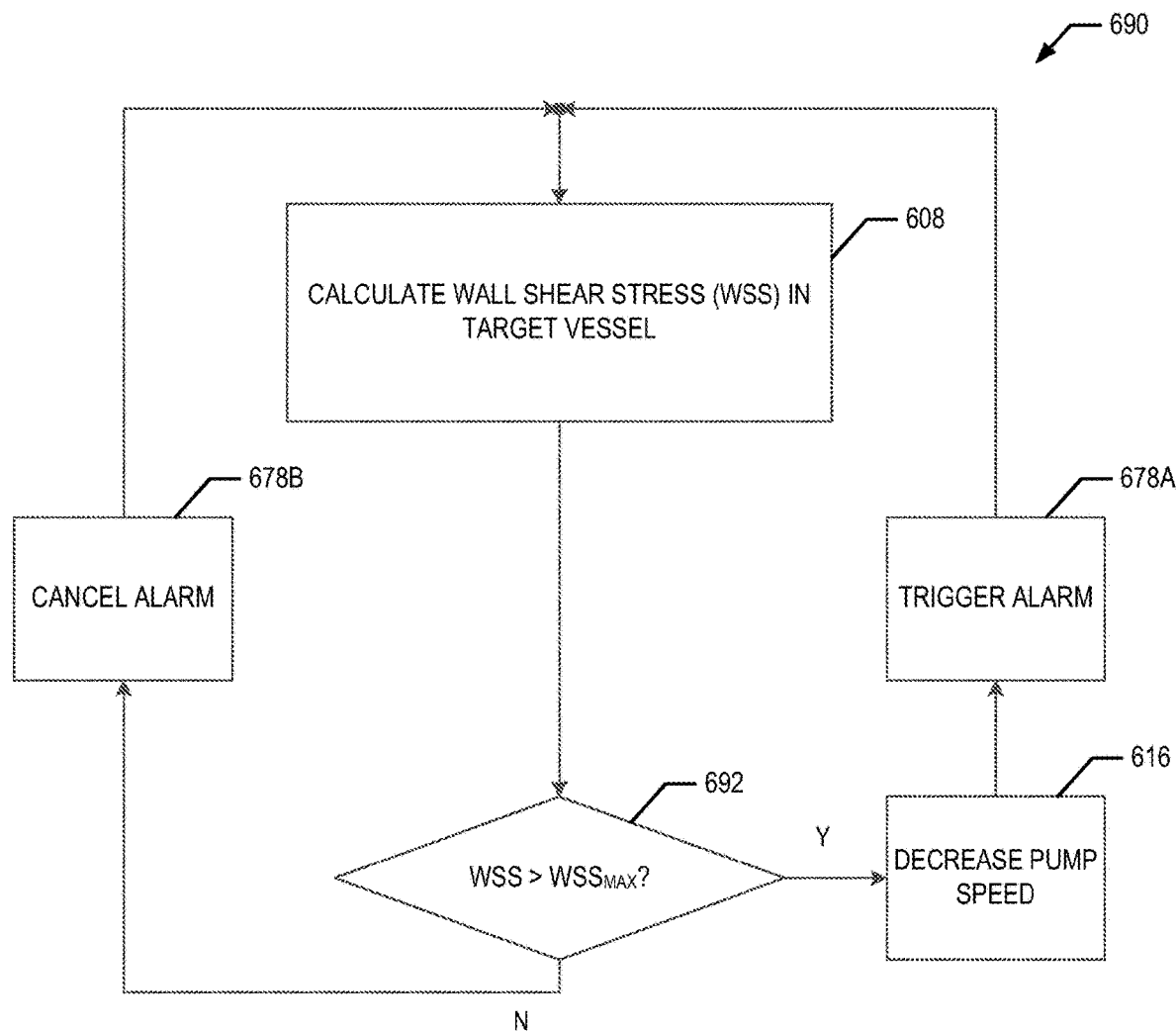

As shown in FIG. 36H, a speed control method 690 can detect high wall shear stress conditions. When the WSS rises above the safe threshold level to avoid damage to the vessel endothelium at block 692, the pump speed is immediately decreased at block 616 and an alarm is triggered at block 678A within the control device 21. When normal operation is restored, the alarm is canceled at block 678B.

In yet another embodiment in which the inflow conduit 20 is connected to an artery and the outflow conduit 30 is connected to a vein, the control system 14 monitors and modifies the pulsatility of blood flow that is discharged into the accepting vein. For example, the control system 14 can monitor the electrocardiogram or monitor the cyclic changes in the pulse wave of blood coming into the blood pump system. During ventricular contraction and pulse wave propagation, the control system can decrease the rotational speed of the pump. During systole and after the pulse wave has passed, the control system can increase the rotational speed of the pump. In this manner, pulsatility in the blood entering the accepting vein can be reduced. Alternatively, the pulsatility of the blood in the accepting vein may be periodically checked manually, as may be accomplished with ultrasound, and the pump may be manually adjusted, for example, by tuning the head-flow characteristics of the pump, adding a compliance reservoir or elastic reservoir (a segmental or a diffuse change) to the pump inflow or outflow, or modulating the pump speed. Other adjustments may also be made. Alternatively, a compliance reservoir or elastic reservoir can be added to the inflow or outflow conduits at the time of implantation of the blood pump system.

In various other embodiments, the control system 14 is monitored and adjusted manually or with a software program or application encoded on a computer-readable medium and executable by the processor 24, or other automated systems. The computer-readable medium may include volatile media, nonvolatile media, removable media, non-removable media, and/or another available medium that can be accessed by control system 14. By way of example and not limitation, the computer-readable medium may include computer storage media and communication media. Computer storage media includes memory, volatile media, nonvolatile media, removable media, and/or non-removable media implemented in a method or technology for storage of information, such as computer readable instructions, data structures, program modules, or other data.

The software program may include executable instructions to automatically adjust the pump speed to maintain the desired amount of blood flow, mean blood speed or velocity, and mean WSS in the vessel segment to be treated (the "target vessel" or the "target blood vessel") in which a persistent increase in overall diameter and lumen diameter, or length, is desired, whether it is a donating artery, a donating vein, an accepting artery, or an accepting vein. Alternatively, the overall diameter, lumen diameter, length, and blood flow in the target vessel may be periodically checked manually, as may be accomplished with ultrasound, and the pump may be manually adjusted, for example, by tuning the head-flow characteristics of the pump or modulating the pump speed. Other adjustments may also be made.

In one embodiment, the mean blood speed is determined by calculating an average of multiple discrete measurements of blood speed by summing the discrete measurements and dividing the total by the number of measurements. Mean blood speed can be calculated by taking measurements over a period of milliseconds, seconds, 1 minute, 5 minutes, 15 minutes, 30 minutes, 1 hour, or multiple hours.

In another embodiment, the mean WSS is determined by making a series of discrete measurements, making multiple discrete determinations of WSS (using those measurements), summing the discrete WSS determinations, and dividing the total by the number of determinations. Mean WSS can be calculated by taking measurements and making discrete WSS determinations over a period of seconds, 1 minute, 5 minutes, 15 minutes, 30 minutes, 1 hour, or multiple hours.

In one embodiment, the control system 14 receives information from sensor 22 in communication with the blood pump 25. In other embodiments, the control system 14 receives information from a sensor 22 in communication with an inflow conduit 20 or an outflow conduit 30 or in a vessel in fluid communication the inflow or outflow conduit. In various embodiments, all or portions of the control system 14 may be located within the pump body 25, while in other embodiments all or a portion of the control system may be located within the conduits, or within the control device 21.

The systems and methods described herein increase the mean WSS level in peripheral veins and arteries. Normal mean WSS for veins ranges between 0.076 Pa and 0.76 Pa. The systems described herein are configured to increase the mean WSS level in the accepting peripheral vein to a range between 0.76 Pa and 23 Pa, preferably to a range between 2.5 Pa and 10 Pa. Normal mean WSS for arteries ranges between 0.3 Pa and 1.5 Pa. For artery dilation, the systems and methods described herein increase the mean WSS level to a range between 1.5 Pa and 23 Pa, preferably to a range between 2.5 Pa and 10 Pa. In certain instances, sustained mean WSS less than 0.76 Pa in veins or less than 1.5 Pa in arteries may increase the overall diameter and lumen diameter of these vessels but the extent and rate of this increase is not likely to be clinically meaningful or compatible with routine clinical practice. Sustained mean WSS greater than 23 Pa in arteries or veins is likely to cause denudation (loss) of the endothelium of the blood vessels, or damage to the endothelium, which is known to retard dilation of blood vessels in response to increases in mean blood speed and mean WSS. Pumping blood in a manner that increases mean WSS to the desired range for preferably 1 day to 84 days, and more preferably between about 7 and 42 days, for example, produces a persistent increase in the overall diameter and lumen diameter in an accepting vein, a donating vein, or a donating artery such that veins and arteries that were initially ineligible or suboptimal for use as a hemodialysis access sites or bypass grafts due to small vein or artery diameter become usable or more optimal. The blood pumping process may be monitored and adjusted periodically. For example, the pump may be adjusted over a period of minutes, hours, 1 day, 3 days, 1 week, or multiple weeks to account for changes in the peripheral vein or artery (such as a persistent increase in the overall diameter and lumen diameter) prior to achieving the desired persistent dilation.

Referring to FIGS. 37-40, a system 10 to increase the overall diameter and lumen diameter of veins and arteries is illustrated as used for a patient 1. In FIG. 37, the system 10 draws deoxygenated venous blood from the patient's venous system and discharges that blood into the accepting peripheral vessel 700. The system 10 also increases the mean speed of blood in the accepting peripheral vessel 700 and increases the mean WSS exerted on the endothelium of the accepting peripheral vessel 700, to increase the overall diameter and lumen diameter of the accepting peripheral vessel 700 located, for example, in an arm or leg. The diameter of blood vessels such as peripheral veins can be determined by measuring the diameter of the lumen, which is the open space at the center of blood vessel where blood is flowing or by measuring the diameter of the overall vessel, which includes the open space and the walls of the blood vessel.

The invention also relates to simultaneously and persistently increasing the overall diameter and lumen diameter of a peripheral vein or artery by directing blood into or out of the peripheral vein or artery, thereby increasing the mean speed of the blood in the peripheral vein or artery and increasing the mean WSS on the endothelium of the peripheral vein or artery. Systems are described wherein the mean speed of the blood in a peripheral vein or artery and the mean WSS on the endothelium of the peripheral vein or artery is increased by using a blood pump system. Preferably, the pump directs blood into the peripheral vein, wherein the pumped blood has reduced pulsatility, such as when the pulse pressure is lower than blood in a peripheral artery.

The system 10 is suitable to maintain a flow rate preferably between 50 mL/min and 2500 mL/min and optionally between 50 mL/min and 1000 mL/min while also maintaining a pressure range between 25 mmHg and 350 mmHg. As previously described, the control system 14 may be optimized to maintain a steady mean wall shear stress of between 0.76 Pa and 23 Pa in peripheral veins such that the overall diameter and lumen diameter of the peripheral veins are persistently increased by as much as 5% to more than 200%.

The systems described herein also increase the mean speed of blood in peripheral veins. At rest, the mean speed of blood in the cephalic vein in humans is generally between 5 to 9 cm/s (0.05 to 0.09 m/s). For the systems described herein, the mean speed of blood in the peripheral vein is increased to a range between 10 cm/s and 120 cm/s (0.1 and 1.2 m/s), preferably to a range between 25 cm/s and 100 cm/s (0.25 m/s and 1.0 m/s), depending on the initial overall diameter or lumen diameter of peripheral accepting vein and the final overall or lumen diameter that is desired. The systems described herein also increase the mean speed of blood in peripheral arteries. At rest, the mean speed of blood in the brachial artery is generally between 10 and 15 cm/s (0.1 and 0.15 m/s). For the systems and methods described herein, the mean speed of blood in the peripheral artery is increased to a range between 10 cm/s and 120 cm/s (0.1 and 1.2 m/s), preferably to a range between 25 cm/s and 100 cm/s (0.25 and 1.0 m/s), depending on the initial overall diameter or lumen diameter of artery the final overall or lumen diameter that is desired.

Preferably, the mean blood velocity is increased for between 1 day and 84 days, or preferably, between 7 and 42 days, to induce a persistent increase in the overall diameter and lumen diameter in the peripheral accepting vein, peripheral accepting artery, peripheral donating vein, or peripheral donating artery such that veins and arteries that were initially ineligible or suboptimal for use as a hemodialysis access site or bypass graft due to a small vein or artery diameter become usable. This can also be accomplished by intermittently increasing mean blood velocity during the treatment period, with intervening periods of normal mean blood velocity.

Studies have shown that baseline hemodynamic forces and changes in hemodynamic forces within veins and arteries play a vital role in determining the overall diameter and lumen diameter, and the length of those veins and arteries. For example, persistent increases in mean blood velocity and mean WSS can lead to a persistent increase in the lumen diameter and overall diameter, and length, of veins and arteries. The elevated mean blood velocity and mean WSS are sensed by endothelial cells, which trigger signaling mechanisms that result in stimulation of vascular smooth muscle cells, attraction of monocytes and macrophages, and synthesis and release of proteases capable of degrading components of the extracellular matrix such as collagen and elastin. As such, the present invention relates to increasing mean blood velocity and mean WSS for a period of time sufficient to result in vein and artery remodeling and an increase in the overall diameter and the lumen diameter, and length, of the veins and arteries.

The systems described herein increase the mean WSS level in a peripheral vein or artery. Normal mean WSS for veins ranges between 0.076 Pa and 0.76 Pa. The systems described herein increase the mean WSS level in veins to a range between 0.76 Pa and 23 Pa, preferably to a range between 2.5 Pa and 10 Pa. Normal mean WSS for arteries ranges between 0.3 Pa and 1.5 Pa. To persistently increase the overall diameter and lumen diameter of arteries, the systems and methods described herein increase the mean WSS level to a range between 1.5 Pa and 23 Pa, preferably to a range between 2.5 Pa and 10 Pa. Preferably, the mean WSS is increased for between 1 days and 84 days, or preferably, between 7 and 42 days, to induce a persistent increase in the overall diameter and lumen diameter in the peripheral accepting vein, peripheral accepting artery, peripheral donating vein, or peripheral donating artery such that veins and arteries that were initially ineligible or suboptimal for use as a hemodialysis access site or bypass graft due to a small vein and artery diameter become usable. This can also be accomplished by intermittently increasing mean WSS during the treatment period, with intervening periods of normal mean WSS.

In some circumstances, sustained periods of mean WSS levels in the peripheral veins lower than 0.076 Pa or in peripheral arteries lower than 1.5 Pa may result in increased overall diameter and lumen diameter of these veins and arteries, but the extent and rate of this increase is not likely to be clinically meaningful or compatible with routine clinical practice. Sustained mean WSS levels in peripheral veins and arteries higher than about 23 Pa are likely to cause denudation (loss) of the endothelium of the veins or damage to the endothelium of the veins. Denudation of the endothelium or damage to the endothelium of blood vessels is known to reduce the increase in overall diameter and lumen diameter of blood vessels in the setting of increased in mean blood velocity and mean WSS. The increased mean WSS induces sufficient persistent increase in the overall diameter and lumen diameter, or length, in the veins and arteries, such that those that were initially ineligible or suboptimal for use as a hemodialysis access site or bypass graft due to a small vein or artery diameter become usable or more optimal. The diameter of the peripheral accepting vein, peripheral accepting artery, peripheral donating vein, or peripheral donating artery can be determined intermittently, such as every 1 day, 3 days, 1 week, or multiple weeks for example, to allow for pump speed adjustment in order to optimize the rate and extent of the persistent increase in the overall diameter and lumen diameter of the vein and artery during the treatment period.

The systems described herein also increase the mean speed of blood in peripheral veins. At rest, the mean speed of blood in the cephalic vein in humans is generally between 5 and 9 cm/s (0.05 and 0.09 m/s). For the systems described herein, the mean speed of blood in the peripheral vein is increased to a range between 10 cm/s and 120 cm/s (0.1 and 1.2 m/s), preferably to a range between 25 cm/s and 100 cm/s (0.25 m/s and 1.0 m/s), depending on the initial overall diameter or lumen diameter of the peripheral accepting vein and the desired final overall diameter and lumen diameter of the peripheral accepting vein. The systems described herein also increase the mean speed of blood in peripheral arteries. At rest, the mean speed of blood in the brachial artery is generally between 10-15 cm/s (0.1 and 0.15 m/s). For the systems and methods described herein, the mean speed of blood in the peripheral artery is increased to a range between 10 cm/s and 120 cm/s (0.1 and 1.2 m/s), preferably to a range between 25 cm/s and 100 cm/s (0.25 and 1.0 m/s), depending on the initial overall diameter or lumen diameter of the peripheral artery and the desired final overall diameter or lumen diameter of the peripheral artery. Preferably, the mean blood velocity is increased for between 1 day and 84 days, or preferably, between 7 and 42 days, to induce a persistent increase in the overall diameter and the lumen diameter, or length, of the peripheral accepting vein, peripheral accepting artery, peripheral donating vein, or peripheral donating artery such that veins and arteries that were initially ineligible or suboptimal for use as a hemodialysis access site or bypass graft due to a small vein or artery diameter or inadequate length become usable. Mean blood velocity levels in the accepting peripheral vein, peripheral accepting artery, peripheral donating vein, or peripheral donating artery lower than 10 cm/s (0.1 m/s) may result in increased overall diameter and lumen diameter of these veins and arteries, but the extent and rate of this increase is not likely to be clinically meaningful or compatible with routine clinical practice. Mean blood velocity levels in peripheral accepting veins, peripheral accepting arteries, peripheral donating veins, or peripheral donating arteries higher than about 120 cm/s (1.2 m/s) are likely to cause denudation (loss) of the endothelium of the veins or damage to the endothelium of veins. Denudation or damage of the endothelium of blood vessels is known to reduce the increase in the overall diameter and lumen diameter of blood vessels observed in the setting of increased mean blood velocity. The increased mean blood velocity in the desired range and for a sufficient period of time induces sufficient persistent increase in the overall diameter and lumen diameter, or length, in the veins and arteries, such that those that were initially ineligible or suboptimal for use as a hemodialysis access site or bypass graft due to a small vein or artery diameter or inadequate length become usable. The overall diameter or lumen diameter of the peripheral accepting vein, peripheral accepting artery, peripheral donating vein, and peripheral donating artery can be determined intermittently, such as every minute(s), hour(s), 1 day, 3 days, 1 week, or multiple weeks for example, to allow for pump speed adjustment in order to optimize the rate and extent of the persistent increase in the overall diameter and lumen diameter of the vein and artery during the treatment period.

In one embodiment shown in FIG. 34, the system 10 includes the blood pump 25, the pair of conduits 12, and the control device 21 for moving deoxygenated venous blood from a donating vein or location in the venous system of a patient to a peripheral accepting vein. In various embodiments, the peripheral accepting vein may be a cephalic vein, radial vein, median vein, ulnar vein, antecubital vein, median cephalic vein, median basilic vein, basilic vein, brachial vein, lesser saphenous vein, greater saphenous vein, femoral vein, or other veins. Other veins that might be useful in the creation of a hemodialysis access site or bypass graft or other veins useful for other vascular surgery procedures requiring the use of veins may be used. The conduits 12 move the deoxygenated blood to the peripheral accepting vein. The persistently elevated mean speed of the blood and the elevated mean WSS in the peripheral vessel causes a persistent and progressive increase in the overall diameter and lumen diameter of the peripheral accepting vein. Thus, the system 10 of the present invention advantageously increases the diameter or length of the peripheral vein 4 so that it can be used, for example, to construct an hemodialysis access site (such as an AVF or AVG), a bypass graft, or used in another clinical setting where a vein of a certain diameter or length is needed, as determined by one skilled in the art.

As used herein, deoxygenated blood is blood that has passed through the capillary system and had oxygen removed by the surrounding tissues and then passed into the venous system. A peripheral vein, as used herein, means any vein with a portion residing outside of the chest, abdomen, or pelvis. In the embodiment shown in FIG. 37, the peripheral accepting vein 712 is the cephalic vein. However, in other embodiments, the peripheral accepting vein may be a radial vein, median vein, ulnar vein, antecubital vein, median cephalic vein, median basilic vein, basilic vein, brachial vein, lesser saphenous vein, greater saphenous vein, femoral vein, or other veins. In addition to a peripheral vein, other veins that might be useful in the creation of a hemodialysis access site or bypass graft or other veins useful for other vascular surgery procedures requiring the use of veins may also be used as accepting veins, such as those residing in the chest, abdomen, and pelvis.

FIG. 37 illustrates another embodiment for using the system 10 to increase the overall diameter and lumen diameter of a blood vessel. In this embodiment, the system 10 is configured to remove deoxygenated blood from a donating vein 700 and move the blood to the superior vena cava or right atrium 702 of the heart 704. As shown, an inflow conduit 706 is connected in fluid communication with the donating vein 700, in this case the cephalic vein. In one embodiment, the connection may be made using a short ePTFE segment of the inflow conduit 706 that is used to secure the inflow conduit 706 to the donating vein 700 while the remaining segment of the inflow conduit is made using polyurethane. In other embodiments, at least a portion of the inflow conduit or the outflow conduit further comprises nitinol, for kink and compression resistance. As shown, one end of the outflow conduit 710 is connected to the blood pump 25 while the other end of the outflow conduit is fluidly connected to the superior vena cava and the right atrium 702 by an intravascular portion. For the embodiment of FIG. 37, a blood pump is used increase the rate at which blood moves from the donating vein 700 to the superior vena cava and right atrium 702 of the heart 704 in order to achieve a desired elevated level of mean blood velocity and elevated level of mean WSS in the donating vein 700. The pump is operated at a rate and for a time sufficient to result in a desired persistent increase in the overall diameter and lumen diameter of the donating vein, such as a 10% increase, a 25% increase, a 50% increase, or an increase of 100% or more from the starting diameter. In a further embodiment, one or more venous valves between the junction of the inflow conduit 706 and the donating vein 700, and the right atrium 702 may be rendered incompetent or less competent (using any of the methods available to one skilled in the art) to allow blood to flow in a retrograde fashion in the donating vein 700 and then into the inflow conduit 706.

Figure 38:
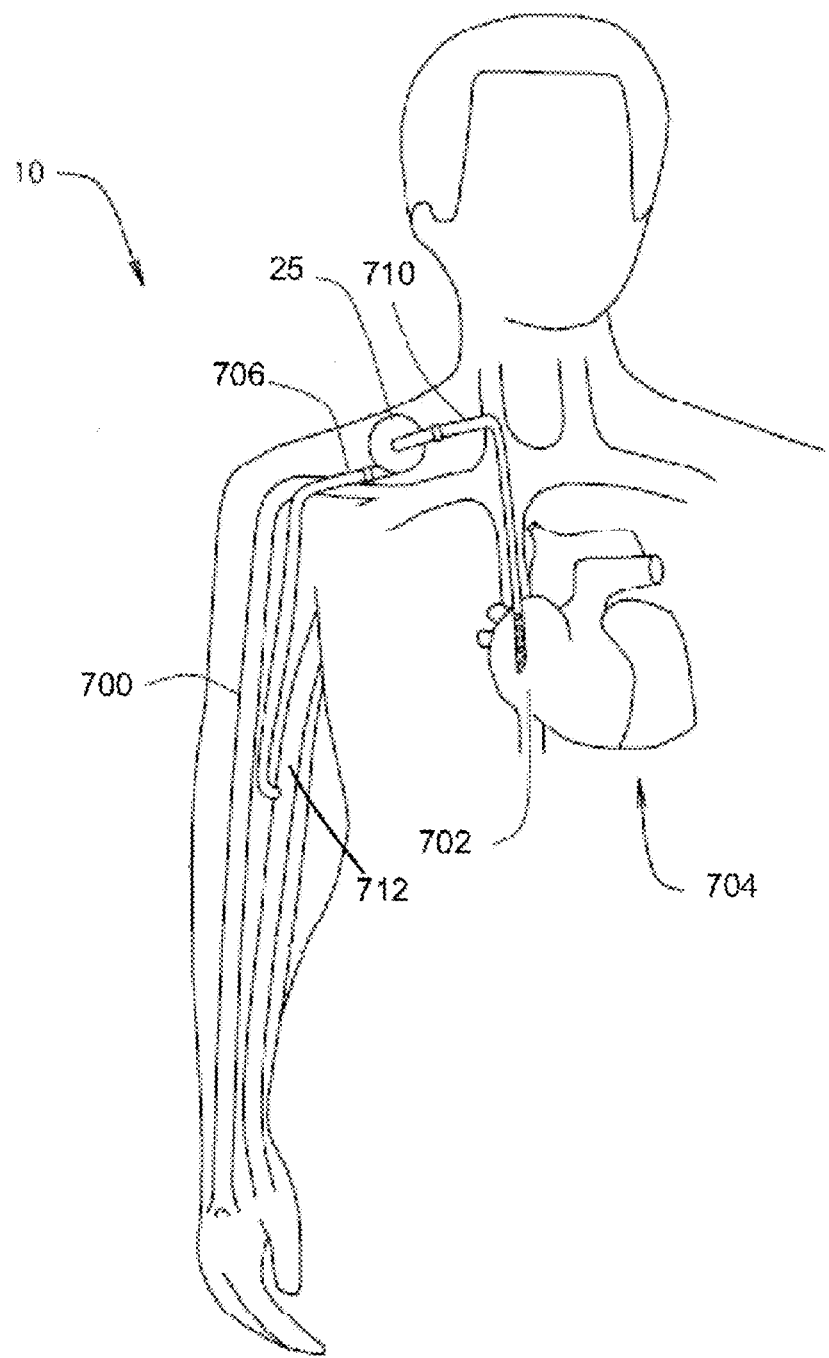
FIG. 38 is a schematic view of the pump system as applied to a circulatory system of a patient according to a second embodiment.

FIG. 38 illustrates another embodiment for using the system 10 to increase the overall diameter and lumen diameter of a blood vessel. In this embodiment, the system 10 is configured to remove oxygenated blood from a donating artery 712 (in this case the brachial artery) and move the blood to the superior vena cava and right atrium 702 of the heart 704. As shown, an inflow conduit 706 is connected in fluid communication with the donating artery 712. In one embodiment, the connection may be made using a short ePTFE segment of the inflow conduit 706 that is used to secure the inflow conduit to the donating artery 712 while the remaining segment of the inflow conduit is made using polyurethane. In other embodiments, one or both segments of the inflow conduit 706 further comprise nitinol, such as for kink and compression resistance. As shown, one end of the outflow conduit 710 is connected to the blood pump 25 while the other end of the outflow conduit is fluidly connected to the superior vena cava and the right atrium 702 by an intravascular portion. For the embodiment of FIG. 38, a blood pump is used increase the rate at which blood moves from the donating artery 712 to the right atrium 702 of the heart 704 in order to achieve a desired elevated level of mean blood velocity and elevated mean level of WSS in the donating artery 712. The pump is operated at a rate and for a time sufficient to result in a desired persistent increase in the overall diameter and lumen diameter of the donating artery, such as a 10% increase, a 25% increase, a 50% increase, or an increase of 100% or more from the starting diameter.

In other embodiments, oxygenated arterial blood may be moved from a donating artery to an accepting location. Donating arteries may include, but are not limited to, a radial artery, ulnar artery, interosseous artery, brachial artery, anterior tibial artery, posterior tibial artery, peroneal artery, popliteal artery, profunda artery, superficial femoral artery, or femoral artery.

Figure 39:
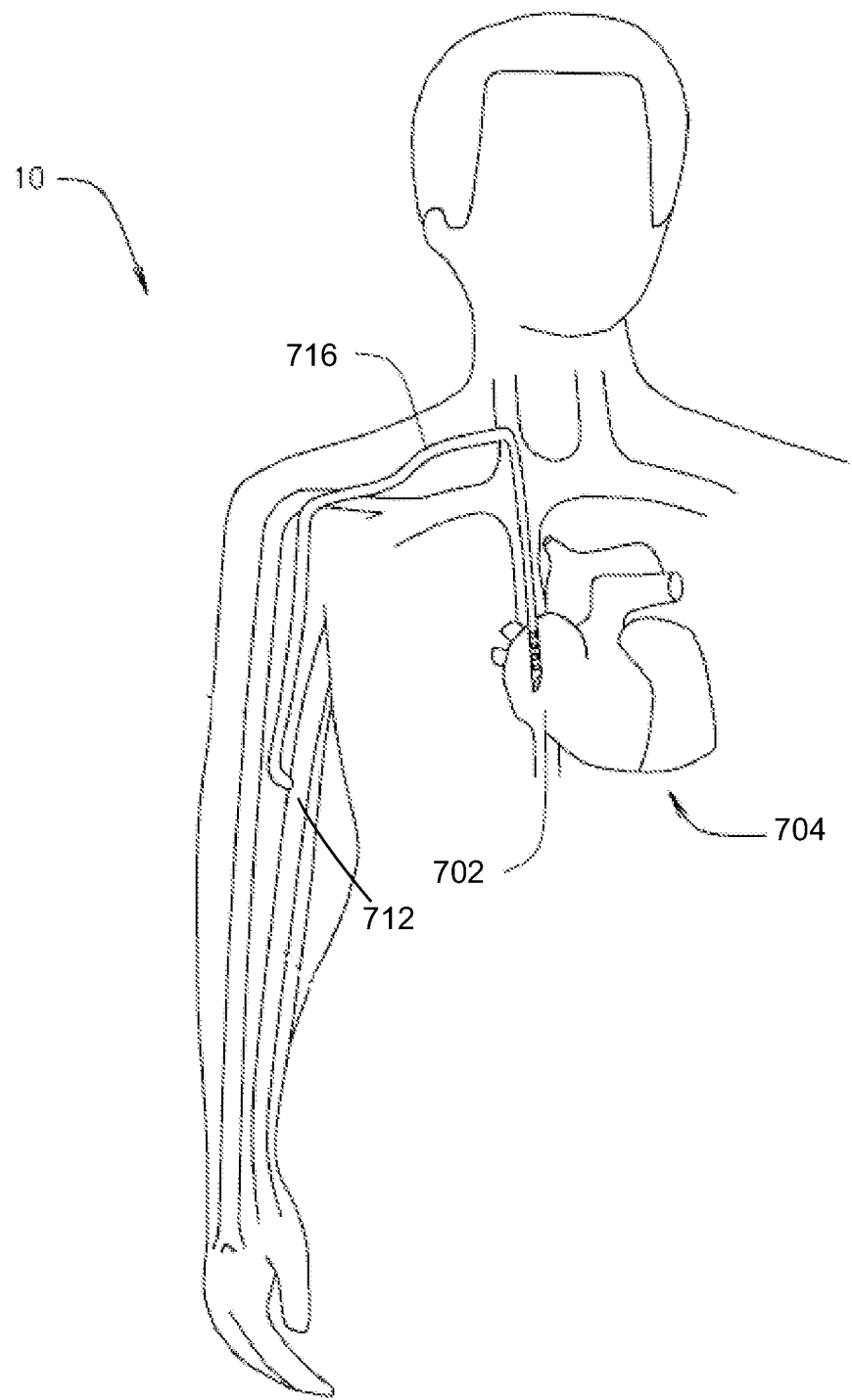
FIG. 39 is a schematic view of the system without a pump as applied to a circulatory system of a patient according to a third embodiment.

FIG. 39 illustrates another embodiment for using the system 10 to increase the overall diameter and lumen diameter of a blood vessel. In this embodiment, the system 10 is configured to remove oxygenated blood from a donating artery 712 (in this case the brachial artery) and move the blood to the superior vena cava and right atrium 702 of the heart 704. As shown, a conduit 716 is connected in fluid communication with the donating artery 712. In one embodiment, the connection may be made using a short ePTFE segment of the conduit 716 that is used to secure the inflow conduit to the donating artery 712 while the remaining segment of the inflow conduit is made using polyurethane. In other embodiments, one or both segments of the conduit 716 further comprise nitinol, such as for kink and compression resistance. For the embodiment of FIG. 39, there is no pump and blood moves passively from the higher pressure donating artery 712 to the lower pressure superior vena cava and right atrium 702, and the conduit 716 is configured in length and lumen diameter to achieve a desired elevated level of mean blood velocity and mean WSS in the donating artery 712. The conduit 716 remains in place for a time sufficient to result in a desired persistent increase in the overall diameter and lumen diameter of the donating artery 712, such as a 10% increase, a 25% increase, a 50% increase, or an increase of 100% or more from the starting diameter.

Figure 40:
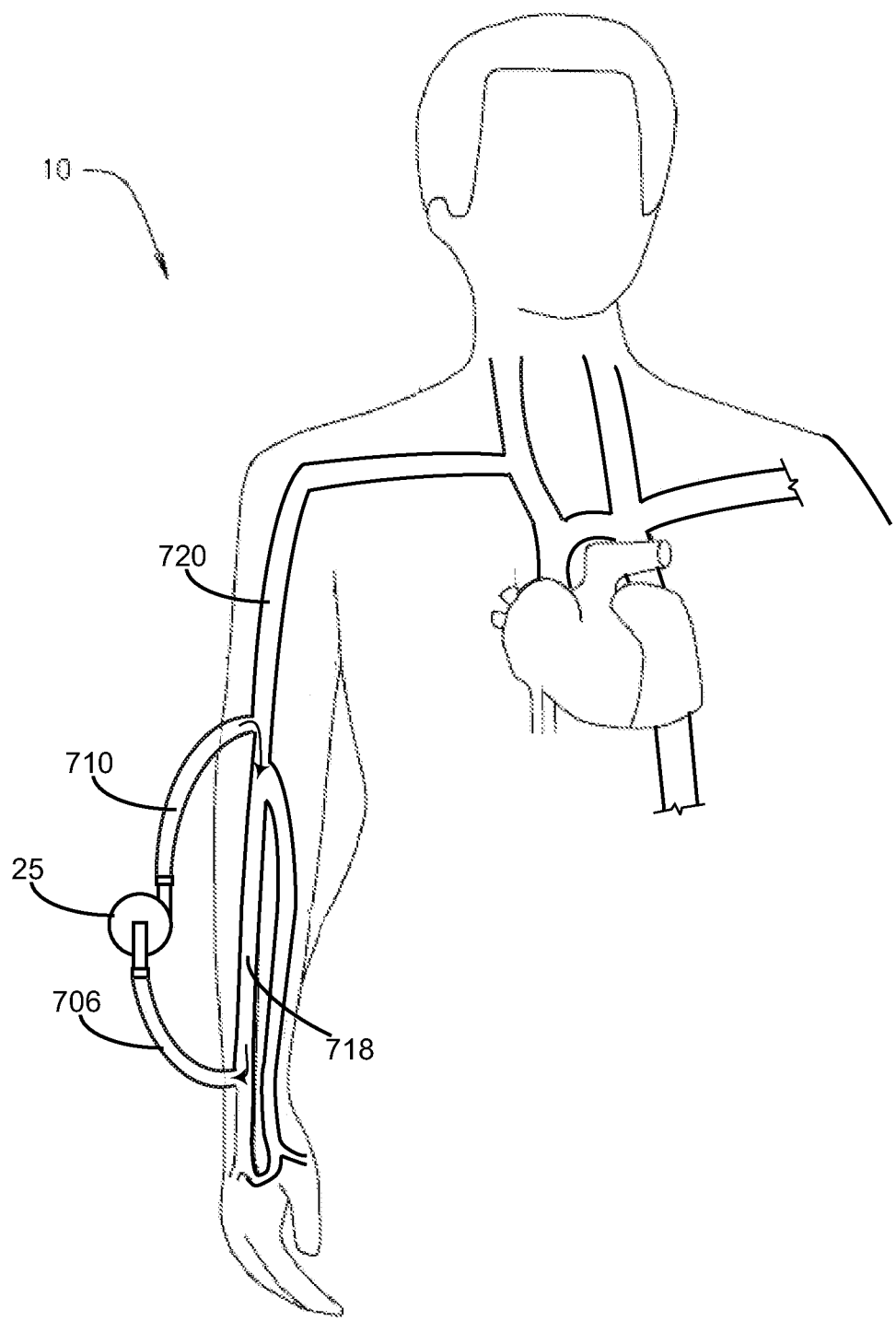
FIG. 40 is a schematic view of the pump system as applied to a circulatory system of a patient according to a fourth embodiment.

FIG. 40 illustrates another embodiment for using the system 10 to increase the overall diameter and lumen diameter of a peripheral artery. In this embodiment, the system 10 is configured to remove oxygenated blood from a target artery 718, such as the radial artery, and move the blood to an accepting artery 720, such as the brachial artery. As shown, an inflow conduit 706 is connected in fluid communication with the target artery 718. In one embodiment, the connection between the inflow conduit 706 and an artery or the outflow conduit 710 and an artery may be made using a short ePTFE segment of the respective conduit that is used to fluidly connect the inflow conduit to the target artery 718 or the outflow conduit 710 that is fluidly connected to the accepting artery 720, while the remaining segments of the inflow and outflow conduits can be made using polyurethane. In other embodiments, one or both segments of the inflow conduit 706 or the outflow conduit 710 further comprise nitinol, such as for kink and compression resistance.

As shown, one end of the outflow conduit 710 is connected to the blood pump 25 while the other end of the outflow conduit is fluidly connected to the accepting artery 720. For the embodiment of FIG. 40, the blood pump 25 is used increase the rate at which blood is withdrawn from the target artery 718 in order to achieve a desired elevated level of mean blood velocity and elevated mean level of WSS in the target artery. The pump is operated at a rate and for a time sufficient to result in a desired persistent increase in the overall diameter and lumen diameter of the target artery 718, such as a 10% increase, a 25% increase, a 50% increase, or an increase of 100% or more from the starting diameter.

While the invention has been explained in relation to exemplary aspects and embodiments, it is to be understood that various modifications thereof will become apparent to those skilled in the art upon reading the description. Therefore, it is to be understood that the invention disclosed herein is intended to cover such modifications as fall within the scope of the appended claims.

What is claimed is:

1. A method of estimating and controlling a wall shear stress in a blood vessel comprising:
   a) estimating a blood viscosity;
   b) measuring at least one motor state variable of a blood pump system selected from a voltage, a current, or a pump speed;
   c) estimating a blood flow rate in the blood pump system;
   d) measuring a pressure in the blood vessel;
   e) determining a vascular resistance of the blood vessel from the estimated blood flow rate and the measured pressure in the blood vessel;
   f) estimating a radius of the blood vessel;
   g) determining the wall shear stress from the estimated blood viscosity, the estimated blood flow rate, and the radius of the blood vessel;
   h) comparing the determined wall shear stress with a predetermined reference value;
   i) adjusting the pump speed when the determined wall shear stress does not approximate the predetermined reference value; and
   j) repeating steps a-i until the determined wall shear stress approximates the predetermined reference value.

2. The method of claim 1 where the wall shear stress is periodically determined and adjusted as necessary, at an interval of 1 ms, 10 ms, 100 ms, 1 s, 1 min, 1 hour, 1 day, 7 days, 14 days, and 28 days.

3. The method of claim 1 where blood viscosity is periodically estimated based on its known relationship with a measured hematocrit and an approximate wall shear stress at an interval of about 1 to 14 days.

4. The method of claim 1 where estimates of the blood flow rate in the blood pump system are periodically calibrated using actual measured values at an interval of about 1 to 14 days.

5. The method of claim 1 where estimates of the radius of the blood vessel are periodically calibrated using actual measured values at an interval of about 1 to 14 days.

6. The method of claim 1 where the pump speed is increased and an alarm indication is triggered when the blood flow rate drops below a predetermined safety reference value.

7. The method of claim 1 where the pump speed is decreased and an alarm indication is triggered when the wall shear stress exceeds a predetermined safety reference value.

8. A method of estimating and controlling a wall shear stress in a blood vessel using a blood pump system comprising:
   a) estimating a blood viscosity;
   b) measuring at least one motor state variable of the blood pump system selected from a voltage, a current, or a pump speed;
   c) estimating a blood flow rate and a pressure head in the blood pump system;
   d) calculating a vascular resistance of the blood vessel from the estimated blood flow rate and the estimated pressure head;
   e) estimating a radius of the blood vessel;
   f) determining the wall shear stress from the estimated blood viscosity, the estimated blood flow rate, and the radius of the blood vessel;
   g) comparing the determined wall shear stress with a predetermined reference value;
   h) adjusting the pump speed when the determined wall shear stress does not approximate the predetermined reference value; and
   i) repeating steps a-h until the determined wall shear stress approximates the predetermined reference value.

9. The method of claim 8 where the wall shear stress is periodically determined and adjusted as necessary, at an interval of 1 ms, 10 ms, 100 ms, 1 s, 1 min, 1 hour, 1 day, 7 days, 14 days, or 28 days.

10. The method of claim 8 where the blood viscosity is periodically estimated based on its known relationship with a measured hematocrit and an approximate wall shear stress at an interval of about 1 to 14 days.

11. The method of claim 8 where estimates of the blood flow rate are periodically calibrated using actual measured values at an interval of about 1 to 14 days.

12. The method of claim 8 where estimates of the pressure head are periodically calibrated using actual measured values at an interval of about 1 to 14 days.

13. The method of claim 8 where estimates of the radius of the blood vessel are periodically calibrated using actual measured values at an interval of about 1 to 14 days.

14. The method of claim 8 where the pump speed is increased and an alarm indication is triggered when the blood flow rate drops below a predetermined safety reference value.

15. The method of claim 8 where the pump speed is decreased and an alarm indication is triggered when the wall shear stress exceeds the predetermined safety reference value.

16. A method of determining and controlling a wall shear stress in a blood vessel comprising:
   a) measuring a blood viscosity;
   b) measuring a blood flow rate in a blood pump system or the blood vessel;
   c) measuring a radius of the blood vessel;
   d) determining the wall shear stress in the blood vessel from the measured blood viscosity, the measured flow rate, and the radius of the blood vessel;
   e) comparing the determined wall shear stress to a predetermined reference value;
   f) adjusting a blood pump speed when the determined wall shear stress does not approximate the predetermined reference value; and
   g) repeating steps a-f until the determined wall shear stress approximates the predetermined reference value.

17. A method of computing and controlling a wall shear stress in a blood vessel comprising:
   a) estimating a blood viscosity;

b) measuring a blood flow rate in a blood pump system or the blood vessel;
c) measuring a radius of the blood vessel;
d) determining the wall shear stress from the estimated blood viscosity, the measured blood flow rate, and the radius of the blood vessel;
e) comparing the determined wall shear stress with a predetermined reference value;
f) adjusting a blood pump speed when the determined wall shear stress does not approximate the predetermined reference value; and
g) repeating steps a-f until the determined wall shear stress approximates the predetermined reference value.

* * * * *